United States Patent
Gross et al.

(10) Patent No.: US 8,993,718 B2
(45) Date of Patent: Mar. 31, 2015

(54) METHODS AND COMPOSITIONS FOR DETECTING AND MODULATING O-GLYCOSYLATION

(71) Applicant: President and Fellows of Harvard College, Cambridge, MA (US)

(72) Inventors: Benjamin J. Gross, Philadelphia, PA (US); Suzanne Walker Kahne, Brookline, MA (US); Jonathan G. Swoboda, Oil City, PA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/013,860

(22) Filed: Aug. 29, 2013

(65) Prior Publication Data
US 2014/0187444 A1    Jul. 3, 2014

Related U.S. Application Data

(63) Continuation of application No. 12/664,559, filed as application No. PCT/US2008/007410 on Jun. 13, 2008, now Pat. No. 8,524,444.

(60) Provisional application No. 60/934,803, filed on Jun. 15, 2007.

(51) Int. Cl.
| | | |
|---|---|---|
| A61K 38/00 | (2006.01) | |
| C12Q 1/37 | (2006.01) | |
| C07K 7/06 | (2006.01) | |
| C12Q 1/34 | (2006.01) | |
| C12N 9/12 | (2006.01) | |

(52) U.S. Cl.
CPC ... *C12Q 1/37* (2013.01); *C07K 7/06* (2013.01); *C12Q 1/34* (2013.01); *C12N 9/12* (2013.01); *C07K 2319/50* (2013.01); *C07K 2319/60* (2013.01); *G01N 2333/924* (2013.01); *G01N 2440/38* (2013.01); *G01N 2500/02* (2013.01)
USPC ........................................................ 530/300

(58) Field of Classification Search
USPC ........................................................ 530/300
See application file for complete search history.

(56) References Cited

U.S. PATENT DOCUMENTS

| | | | |
|---|---|---|---|
| 3,854,480 A | 12/1974 | Zaffaroni | |
| 4,270,537 A | 6/1981 | Romaine | |
| 4,420,486 A | 12/1983 | Ohyama et al. | |
| 4,452,775 A | 6/1984 | Kent | |
| 4,596,556 A | 6/1986 | Morrow et al. | |
| 4,675,189 A | 6/1987 | Kent et al. | |
| 4,790,824 A | 12/1988 | Morrow et al. | |
| 4,886,499 A | 12/1989 | Cirelli et al. | |
| 4,940,460 A | 7/1990 | Casey et al. | |
| 4,941,880 A | 7/1990 | Burns | |
| 5,015,235 A | 5/1991 | Crossman | |
| 5,064,413 A | 11/1991 | McKinnon et al. | |
| 5,133,974 A | 7/1992 | Paradissis et al. | |
| 5,141,496 A | 8/1992 | Dalto et al. | |
| 5,190,521 A | 3/1993 | Hubbard et al. | |
| 5,312,335 A | 5/1994 | McKinnon et al. | |
| 5,328,483 A | 7/1994 | Jacoby | |
| 5,334,144 A | 8/1994 | Alchas et al. | |
| 5,339,163 A | 8/1994 | Homma et al. | |
| 5,383,851 A | 1/1995 | McKinnon, Jr. et al. | |
| 5,407,686 A | 4/1995 | Patel et al. | |
| 5,417,662 A | 5/1995 | Hjertman et al. | |
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,649,912 A | 7/1997 | Peterson | |
| 5,704,911 A | 1/1998 | Parsons | |
| 5,736,152 A | 4/1998 | Dunn | |
| 5,893,397 A | 4/1999 | Peterson et al. | |

(Continued)

FOREIGN PATENT DOCUMENTS

| | | | |
|---|---|---|---|
| CH | 570990 A | 12/1975 | |
| CH | 572305 A | 2/1976 | |

(Continued)

OTHER PUBLICATIONS

Ninkovic et al. "O-glycosylated human MUC1 repeats are processed in vitro by immunoproteasomes", The J of Immunology, 2007, 179:2380-2388.*
Extended European Search Report for EP 10783701.5, mailed Mar. 20, 2013.
International Search Report and Written Opinion for PCT/US2010/001596, mailed Jan. 31, 2011.
International Preliminary Report on Patentability for PCT/US2010/001596, mailed Dec. 15, 2011.
International Search Report and Written Opinion for PCT/US2007/008806, mailed Jun. 6, 2008.
International Preliminary Report on Patentability for PCT/US2007/008806, mailed Oct. 23, 2008.
International Search Report and Written Opinion for PCT/US2008/007410, mailed Sep. 16, 2008.

(Continued)

*Primary Examiner* — Bin Shen
(74) *Attorney, Agent, or Firm* — Wolf, Greenfield & Sacks, P.C.; C. Hunter Baker

(57) ABSTRACT

The invention relates to methods and products for modulating glycosylation of proteins. The invention is useful for identifying therapeutic compounds to treat glycosylation-associated disorders such as neurodegeneration, diabetes, including complications of diabetes such as insulin resistance, nephropathy, microvascular damage, and endothelial dysfunction. The invention is also useful for identifying therapeutic compounds to treat de-glycosylation-associated disorders such as ischemic damage and traumatic injury. The invention also relates in part to assays that are useful for identifying and testing candidate compounds for modulating glycosylation of proteins and also relates in part to compounds to treat glycosylation-associated diseases and disorders.

19 Claims, 22 Drawing Sheets

(56) References Cited

U.S. PATENT DOCUMENTS

| | | | |
|---|---|---|---|
| 5,993,412 | A | 11/1999 | Deily et al. |
| 6,388,063 | B1 | 5/2002 | Plowman et al. |
| 6,476,187 | B1 | 11/2002 | Cone et al. |
| 6,852,838 | B2 | 2/2005 | Valenzuela et al. |
| 6,905,681 | B1 | 6/2005 | June et al. |
| 6,916,636 | B2 | 7/2005 | Marx et al. |
| 6,924,356 | B2 | 8/2005 | Ruben et al. |
| 6,955,894 | B1 | 10/2005 | Gatanaga et al. |
| 6,969,758 | B2 | 11/2005 | Ferrara et al. |
| 8,524,444 | B2 | 9/2013 | Gross et al. |
| 2002/0128235 | A1 | 9/2002 | Konrad et al. |
| 2003/0032054 | A1 | 2/2003 | Colyer et al. |
| 2003/0087328 | A1 | 5/2003 | Pollok et al. |
| 2003/0186948 | A1 | 10/2003 | Kudlow et al. |
| 2004/0191811 | A1 | 9/2004 | Burghardt et al. |
| 2004/0259910 | A1 | 12/2004 | Bolin et al. |
| 2005/0026266 | A1 | 2/2005 | Clausen et al. |
| 2005/0032145 | A1 | 2/2005 | Burghardt et al. |
| 2005/0113407 | A1 | 5/2005 | Bolin et al. |
| 2005/0113436 | A1 | 5/2005 | Elokdah et al. |
| 2005/0250678 | A1 | 11/2005 | DeFrees et al. |
| 2006/0099150 | A1 | 5/2006 | Houston et al. |
| 2006/0099688 | A1 | 5/2006 | Clausen et al. |
| 2007/0027068 | A1 | 2/2007 | DeFrees et al. |
| 2009/0163545 | A1 | 6/2009 | Goldfarb |
| 2009/0325944 | A1 | 12/2009 | Kahne et al. |
| 2010/0290987 | A1 | 11/2010 | Gross et al. |
| 2012/0108605 | A1 | 5/2012 | Kahne et al. |

FOREIGN PATENT DOCUMENTS

| | | |
|---|---|---|
| FR | 2179293 A5 | 11/1973 |
| GB | 1330611 A | 9/1973 |
| WO | WO 95/24929 A2 | 9/1995 |
| WO | WO 97/13537 A1 | 4/1997 |
| WO | WO 97/37705 A1 | 10/1997 |
| WO | WO 99/34850 A1 | 7/1999 |
| WO | WO 2007/120638 A2 | 10/2007 |
| WO | WO 2008/156676 A1 | 12/2008 |
| WO | WO 2009/036341 A2 | 3/2009 |
| WO | WO 2009/086952 A2 | 7/2009 |
| WO | WO 2010/141074 A2 | 12/2010 |
| WO | WO 2013/006758 A1 | 1/2013 |

OTHER PUBLICATIONS

International Preliminary Report on Patentability for PCT/US2008/007410, mailed Dec. 30, 2009.

International Search Report and Written Opinion for PCT/US2011/051431, mailed Feb. 29, 2012.

International Preliminary Report on Patentability for PCT/US2011/051431, mailed Mar. 28, 2013.

International Search Report and Written Opinion for PCT/US2012/045675, mailed Nov. 22, 2012.

International Preliminary Report on Patentability for PCT/US2012/045675, mailed Jan. 16, 2014.

Database Registry [Online] Chemical Abstracts Service, Columbus, Ohio, US; Database accession No. 1094798-35-2; Jan. 21, 2009.

PubChem Compound submission: NIH/NCBI; Accession No. 1352610; Jul. 11, 2005.

PubChem Compound submission: NIH/NCBI; Accession No. 2816723; Sep. 9, 2005.

PubChem Compound submission: NIH/NCBI; Accession No. 3531968; Sep. 9, 2005.

PubChem Compound submission: NIH/NCBI; Accession No. 3655724; Sep. 10, 2005.

PubChem Compound submission: NIH/NCBI; Accession No. 4048808; Sep. 13, 2005.

PubChem Compound submission: NIH/NCBI; Accession No. 4247320; Sep. 14, 2005.

PubChem Compound submission: NIH/NCBI; Accession No. 5309478; Dec. 9, 2005.

PubChem Compound submission: NIH/NCBI; Accession No. 6619624; Jun. 5, 2006.

PubChem Compound submission: NIH/NCBI; Accession No. 6619906; Jun. 5, 2006.

PubChem Compound submission: NIH/NCBI; Accession No. 6619938; Jun. 5, 2006.

PubChem Compound submission: NIH/NCBI; Accession No. 6619971; Jun. 5, 2006.

PubChem Compound submission: NIH/NCBI; Accession No. 6620110; Jun. 5, 2006.

PubChem Compound submission: NIH/NCBI; Accession No. 6624064; Jun. 5, 2006.

PubChem Compound submission: NIH/NCBI; Accession No. 6624183; Jun. 5, 2006.

[No Author Listed] The CCP4 suite: programs for protein crystallography. Acta Crystallogr D Biol Crystallogr. Collaborative Computational Project, No. 4. Sep. 1, 1994;50(Pt 5):760-3.

Adams et al., Phenix: a comprehensive Python-based system for macromolecular structure solution. Acta Crystallogr D Biol Crystallogr. Feb. 2010;66(Pt 2):213-21. Epub Jan. 22, 2010.

Akimoto et al., Elevated expression of O-GlcNAc-modified proteins and O-GlcNAc transferase in corneas of diabetic Goto-Kakizaki rats. Invest Ophthalmol Vis Sci. Sep. 2003;44(9):3802-9.

Akimoto et al., Hyperglycemia and the O-GlcNAc transferase in rat aortic smooth muscle cells: elevated expression and altered patterns of O-GlcNAcylation. Arch Biochem Biophys. May 15, 2001;389(2):166-75.

Akimoto et al., Increased O-GlcNAc transferase in pancreas of rats with streptozotocin-induced diabetes. Diabetologia. Oct. 2000;43(10):1239-47.

Alexander et al., Mechanism of carbamate inactivation of FAAH: implications for the design of covalent inhibitors and in vivo functional probes for enzymes. Chem Biol. Nov. 2005;12(11):1179-87.

Almerico et al., In-silico screening of new potential Bcl-2/Bcl-xl inhibitors as apoptosis modulators. J Mol Model. Apr. 2009;15(4):349-55. Epub Dec. 6, 2008.

Andres et al., 4-Thiazolidinones: novel inhibitors of the bacterial enzyme MurB. Bioorg Med Chem Lett. Apr. 17, 2000;10(8):715-7.

Arias et al., Prolonged incubation in PUGNAc results in increased protein O-Linked glycosylation and insulin resistance in rat skeletal muscle. Diabetes. Apr. 2004;53(4):921-30.

Arnold et al., The microtubule-associated protein tau is extensively modified with O-linked N-acetylglucosamine. J Biol Chem. Nov. 15, 1996;271(46):28741-4.

Arnold et al., The Swiss-Model workspace: a web-based environment for protein structure homology modelling. Bioinformatics. Jan. 15, 2006;22(2):195-201. Epub Nov. 13, 2005.

Bartlett et al., CAVEAT: A Program to Facilitate the Structure-derived Design of Biologically Active Molecules. Molecular Recognition in Chemical and Biological Problems. Special Pub. Royal Chem Soc. 1989;78:182-196.

Beasley et al., Miniaturized, ultra-high throughput screening of tyrosine kinases using homogeneous, competitive fluorescence immunoassays. Assay Drug Dev Technol. Apr. 2004;2(2):141-51.

Berge et al., Pharmaceutical salts. J Pharm Sci. Jan. 1977;66(1):1-19.

Boehmelt et al., Decreased UDP-GlcNAc levels abrogate proliferation control in EMeg32-deficient cells. EMBO J. Oct. 2, 2000;19(19):5092-104.

Boggon et al., Screening for phasing atoms in protein crystallography. Structure. Jul. 15, 2000;8(7):R143-9.

Bohm, The computer program LUDI: a new method for the de novo design of enzyme inhibitors. J Comput Aided Mol Des. Feb. 1992;6(1):61-78.

Botella et al., Aminolyse de carbamates cycliques analogues de la carboxybiotine ; catalyse métallique et modélisation de transfert de carboxyle. Tetrahedron. 1992;48(24):5111-22. French. Retrieved from DB ACS on STN CA: 117:110975, compound with RN 27087-39-4.

Bowman et al., Small molecule inhibitors of the MDM2-p53 interaction discovered by ensemble-based receptor models. J Am Chem Soc. Oct. 24, 2007;129(42):12809-14. Epub Sep. 29, 2007.

Brown et al., Glycan antagonists and inhibitors: a fount for drug discovery. Crit Rev Biochem Mol Biol. Nov.-Dec. 2007;42(6):481-515.

(56) References Cited

OTHER PUBLICATIONS

Brownlee, Biochemistry and molecular cell biology of diabetic complications. Nature. Dec. 13, 2001;414(6865):813-20.

Brünger et al., Crystallography & NMR system: A new software suite for macromolecular structure determination. Acta Crystallogr D Biol Crystallogr. Sep. 1, 1998;54(Pt 5):905-21.

Buchan et al., tRNA properties help shape codon pair preferences in open reading frames. Nucleic Acids Res. Feb. 9, 2006;34(3):1015-27. Print 2006.

Burns et al., Silencing of the novel p53 target gene Snk/Plk2 leads to mitotic catastrophe in paclitaxel (taxol)-exposed cells. Mol Cell Biol. Aug. 2003;23(16):5556-71.

Caldwell et al., Nutrient sensor O-GlcNAc transferase regulates breast cancer tumorigenesis through targeting of the oncogenic transcription factor FoxM1. Oncogene. May 13, 2010;29(19):2831-42. Epub Mar. 1, 2010.

Campbell et al., A homogeneous immunoassay for cyclic nucleotides based on chemiluminescence energy transfer. Biochem J. Oct. 15, 1983;216(1):185-94.

Chen et al., Alternative O-GlcNAcylation/O-phosphorylation of Ser16 induce different conformational disturbances to the N terminus of murine estrogen receptor beta. Chem Biol. Sep. 2006;13(9):937-44.

Chen et al., Identification of secret agent as the O-GlcNAc transferase that participates in Plum pox virus infection. J Virol. Aug. 2005;79(15):9381-7.

Cheng et al., Alternative O-glycosylation/O-phosphorylation of the murine estrogen receptor beta. Biochemistry. Sep. 26, 2000;39(38):11609-20.

Chou et al., Characterization and dynamics of O-linked glycosylation of human cytokeratin 8 and 18. J Biol Chem. Feb. 25, 1992;267(6):3901-6.

Chou et al., c-Myc is glycosylated at threonine 58, a known phosphorylation site and a mutational hot spot in lymphomas. J Biol Chem. Aug. 11, 1995;270(32):18961-5.

Chou et al., Glycosylation of the c-Myc transactivation domain. Proc Natl Acad Sci U S A. May 9, 1995;92(10):4417-21.

Cieniewski-Bernard et al., Identification of O-linked N-acetylglucosamine proteins in rat skeletal muscle using two-dimensional gel electrophoresis and mass spectrometry. Mol Cell Proteomics. Jun. 2004;3(6):577-85. Epub Feb. 24, 2004.

Clark et al., Diabetes and the accompanying hyperglycemia impairs cardiomyocyte calcium cycling through increased nuclear O-GlcNAcylation. J Biol Chem. Nov. 7, 2003;278(45):44230-7. Epub Aug. 26, 2003.

Clarke et al., Structural insights into mechanism and specificity of O-GlcNAc transferase. Embo J. Oct. 22, 2008;27(20):2780-8. Epub Sep. 25, 2008.

Cohen et al., Molecular modeling software and methods for medicinal chemistry. J Med Chem. Mar. 1990;33(3):883-94.

Cole et al., Cytosolic O-glycosylation is abundant in nerve terminals. J Neurochem. Dec. 2001;79(5):1080-9.

Cole et al., Glycosylation sites flank phosphorylation sites on synapsin I: O-linked N-acetylglucosamine residues are localized within domains mediating synapsin I interactions. J Neurochem. Jul. 1999;73(1):418-28.

Comer et al., Characterization of a mouse monoclonal antibody specific for O-linked N-acetylglucosamine. Anal Biochem. Jun. 15, 2001;293(2):169-77.

Comer et al., O-Glycosylation of nuclear and cytosolic proteins. Dynamic interplay between O-GlcNAc and O-phosphate. J Biol Chem. Sep. 22, 2000;275(38):29179-82.

Comer et al., Reciprocity between O-GlcNAc and O-phosphate on the carboxyl terminal domain of RNA polymerase II. Biochemistry. Jul. 3, 2001;40(26):7845-52.

Comess et al., Affinity-based screening techniques for enhancing lead discovery. Curr Opin Drug Discov Devel. Jul. 2004;7(4):411-6.

Compain et al., Carbohydrate mimetics-based glycosyltransferase inhibitors. Bioorg Med Chem. Dec. 2001;9(12):3077-92.

Compain et al., Design, synthesis and biological evaluation of iminosugar-based glycosyltransferase inhibitors. Curr Top Med Chem. 2003;3(5):541-60.

Copeland et al., Cross-talk between GlcNAcylation and phosphorylation: roles in insulin resistance and glucose toxicity. Am J Physiol Endocrinol Metab. Jul. 2008;295(1):E17-28. Epub Apr. 29, 2008.

De La Fortelle et al., SHARP: A Maximum-Likelihood Heavy-Atom Parameter Refinement Program for the MIR and MAD Mehtods. Methods Enzymol. 1997;276:472-94.

Defronzo, Insulin resistance, hyperinsulinemia, and coronary artery disease: a complex metabolic web. J Cardiovasc Pharmacol. 1992;20 Suppl 11:S1-16.

Dentin et al., Hepatic glucose sensing via the CREB coactivator CRTC2. Science. Mar. 7, 2008;319(5868):1402-5.

Dias et al., Regulation of calcium/calmodulin-dependent kinase IV by O-GlcNAc modification. J Biol Chem. Aug. 7, 2009;284(32):21327-37. Epub Jun. 8, 2009.

Dong et al., Cytoplasmic O-GlcNAc modification of the head domain and the KSP repeat motif of the neurofilament protein neurofilament—H. J Biol Chem. Aug. 23, 1996;271(34):20845-52.

Dong et al., Glycosylation of mammalian neurofilaments. Localization of multiple O-linked N-acetylglucosamine moieties on neurofilament polypeptides L and M. J Biol Chem. Aug. 5, 1993;268(22):16679-87.

Dong et al., Purification and characterization of an O-GlcNAc selective N-acetyl-beta-D-glucosaminidase from rat spleen cytosol. J Biol Chem. Jul. 29, 1994;269(30):19321-30.

Donovan et al., A solid-phase glycosyltransferase assay for high-throughput screening in drug discovery research. Glycoconj J. 1999;16(10):607-15.

Dorfmueller et al., Cell-penetrant, nanomolar O-GlcNAcase inhibitors selective against lysosomal hexosaminidases. Chem Biol. Nov. 24, 2010;17(11):1250-5.

Dorfmueller et al., GlcNAcstatin: a picomolar, selective O-GlcNAcase inhibitor that modulates intracellular O-glcNAcylation levels. J Am Chem Soc. Dec. 27, 2006;128(51):16484-5.

Dorfmueller et al., Substrate and product analogues as human O-GlcNAc transferase inhibitors. Amino Acids. Mar. 2011;40(3):781-92. Epub Jul. 17, 2010.

Du et al., Hyperglycemia inhibits endothelial nitric oxide synthase activity by posttranslational modification at the Akt site. J Clin Invest. Nov. 2001;108(9):1341-8.

Emsley et al., Coot: model-building tools for molecular graphics. Acta Crystallogr D Biol Crystallogr. Dec. 2004;60(Pt 12 Pt 1):2126-32. Epub Nov. 26, 2004.

Emsley et al., Features and development of Coot. Acta Crystallogr D Biol Crystallogr. Apr. 2010;66(Pt 4):486-501. Epub Mar. 24, 2010.

Evans, Scaling and assessment of data quality. Acta Crystallogr D Biol Crystallogr. Jan. 2006;62(Pt 1):72-82. Epub Dec. 14, 2005.

Fan et al., Apoptosis induction with polo-like kinase-1 antisense phosphorothioate oligodeoxynucleotide of colon cancer cell line SW480. World J Gastroenterol. Aug. 7, 2005;11(29):4596-9.

Feng et al., A detergent-based assay for the detection of promiscuous inhibitors. Nat Protoc. 2006;1(2):550-3.

Feng et al., High-throughput assays for promiscuous inhibitors. Nat Chem Biol. Aug. 2005;1(3):146-8. Epub Jul. 3, 2005.

Frantom et al., UDP-(5F)-GlcNAc acts as a slow-binding inhibitor of MshA, a retaining glycosyltransferase. J Am Chem Soc. May 19, 2010;132(19):6626-7.

Friesner et al., Extra precision glide: docking and scoring incorporating a model of hydrophobic enclosure for protein-ligand complexes. J Med Chem. Oct. 19, 2006;49(21):6177-96.

Friesner et al., Glide: a new approach for rapid, accurate docking and scoring. 1. Method and assessment of docking accuracy. J Med Chem. Mar. 25, 2004;47(7):1739-49.

Fujiki et al., GlcNAcylation of a histone methyltransferase in retinoic-acid-induced granulopoiesis. Nature. May 21, 2009;459(7245):455-9. Epub Apr. 19, 2009.

Gambetta et al., Essential role of the glycosyltransferase sxc/Ogt in polycomb repression. Science. Jul. 3, 2009;325(5936):93-6. Epub May 28, 2009.

(56) References Cited

OTHER PUBLICATIONS

Gao et al., Dynamic O-glycosylation of nuclear and cytosolic proteins: cloning and characterization of a neutral, cytosolic beta-N-acetylglucosaminidase from human brain. J Biol Chem. Mar. 30, 2001;276(13):9838-45. Epub Jan. 8, 2001.
Gloster et al., Glycosidase inhibition: assessing mimicry of the transition state. Org Biomol Chem. Jan. 21, 2010;8(2):305-20. Epub Nov. 5, 2009.
Gloster et al., Hijacking a biosynthetic pathway yields a glycosyltransferase inhibitor within cells. Nat Chem Biol. Mar. 2011;7(3):174-81. Epub Jan. 23, 2011.
Goldberg et al., Posttranslational, reversible O-glycosylation is stimulated by high glucose and mediates plasminogen activator inhibitor-1 gene expression and Sp1 transcriptional activity in glomerular mesangial cells. Endocrinology. Jan. 2006;147(1):222-31.
Golks et al., Requirement for O-linked N-acetylglucosaminyltransferase in lymphocytes activation. Embo J. Oct. 17, 2007;26(20):4368-79. Epub Sep. 20, 2007.
Golks et al., The O-linked N-acetylglucosamine modification in cellular signalling and the immune system. 'Protein modifications: beyond the usual suspects' review series. EMBO Rep. Aug. 2008;9(8):748-53. Epub Jul. 11, 2008.
Good et al., Hydrogen ion buffers for biological research. Biochemistry. Feb. 1966;5(2):467-77.
Goodford, A computational procedure for determining energetically favorable binding sites on biologically important macromolecules. J Med Chem. Jul. 1985;28(7):849-57.
Goodsell et al., Automated docking of substrates to proteins by simulated annealing. Proteins. 1990;8(3):195-202.
Gorodkin et al., Displaying the information contents of structural RNA alignments: the structure logos. Comput Appl Biosci. Dec. 1997;13(6):583-6.
Gosselin et al., A continuous spectrophotometric assay for glycosyltransferases. Anal Biochem. Jul. 1994;220(1):92-7.
Griffith et al., O-linked N-acetylglucosamine levels in cerebellar neurons respond reciprocally to pertubations of phosphorylation. Eur J Biochem. Jun. 1999;262(3):824-31.
Gross et al., A strategy to discover inhibitors of O-linked glycosylation. J Am Chem Soc. Jan. 16, 2008;130(2):440-1. Epub Dec. 20, 2007.
Gross et al., Discovery of O-GlcNAc transferase inhibitors. J Am Chem Soc. Oct. 26, 2005;127(42):14588-9.
Guan et al., Small interfering RNA-mediated Polo-like kinase 1 depletion preferentially reduces the survival of p53-defective, oncogenic transformed cells and inhibits tumor growth in animals. Cancer Res. Apr. 1, 2005;65(7):2698-704.
Ha et al., The 1.9 A crystal structure of *Escherichia coli* MurG, a membrane-associated glycosyltransferase involved in peptidoglycan biosynthesis. Protein Sci. Jun. 2000;9(6):1045-52.
Hadjuch et al., A convenient synthesis of the C-1-phosphonate analogue of UDP-GlcNAc and its evaluation as an inhibitor of O-linked GlcNAc transferase (OGT). Carbohydr Res. Feb. 4, 2008;343(2):189-95. Epub Nov. 1, 2007.
Hagen et al., All in the family: the UDP-GalNAc:polypeptide N-acetylgalactosaminyltransferases. Glycobiology. 2003;13(1):1R-16R.
Halgren et al., Glide: a new approach for rapid, accurate docking and scoring. 2. Enrichment factors in database screening. J Med Chem. Mar. 25, 2004;47(7):1750-9.
Haltiwanger et al., Enzymatic addition of O-GlcNAc to nuclear and cytoplasmic proteins. Identification of a uridine diphospho-N-acetylglucosamine:peptide beta-N-acetylglucosaminyltransferase. J Biol Chem. Feb. 15, 1990;265(5):2563-8.
Haltiwanger et al., Glycosylation of nuclear and cytoplasmic proteins. Purification and characterization of a uridine diphospho-N-acetylglucosamine:polypeptide beta-N-acetylglucosaminyltransferase. J Biol Chem. May 5, 1992;267(13):9005-13.
Haltiwanger et al., Modulation of O-linked N-acetylglucosamine levels on nuclear and cytoplasmic proteins in vivo using the peptide O-GlcNAc-beta-N-acetylglucosaminidase inhibitor O-(2-acetamido-2-deoxy-D-glucopyranosylidene)amino-N-phenylcarbamate. J Biol Chem. Feb. 6, 1998;273(6):3611-7.
Hamanaka et al., Polo-like kinase is a cell cycle-regulated kinase activated during mitosis. J Biol Chem. Sep. 8, 1995;270(36):21086-91.
Hang et al., Small molecule inhibitors of mucin-type O-linked glycosylation from a uridine-based library. Chem Biol. Mar. 2004;11(3):337-45.
Hanover et al., A *Caenorhabditis elegans* model of insulin resistance: altered macronutrient storage and dauer formation in an OGT-1 knockout. Proc Natl Acad Sci U S A. Aug. 9, 2005;102(32):11266-71. Epub Jul. 28, 2005.
Hanover et al., Mitochondrial and nucleocytoplasmic isoforms of O-linked GlcNAc transferase encoded by a single mammalian gene. Arch Biochem Biophys. Jan. 15, 2003;409(2):287-97.
Hanover, Glycan-dependent signaling: O-linked N-acetylglucosamine FASEB J. Sep. 2001;15(11):1865-76.
Hart et al., Chapter 18. The O-GlcNAc modification. In: Essentials of glycobiology. Varki et al., eds. Cold Spring Harbor Laboratory Press, Cold Spring Harbor, NY. 2009. 21 pages.
Hart et al., Cycling of O-linked beta-N-acetylglucosamine on nucleocytoplasmic proteins. Nature. Apr. 26, 2007;446(7139):1017-22.
Hart et al., O-GlcNAcylation of key nuclear and cytoskeletal proteins: reciprocity with O-phosphorylation and putative roles in protein multimerization. Glycobiology. Oct. 1996;6(7):711-6.
Hart et al., O-linked N-acetylglucosamine: the "yin-yang" of Ser/Thr phosphorylation? Nuclear and cytoplasmic glycosylation. Adv Exp Med Biol. 1995;376:115-23.
Hartweck et al., Two O-linked N-acetylglucosamine transferase genes of *Arabidopsis thaliana* L. Heynh. have overlapping functions necessary for gamete and seed development. Genetics. Jul. 2002;161(3):1279-91.
Helm et al., Identification of active-site inhibitors of MurG using a generalizable, high-throughput glycosyltransferase screen. J Am Chem Soc. Sep. 17, 2003;125(37):11168-9.
Hinou et al., Systematic syntheses and inhibitory activities of bisubstrate-type inhibitors of sialyltransferases. J Org Chem. Jul. 11, 2003;68(14):5602-13.
Holt et al., Erythrocytes contain cytoplasmic glycoproteins. O-linked GlcNAc on Band 4.1. J Biol Chem. Nov. 5, 1987;262(31):14847-50.
Housley et al., A PGC-1alpha-O-GlcNAc transferase complex regulates FoxO transcription factor activity in response to glucose. J Biol Chem. Feb. 20, 2009;284(8):5148-57. Epub Dec. 22, 2008.
Housley et al., O-GlcNAc regulates FoxO activation in response to glucose. J Biol Chem. Jun. 13, 2008;283(24):16283-92. Epub Apr. 17, 2008.
Hu et al., Adenovirus-mediated overexpression of O-GlcNAcase improves contractile function in the diabetic heart. Circ Res. May 13, 2005;96(9):1006-13. Epub Apr. 7, 2005.
Hu et al., Crystal structure of the MurG:UDP-GlcNAc complex reveals common structural principles of a superfamily of glycosyltransferases. Proc Natl Acad Sci U S A. Feb. 4, 2003;100(3):845-9. Epub Jan. 21, 2003.
Hu et al., Identification of selective inhibitors for the glycosyltransferase MurG via high-throughput screening. Chem Biol. May 2004;11(5):703-11.
Huang et al., A Continuous Method for Enzymatic Assay of Sucrose Synthase in the Synthetic Direction. J Agric Food Chem. 1999;47:2746-50.
Hudson et al., Late mitotic failure in mice lacking Sak, a polo-like kinase. Curr Biol. Mar. 20, 2001;11(6):441-6.
Hurtado-Guerrero et al., Molecular mechanisms of O-GlcNAcylation. Curr Opin Struct Biol. Oct. 2008;18(5):551-7. Epub Oct. 6, 2008.
Izumi et al., Bisubstrate analogues as glycosyltransferase inhibitors. Curr Top Med Chem. 2009;9(1):87-105.
Izumi et al., Neutral beta-N-acetylhexosaminidases of rat brain. Purification and enzymatic and immunological characterization. J Biol Chem. Jun. 10, 1983;258(11):6991-9.

(56) References Cited

OTHER PUBLICATIONS

Jackson et al., O-glycosylation of eukaryotic transcription factors: implications for mechanisms of transcriptional regulation. Cell. Oct. 7, 1988;55(1):125-33.
James et al., Flux through the hexosamine pathway is a determinant of nuclear factor kappaB-dependent promoter activation. Diabetes. Apr. 2002;51(4):1146-56.
Jiang et al., A neutral diphosphate mimic crosslinks the active site of human O-GlcNAc transferase. Nat Chem Biol. Nov. 13, 2011;8(1):72-7. doi: 10.1038/nchembio.711. Supplementary Information included.
Jiang et al., A subpopulation of estrogen receptors are modified by O-linked N-acetylglucosamine. J Biol Chem. Jan. 24, 1997;272(4):2421-8.
Jinek et al., The superhelical TPR-repeat domain of O-linked GlcNAc transferase exhibits structural similarities to importin alpha. Nat Struct Mol Biol. Oct. 2004;11(10):1001-7. Epub Sep. 12, 2004.
Jones, A bittersweet modification: O-GlcNAc and cardiac dysfunction. Circ Res. May 13, 2005;96(9):925-6.
Juang et al., Phosphorylation and O-linked glycosylation of Elf-1 leads to its translocation to the nucleus and binding to the promoter of the TCR zeta-chain. J Immunol. Mar. 15, 2002;168(6):2865-71.
Kamemura et al., Dynamic interplay between O-glycosylation and O-phosphorylation of nucleocytoplasmic proteins: alternative glycosylation/phosphorylation of THR-58, a known mutational hot spot of c-Myc in lymphomas, is regulated by mitogens. J Biol Chem. May 24, 2002;277(21):19229-35. Epub Mar. 19, 2002.
Kelly et al., RNA polymerase II is a glycoprotein. Modification of the COOH-terminal domain by O-GlcNAc. J Biol Chem. May 15, 1993;268(14):10416-24.
Khidekel et al., Probing the dynamics of O-GlcNAc glycosylation in the brain using quantitative proteomics. Nat Chem Biol. Jun. 2007;3(6):339-48. Epub May 13, 2007.
Khraltsova et al., An enzyme-linked lectin assay for alpha1,3-galactosyltransferase. Anal Biochem. May 1, 2000;280(2):250-7.
Kiefer et al., The SWISS-MODEL Repository and associated resources. Nucleic Acids Res. Jan. 2009;37(Database issue):D387-92. Epub Oct. 18, 2008.
Kiessling et al., Chemical approaches to glycobiology. Annu Rev Biochem. 2010;79:619-53.
Kim et al., An O-GlcNAcase-specific inhibitor and substrate engineered by the extension of the N-acetyl moiety. J Am Chem Soc. Apr. 5, 2006;128(13):4234-5.
King et al., Cytokeratin 13 contains O-glycosidically linked N-acetylglucosamine residues. J Biol Chem. Aug. 25, 1989;264(24):14022-8.
Klein et al., O-linked N-acetylglucosamine modification of insulin receptor substrate-1 occurs in close proximity to multiple SH2 domain binding motifs. Mol Cell Proteomics. Dec. 2009;8(12):2733-45. Epub Aug. 11, 2009.
Konrad et al., Alloxan is an inhibitor of the enzyme O-linked N-acetylglucosamine transferase. Biochem Biophys Res Commun Apr. 26, 2002;293(1):207-12.
Konrad et al., The role of O-linked protein glycosylation in beta-cell dysfunction. Int J Mol Med. Nov. 2002;10(5):535-9.
Koresawa et al., High-throughput screening with quantitation of ATP consumption: a universal non-radioisotope, homogeneous assay for protein kinase. Assay Drug Dev Technol. Apr. 2004;2(2):153-60.
Kozarsky et al., Use of a mutant cell line to study the kinetics and function of O-linked glycosylation of low density lipoprotein receptors. Proc Natl Acad Sci U S A. Jun. 1988;85(12):4335-9.
Kreppel et al., Dynamic glycosylation of nuclear and cytosolic proteins. Cloning and characterization of a unique O-GlcNAc transferase with multiple tetratricopeptide repeats. J Biol.Chem. Apr. 4, 1997;272(14):9308-15.
Kreppel et al., Regulation of a cytosolic and nuclear O-GlcNAc transferase. Role of the tetratricopeptide repeats. J Biol Chem. Nov. 5, 1999;274(45):32015-22.
Kuntz et al., A geometric approach to macromolecule-ligand interactions. J Mol Biol. Oct. 25, 1982;161(2):269-88.

Lairson et al., Glycosyltransferases: structures, functions, and mechanisms. Annu Rev Biochem. 2008;77:521-55.
Lamarre-Vincent et al., Dynamic glycosylation of the transcription factor CREB: a potential role in gene regulation. J Am Chem Soc. Jun. 4, 2003;125(22):6612-3.
Lane et al., Antibody microinjection reveals an essential role for human polo-like kinase 1 (Plk1) in the functional maturation of mitotic centrosomes. J Cell Biol. Dec. 1996;135(6 Pt 2):1701-13.
Lazarus et al., Mutational analysis of the catalytic domain of O-linked N-acetylglucosaminyl transferase. J Biol Chem. Oct. 21, 2005;280(42):35537-44. Epub Aug. 16, 2005.
Lazarus et al., Structure of human O-GlcNAc transferase and its complex with a peptide substrate. Nature. Jan. 27, 2011;469(7331):564-7. Epub Jan. 16, 2011.
Leavy et al., A high-throughput assay for O-GlcNAc transferase detects primary sequence preferences in peptide substrates. Bioorg Med Chem Lett. Jul. 15, 2007;17(14):3851-4. Epub May 10, 2007.
Lee et al., A potent and highly selective inhibitor of human alpha-1,3-fucosyltransferase via click chemistry. J Am Chem Soc. Aug. 13, 2003;125(32):9588-9.
Lee et al., Alloxan is an inhibitor of O-GlcNAc-selective N-acetyl-beta-D-glucosaminidase. Biochem Biophys Res Commun. Dec. 1, 2006;350(4):1038-43. Epub Oct. 6, 2006.
Lefebvre et al., Effect of okadaic acid on O-linked N-acetylglucosamine levels in a neuroblastoma cell line. Biochim Biophys Acta. Oct. 18, 1999;1472(1-2):71-81.
Lefebvre et al., Evidence of a balance between phosphorylation and O-GlcNAc glycosylation of Tau proteins—a role in nuclear localization. Biochim Biophys Acta. Jan. 20, 2003;1619(2):167-76.
Lefebvre et al., Identification of N-acetyl-d-glucosamine-specific lectins from rat liver cytosolic and nuclear compartments as heat-shock proteins. Biochem J. Nov. 15, 2001;360(Pt 1):179-88.
Lefebvre et al., The tumor suppressor HIC1 (hypermethylated in cancer 1) is O-GlcNAc glycosylated. Eur J Biochem. Oct. 2004;271(19):3843-54.
Lehman et al., A single nucleotide polymorphism in MGEA5 encoding O-GlcNAc-selective N-acetyl-beta-D glucosaminidase is associated with type 2 diabetes in Mexican Americans. Diabetes. Apr. 2005;54(4):1214-21.
Li et al., Function of polo-like kinase 3 in NF-kappaB-mediated proapoptotic response. J Biol Chem. Apr. 29, 2005;280(17):16843-50. Epub Jan. 25, 2005.
Li et al., SAK, a new polo-like kinase, is transcriptionally repressed by p53 and induces apoptosis upon RNAi silencing. Neoplasia. Apr. 2005;7(4):312-23.
Liu et al., Glucose stimulates protein modification by O-linked GlcNAc in pancreatic beta cells: linkage of O-linked GlcNAc to beta cell death. Proc Natl Acad Sci U S A. Mar. 14, 2000;97(6):2820-5.
Liu et al., O-GlcNAcylation regulates phosphorylation of tau: a mechanism involved in Alzheimer's disease. Proc Natl Acad Sci U S A. Jul. 20, 2004;101(29):10804-9. Epub Jul. 12, 2004.
Liu et al., Polo-like kinase (Plk)1 depletion induces apoptosis in cancer cells. Proc Natl Acad Sci U S A. May 13, 2003;100(10):5789-94. Epub May 5, 2003.
Liu et al., The Synthesis and Characterization of a Helical Miniature Protein Mimicking the OGT Active Domain. Int J Pept Res Ther. 2006;12(3):237-41.
Love et al., Dynamic O-GlcNAc cycling at promoters of *Caenorhabditis elegans* genes regulating longevity, stress, and immunity. Proc Natl Acad Sci U S A. Apr. 20, 2010;107(16):7413-8. Epub Apr. 5, 2010.
Love et al., Mitochondrial and nucleocytoplasmic targeting of O-linked GlcNAc transferase. J Cell Sci. Feb. 15, 2003;116(Pt 4):647-54.
Love et al., The hexosamine signaling pathway: deciphering the "O-GlcNAc code".Sci STKE. Nov. 29, 2005;2005(312):re13.
Lowery et al., Structure and function of Polo-like kinases. Oncogene. Jan. 10, 2005;24(2):248-59.
Lowery et al., Transcreener: screening enzymes involved in covalent regulation. Expert Opin Ther Targets. Feb. 2006;10(1):179-90.
Lubas et al., Analysis of nuclear pore protein p62 glycosylation. Biochemistry. Feb. 7, 1995;34(5):1686-94.

(56) References Cited

OTHER PUBLICATIONS

Lubas et al., Functional expression of O-linked GlcNAc transferase. Domain structure and substrate specificity. J Biol Chem. Apr. 14, 2000;275(15):10983-8.

Lubas et al., O-Linked GlcNAc transferase is a conserved nucleocytoplasmic protein containing tetratricopeptide repeats. J Biol Chem. Apr. 4, 1997;272(14):9316-24.

Ma et al., Drug targeting *Mycobacterium tuberculosis* cell wall synthesis: genetics of dTDP-rhamnose synthetic enzymes and development of a microtiter plate-based screen for inhibitors of conversion of dTDP-glucose to dTDP-rhamnose. Antimicrob Agents Chemother. May 2001;45(5):1407-16.

Ma et al., Role of Plk2 (Snk) in mouse development and cell proliferation. Mol Cell Biol. Oct. 2003;23(19):6936-43.

MacAuley et al., Increasing O-GlcNAc levels: an overview of small-molecule inhibitors of O-GlcNAcase. Biochim Biophys Acta. Feb. 2010;1800(2):107-21. Epub Aug. 4, 2009.

MacAuley et al., O-GlcNAcase uses substrate-assisted catalysis: kinetic analysis and development of highly selective mechanism-inspired inhibitors. J Biol Chem. Jul. 8, 2005;280(27):25313-22. Epub Mar. 28, 2005.

MacMillan et al., Comparative expression of the mitotic regulators SAK and PLK in colorectal cancer. Ann Surg Oncol. Oct. 2001;8(9):729-40.

Majumdar et al., Insulin stimulates and diabetes inhibits O-linked N-acetylglucosamine transferase and O-glycosylation of Sp1. Diabetes. Dec. 2004;53(12):3184-92.

Malinka et al., 2-Substituted-3-oxoisothiazolo[5,4-b]pyridines as potential central nervous system and antimycobacterial agents. Farmaco. Jul. 30, 1998;53(7):504-12.

Marshall et al., Discovery of a metabolic pathway mediating glucose-induced desensitization of the glucose transport system. Role of hexosamine biosynthesis in the induction of insulin resistance. J Biol Chem. Mar. 15, 1991;266(8):4706-12.

Marshall et al., Enhanced expression of uridine diphosphate-N-acetylglucosaminyl transferase (OGT) in a stable, tetracycline-inducible HeLa cell line using histone deacetylase inhibitors: kinetics of cytosolic OGT accumulation and nuclear translocation. Anal Biochem. Aug. 15, 2003;319(2):304-13.

Marshall et al., Measurement of UDP-N-acetylglucosaminyl transferase (OGT) in brain cytosol and characterization of anti-OGT antibodies. Anal Biochem. Mar. 15, 2003;314(2):169-79.

Martin et al., 3D database searching in drug design. J Med Chem. Jun. 12, 1992;35(12):2145-54.

Martinez-Fleites et al., Structural analyses of enzymes involved in the O-GlcNAc modification. Biochim Biophys Acta. Feb. 2010;1800(2):122-33. Epub Jul. 30, 2009.

Martinez-Fleites et al., Structure of an O-GlcNAc transferase homolog provides insight into intracellular glycosylation. Nat Struct Mol Biol. Jul. 2008;15(7):764-5. Epub Jun. 8, 2008.

Martinez-Fleites et al., Structure of an O-GlcNAc transferase homolog provides insight into intracellular glycosylation. Nat Struct Mol Biol. Jul. 2008;15(7):764-5. Epub Jun. 8, 2008. Supplementary Information.

Mathis, Probing molecular interactions with homogeneous techniques based on rare earth cryptates and fluorescence energy transfer. Clin Chem. Sep. 1995;41(9):1391-7.

McCoy et al., Phaser crystallographic software. J Appl Crystallogr. Aug. 1, 2007;40(Pt 4):658-674. Epub Jul. 13, 2007.

McCoy, Solving structures of protein complexes by molecular replacement with Phaser. Acta Crystallogr D Biol Crystallogr. Jan. 2007;63(Pt 1):32-41. Epub Dec. 13, 2006.

Medina et al., SV40 large T antigen is modified with O-linked N-acetylglucosamine but not with other forms of glycosylation. Glycobiology. Apr. 1998;8(4):383-91.

Meikrantz et al., Nuclear localization of an O-glycosylated protein phosphotyrosine phosphatase from human cells. J Cell Sci. Mar. 1991;98 ( Pt 3):303-7.

Miranker et al., Functionality maps of binding sites: a multiple copy simultaneous search method. Proteins. 1991;11(1):29-34.

Mizanur et al., One-step synthesis of labeled sugar nucleotides for protein O-GlcNAc modification studies by chemical function analysis of an archaeal protein. J Am Chem Soc. Jan. 26, 2005;127(3):836-7.

Moura et al., Large scale comparative codon-pair context analysis unveils general rules that fine-tune evolution of mRNA primary structure. PLoS One. Sep. 5, 2007;2(9):e847.

Navaza et al., AmoRE: an Automated Package for Molecular Replacement. Acta Cryst. 1994;A50:157-63.

Navia et al., Use of structural information in drug design. Curr Opin Struct Biol. 1992;2:202-10.

Nishibata et al., Automatic Creation of Drug Candidate Structures Based on Receptor Structure. Starting Point for Artificial Lead Generation. Tetrahedron. 1991;47(43):8985-90.

Nishikata et al., A phosphotyrosine-containing quenched fluorogenic peptide as a novel substrate for protein tyrosine phosphatases. Biochem J. 1999;343:385-91.

Nishikata et al., Continuous assay of protein tyrosine phosphatases based on fluorescence resonance energy transfer. Biochimie. Jul. 2006;88(7):879-86. Epub Feb. 28, 2006.

Nishio et al., Acylation and Alkoxycarbonylation of Benzoxazoline-2-thione and Benzothiazoline2-thione. Heterocycles. 2004;62(1):313-324.

Nolte et al., Human O-GlcNAc transferase (OGT): genomic structure, analysis of splice variants, fine mapping in Xq13.1. Mamm Genome. Jan. 2002;13(1):62-4.

Novak et al., Heterogeneity of O-glycosylation in the hinge region of human IgA1. Mol Immunol. Dec. 2000;37(17):1047-56.

O'Donnell et al., Ogt-dependent X-chromosome-linked protein glycosylation is a requisite modification in somatic cell function and embryo viability. Mol Cell Biol. Feb. 2004;24(4):1680-90.

Ogawa et al., Profiling terminal N-acetyllactosamines of glycans on mammalian cells by an immuno-enzymatic assay. Glycoconj J. Dec. 2006;23(9):663-74. Epub Nov. 18, 2006.

Ohn et al., A functional RNAi screen links O-GlcNAc modification of ribosomal proteins to stress granule and processing body assembly. Nat Cell Biol. Oct. 2008;10(10):1224-31. Epub Sep. 14, 2008.

Olah et al., Strategies for compound selection. Curr Drug Discov Technol. Oct. 2004;1(3):211-20.

Painter et al., Optimal description of a protein structure in terms of multiple groups undergoing TLS motion. Acta Crystallogr D Biol Crystallogr. Apr. 2006;62(Pt 4):439-50. Epub Mar. 18, 2006.

Painter et al., TLSMD web server for the generation of multi-group TLS models. J Appl Cryst. 2006;39:109-11.

Palcic et al., Assays for Glycosyltransferases. Trends in Glycosci and Glycotechnol. 2001;13(72):361-70.

Pape et al., HKL2MAP: a graphical user interface for macromolecular phasing with SHELX programs. J Appl Cryst. 2004;37:843-44.

Parker et al., Insulin resistance of glycogen synthase mediated by o-linked N-acetylglucosamine. J Biol Chem. Mar. 21, 2003;278(12):10022-7. Epub Jan. 1, 2003.

Patti et al., Activation of the Hexosamine Pathway by Glucosamine in Vivo Induces Insulin Resistance of Early Postreceptor Insulin Signaling Events in Skeletal Muscle. Diabetes 1999 v48 p. 1562-1571.

Peitsch, Protein modeling by E-mail. Bio/Technol. 1995;13:658-60.

Pesnot et al., Structural and mechanistic basis for a new mode of glycosyltransferase inhibition. Nat Chem Biol. May 2010;6(5):321-3. Epub Apr. 4, 2010.

Potterton et al., Developments in the CCP4 molecular-graphics project. Acta Crystallogr D Biol Crystallogr. Dec. 2004;60(Pt 12 Pt 1):2288-94. Epub Nov. 26, 2004.

Poznanskaya et al., New derivatives of benzoxazolinones and benzoxazolinethiones. I. Synthesis and acylating activity of N-aryloxycarbony 1-2-benzoxazolinones. Khimiya Geterotsiklicheskikh Soedinenii. 1969;6:965-7. Russian. Retrieved from DB ACS on STN CA: 72:121409, compounds with RN 27087-35-0, 27087-36-1, 27087-37-2, 27087-38-3, 27087-39-4, 27087-40-7, 27087-41-8, 27087-42-9, 27087-43-0.

Pratt et al., Deconvoluting the functions of polypeptide N-alpha-acetylgalactosaminyltransferase family members by glycopeptide substrate profiling. Chem Biol. Jul. 2004;11(7):1009-16.

(56) References Cited

OTHER PUBLICATIONS

Qiu et al., Expressions of polypeptide: N-acetylgalactosaminyltransferase in leukemia cell lines during 1,25-dihydroxyvitamin D3 induced differentiation. Glycoconj J. Nov. 2006;23(7-8):575-84.

Reason et al., Localization of O-GlcNAc modification on the serum response transcription factor. J Biol Chem. Aug. 25, 1992;267(24):16911-21.

Reaven, Pathophysiology of insulin resistance in human disease. Physiol Rev. Jul. 1995;75(3):473-86.

Rempel et al., Covalent inhibitors of glycosidases and their applications in biochemistry and biology. Glycobiology. Aug. 2008;18(8):570-86. Epub May 22, 2008.

Rex-Mathes et al., Immunological detection of O-GlcNAc. Methods Mol Biol. 2002;194:73-87.

Rodems et al., A FRET-based assay platform for ultra-high density drug screening of protein kinases and phosphatases. Assay Drug Dev Technol. Nov. 2002;1(1 Pt 1):9-19.

Rogawski et al., The neuropharmacological basis for the use of memantine in the treatment of Alzheimer's disease. CNS Drug Rev. 2003 Fall;9(3):275-308.

Roquemore et al., Detection of O-linked N-acetylglucosamine (O-GlcNAc) on cytoplasmic and nuclear proteins. Methods Enzymol. 1994;230:443-60.

Roquemore et al., Dynamic O-GlcNAcylation of the small heat shock protein alpha B-crystallin. Biochemistry. Mar. 19, 1996;35(11):3578-86.

Saotome et al., Combinatorial library of five-membered iminocyclitol and the inhibitory activities against glyco-enzymes. Chem Biol. Nov. 2001;8(11):1061-70.

Sawhney et al., Bioerodible Hydrogels Based on Photopolymerized Poly(ethylene glycol)-co-poly(α-hydroxy acid) Diacrylate Macromers. Macromolecules. 1993;26:581-587.

Schneider et al., Sequence logos: a new way to display consensus sequences. Nucleic Acids Res. Oct. 25, 1990;18(20):6097-100.

Schuttelkopf et al., PRODRG: a tool for high-throughput crystallography of protein-ligand complexes. Acta Crystallogr D Biol Crystallogr. Aug. 2004;60(Pt 8):1355-63. Epub Jul. 21, 2004.

Seidler et al., Identification and prediction of promiscuous aggregating inhibitors among known drugs. J Med Chem. Oct. 9, 2003;46(21):4477-86.

Shaw et al., Regulation of specific DNA binding by p53: evidence for a role for O-glycosylation and charged residues at the carboxy-terminus. Oncogene. Feb. 15, 1996;12(4):921-30.

Shi et al., Protein O-fucosyltransferase 1 is an essential component of Notch signaling pathways. Proc Natl Acad Sci U S A. Apr. 29, 2003;100(9):5234-9. Epub Apr. 15, 2003.

Sim et al., Benzylidene rhodanines as novel inhibitors of UDP-N-acetylmuramate/L-alanine ligase. Bioorg Med Chem Lett. Feb. 25, 2002;12(4):697-9.

Sinclair et al., Drosophila O-GlcNAc transferase (OGT) is encoded by the Polycomb group (PcG) gene, super sex combs (sxc). Proc Natl Acad Sci U S A. Aug. 11, 2009;106(32):13427-32. Epub Jul. 28, 2009.

Skropeta et al., Asymmetric synthesis and affinity of potent sialyltransferase inhibitors based on transition-state analogues. Glycoconj J. 2004;21(5):205-19.

Smith et al., Malignant transformation of mammalian cells initiated by constitutive expression of the polo-like kinase. Biochem Biophys Res Commun. May 19, 1997;234(2):397-405.

Soltero-Higgin et al., Identification of inhibitors for UDP-galactopyranose mutase. J Am Chem Soc. Sep. 1, 2004;126(34):10532-3.

Tai et al., Parallel identification of O-GlcNAc-modified proteins from cell lysates. J Am Chem Soc. Sep. 1, 2004;126(34):10500-1.

Tats et al., Preferred and avoided codon pairs in three domains of life. BMC Genomics. Oct. 8, 2008;9:463.

Tenno et al., Initiation of protein O glycosylation by the polypeptide GalNAcT-1 in vascular biology and humoral immunity. Mol Cell Biol. Dec. 2007;27(24):8783-96. Epub Oct. 8, 2007.

Toleman et al., Characterization of the histone acetyltransferase (HAT) domain of a bifunctional protein with activable O-GlcNAcase and Hat activities. J Biol Chem. Dec. 17, 2004;279(51):53665-73. Epub Oct. 12, 2004.

Topaz et al., Absence of intraepidermal glycosyltransferase ppGalNac-T3 expression in familial tumoral calcinosis. Am J Dermatopathol. Jun. 2005;27(3):211-5.

Torres et al., Topography and polypeptide distribution of terminal N-acetylglucosamine residues on the surfaces of intact lymphocytes. Evidence for O-linked GlcNAc. J Biol Chem. Mar. 10, 1984;259(5):3308-17.

Trunkfield et al, Inhibition of Escherichia coli glycosyltransferase MurG and Mycobacterium tuberculosis Gal transferase by uridine-linked transition state mimics. Bioorg Med Chem. Apr. 1, 2010;18(7):2651-63. Epub Feb. 19, 2010.

Tsokos et al., Activation of the Ets transcription factor Elf-1 requires phosphorylation and glycosylation: defective expression of activated Elf-1 is involved in the decreased TCR zeta chain gene expression in patients with systemic lupus erythematosus. Ann N Y Acad Sci. Apr. 2003;987:240-5.

Turner et al., Cytologic assessment of nuclear and cytoplasmic O-linked N-acetylglucosamine distribution by using anti-streptococcal monoclonal antibodies. Proc Natl Acad Sci U S A. Aug. 1990;87(15):5608-12.

Vocadlo et al., A chemical approach for identifying O-GlcNAc-modified proteins in cells. Proc Natl Acad Sci U S A. Aug. 5, 2003;100(16):9116-21. Epub Jul. 21, 2003.

Vocadlo et al., Mechanistic insights into glycosidase chemistry. Curr Opin Chem Biol. Oct. 2008;12(5):539-55.

Von Ahsen et al., High-throughput screening for kinase inhibitors. Chembiochem. Mar. 2005;6(3):481-90.

Vosseller et al., Elevated nucleocytoplasmic glycosylation by O-GlcNAc results in insulin resistance associated with defects in Akt activation in 3T3-L1 adipocytes. Proc Natl Acad Sci U S A. Apr. 16, 2002;99(8):5313-8.

Vosseller et al., O-linked N-acetylglucosamine proteomics of postsynaptic density preparations using lectin weak affinity chromatography and mass spectrometry. Mol Cell Proteomics. May 2006;5(5):923-34. Epub Feb. 1, 2006.

Wagner et al., Glycosyltransferases and their assays. Chembiochem. Sep. 24, 2010;11(14):1939-49.

Walgren et al., High glucose and insulin promote O-GlcNAc modification of proteins, including alpha-tubulin. Am J Physiol Endocrinol Metab. Feb. 2003;284(2):E424-34. Epub Oct. 22, 2002.

Wang et al., A search for pyrophosphate mimics for the development of substrates and inhibitors of glycosyltransferases. Bioorg Med Chem. Apr. 1997;5(4):661-72.

Wang et al., Enrichment and site mapping of O-linked N-acetylglucosamine by a combination of chemical/enzymatic tagging, photochemical cleavage, and electron transfer dissociation mass spectrometry. Mol Cell Proteomics. Jan. 2010;9(1):153-60. Epub Aug. 19, 2009.

Wang et al., Extensive crosstalk between O-GlcNAcylation and phosphorylation regulates cytokinesis. Sci Signal. Jan. 12, 2010;3(104):ra2.

Weichert et al., Polo-like kinase isoform expression is a prognostic factor in ovarian carcinoma. Br J Cancer. Feb. 23, 2004;90(4):815-21.

Weichert et al., Polo-like kinase isoforms in breast cancer: expression patterns and prognostic implications. Virchows Arch. Apr. 2005;446(4):442-50. Epub Mar. 23, 2005.

Wells et al., A role for N-acetylglucosamine as a nutrient sensor and mediator of insulin resistance. Cell Mol Life Sci. Feb. 2003;60(2):222-8.

Wells et al., Dynamic O-glycosylation of nuclear and cytosolic proteins: further characterization of the nucleocytoplasmic beta-N-acetylglucosaminidase, O-GlcNAcase. J Biol Chem. Jan. 18, 2002;277(3):1755-61.

Wells et al., Glycosylation of nucleocytoplasmic proteins: signal transduction and O-GlcNAc. Science. Mar. 23, 2001;291(5512):2376-8.

(56) References Cited

OTHER PUBLICATIONS

Wells et al., Mapping sites of O-GlcNAc modification using affinity tags for serine and threonine post-translational modifications. Mol Cell Proteomics. Oct. 2002;1(10):791-804.

Wells et al., O-GlcNAc transferase is in a functional complex with protein phosphatase 1 catalytic subunits. J Biol Chem. Sep. 10, 2004;279(37):38466-70. Epub Jul. 7, 2004.

Wesche et al., High throughput screening for protein kinase inhibitors. Comb Chem High Throughput Screen. Mar. 2005;8(2):181-95.

Wilen et al., Strategies in Optical Resolutions. Tetrahedron. 1977;33:2725-36.

Wilen, Tables of Resolving Agents and Optical Resolutions. E.L. Eliel, ed. Universtify of Notre Dame Press, Notre Dame, IN. 1972:268-98.

Wongkongkatep et al., Label-free, real-time glycosyltransferase assay based on a fluorescent artificial chemosensor. Angew Chem Int Ed Engl. Jan. 16, 2006;45(4):665-8.

Wrabl et al., Homology between O-linked GlcNAc transferases and proteins of the glycogen phosphorylase superfamily. J Mol Biol. Nov. 30, 2001;314(3):365-74.

Xu et al., A bioluminescence resonance energy transfer (BRET) system: application to interacting circadian clock proteins. Proc Natl Acad Sci U S A. Jan. 5, 1999;96(1):151-6.

Yang et al., Modification of p53 with O-linked N-acetylglucosamine regulates p53 activity and stability. Nat Cell Biol. Oct. 2006;8(10):1074-83. Epub Sep. 10, 2006. Supplementary Information included.

Yang et al., O-linkage of N-acetylglucosamine to Sp1 activation domain inhibits its transcriptional capability. Proc Natl Acad Sci U S A. Jun. 5, 2001;98(12):6611-6. Epub May 22, 2001.

Yang et al., Phosphoinositide signalling links O-GlcNAc transferase to insulin resistance. Nature. Feb. 21, 2008;451(7181):964-9.

Yang et al., Recruitment of O-GlcNAc transferase to promoters by corepressor mSin3A: coupling protein O-GlcNAcylation to transcriptional repression. Cell. Jul. 12, 2002;110(1):69-80.

Zachara et al., O-GlcNAc a sensor of cellular state: the role of nucleocytoplasmic glycosylation in modulating cellular function in response to nutrition and stress. Biochim Biophys Acta. Jul. 6, 2004;1673(1-2):13-28.

Zachara et al., The emerging significance of O-GlcNAc in cellular regulation. Chem Rev. Feb. 2002;102(2):431-8.

Zhang et al., A Modified Coupled Enzyme Method for O-linked GlcNAc Transferase Activity Assay. Biol Proced Online. Dec. 3, 2009;11:170-83.

Zhang et al., O-GlcNAc modification is an endogenous inhibitor of the proteasome. Cell. Dec. 12, 2003;115(6):715-25.

\* cited by examiner general substrate for ppGalNAcTs selective substrate for ppGalNAcT1 ppGalNAcT2 crystals grown
in the absence of small molecule ppGalNAcT2 crystals grown
in the presence of small molecule

METHODS AND COMPOSITIONS FOR DETECTING AND MODULATING O-GLYCOSYLATION

RELATED APPLICATIONS

This application is a divisional application of and claims priority under 35 U.S.C. §120 to U.S. Application, U.S. Ser. No. 12/664,559, filed Jul. 21, 2010, now U.S. Pat. No. 8,524,444, which is a national stage filing under 35 U.S.C. §371 of international application, PCT/US2008/007410, filed Jun. 13, 2008, which claims the benefit under 35 U.S.C §119(e) of U.S. provisional patent application, U.S. Ser. No. 60/934,803, filed Jun. 15, 2007, the entire contents of each of which is incorporated herein by reference.

GOVERNMENT SUPPORT

This invention was made with government support under grant number AI44854 awarded by the National Institutes of Health. The government has certain rights in the invention.

FIELD OF THE INVENTION

The invention relates, in part, to methods and products for assessing O-glycosylation of polypeptides and for identifying compounds that modify O-glycosylation of polypeptides. The invention also relates, in part, to O-glycosylation inhibitor compounds that have been identified and the use of such compounds for treatment of O-glycosylation-associated disorders such as neurodegeneration, insulin resistance, diabetes, and complications of diabetes such as nephropathy, microvascular damage, and endothelial dysfunction. The invention also relates in part to assays and substrate polypeptides that are useful for identifying and testing candidate compounds to determine their effect on modulating glycosylation of polypeptides.

BACKGROUND OF THE INVENTION

The hexosamine biosynthetic pathway (HSP) is a minor branch of the glycolytic pathway, diverting 3-5% of cellular glucose toward the synthesis of UDP-GlcNAc, which is either transported to the golgi and used in the synthesis of complex glycans or remains in the cytoplasm where it is the obligatory substrate for O-GlcNAc Transferase (OGT). OGT is the sole known enzyme to catalyze the transient glycosylation of serine and threonine residues on many nuclear and cytoplasmic proteins (termed O-GlcNAcylation). This post-translational modification is dynamic and is a general method, like protein phosphorylation, of signal transduction. There are also other glycosylating enzymes that post-translationally modify molecules in the body.

Excess flux through the HSP has been implicated in both early (insulin resistance) and late (nephropathy, microvascular damage) stages in the course of diabetes mellitus, both in vivo and in vitro. Diabetes involves a deficiency in the availability and/or utilization of insulin. Insulin is a hormone produced by the pancreas and is necessary for cells to utilize glucose. Insulin resistance is a condition in which muscle, fat, and liver cells do not use insulin properly. As a result, the pancreas produces more insulin, which also cannot be properly used. Eventually, the pancreas cannot keep up with the body's need for insulin, and excess glucose builds up in the bloodstream. Thus, in insulin resistance, there may be high levels of blood glucose and high levels of insulin circulating in the bloodstream at the same time.

Experiments have shown that insulin resistance due to increased hexosamine flux is caused by hyper O-GlcNAcylation. Diabetics have increased production of two adipokines directly responsible for vascular injury, plasminogen activator inhibitor-1 (PAI-1) and transforming growth factor $\beta_1$ (TGF-$\beta$1). Transcription of both of these proteins is decreased in cell culture when levels of O-GlcNAcylation were decreased. The molecular mechanism for this is known; increased transcription is mediated by the O-GlcNAcylation state of the transcription factor Sp1. OGT activity and levels of O-GlcNAcylation and the activity of additional glycosylating enzymes have also been implicated in other disease states, such as Alzheimer's disease and cancer.

The ppGalNAcT family of glycosyltransferases initiates core-type O-glycan formation, that may be elaborated further by glycan linkages, contributing to selectin ligand-dependent control of leukocyte trafficking, regulation of CD8+ T-cell aoptosis, and sensitivity to colitis and preventing the onset of Tn syndrome. The prototype ppGalNACT family member is ppGalNAcT-1, which is expressed at high levels in most tissues and cell types. Loss of ppGalNAcT-1 activity in a mouse model resulted in bleeding disorder and impaired IgG production. ppGalNAcT-1 has been shown to support normal homeostatic physiology and inflammatory response [(Term et al., Mol Cell Biol 27: 8783-8796 (2007)].

SUMMARY OF THE INVENTION

The invention relates in part, to novel kinetic assays that can be used to detect glycosylation of polypeptides and can be used to screen candidate compounds that modulate (e.g., inhibit or enhance) glycosylation of polypeptides. The invention also includes molecules that include detectably labeled polypeptide substrates that are prepared such that the polypeptide substrate includes a) an O-glycosylation site and b) a specific protease cleavage site positioned in the polypeptide such that the rate of cleavage by the specific protease at the specific protease cleavage site is different when the polypeptide is glycosylated at the O-glycosylation site than when the polypeptide is not glycosylated at the O-glycosylation site. In addition, the detectable label on the polypeptide is positioned in the polypeptide such that a change in the detectable label identifies cleavage of the polypeptide by the specific protease at the specific protease cleavage site. Such polypeptide substrates can be used in assays of the invention that permit detection of O-glycosylation of polypeptides and permit detection of modulation of O-glycosylation by candidate modulatory compounds.

The invention also relates, in part, to newly identified compounds that inhibit O-glycosylation of polypeptides. A number of compounds have now been identified that inhibit O-glycosylation. O-glycosylation is a transient glycosylation of serine and/or threonine residues on nuclear and cytoplasmic proteins that is catalyzed by O-glycosylating enzymes. The newly identified compounds and analogs, derivatives, and variants thereof may be useful for the treatment (including active and/or prophylactic treatment) of diseases and disorders associated with abnormal O-glycosylation. The invention includes, in part, methods for treating diseases and conditions resulting from abnormal O-glycosylation and compositions for treating such diseases and conditions.

The assay also relates, in some aspects, to assays that are useful to identify compounds (e.g., small molecules, etc) that inhibit O-glycosylation activity.

According to one aspect of the invention, isolated molecules are provided. The molecules include a cleavable detectably labeled polypeptide substrate having an O-glycosylation site and a specific protease cleavage site positioned in the polypeptide such that the rate of cleavage by the specific protease at the specific protease cleavage site is different when the polypeptide is glycosylated at the O-glycosylation site than when the polypeptide is not glycosylated at the O-glycosylation site, wherein the detectable label is positioned in the polypeptide such that a change in the detectable label identifies cleavage of the polypeptide by the specific protease at the specific protease cleavage site. In some embodiments, the polypeptide O-glycosylation site is a serine or a threonine residue. In certain embodiments, the serine or threonine is positioned within 1, 2, 3, or 4 amino acids of the protease cleavage site. In some embodiments, protease cleavage site is a single site and there is only one specific protease cleavage site. In some embodiments, the specific protease cleavage site is positioned on the N-terminal side of the O-glycosylation site. In certain embodiments, the specific protease cleavage site is positioned on the C-terminal side of the O-glycosylation site. In some embodiments, the detectable label includes a fluorescent, enzyme, radioactive, metallic, biotin, chemiluminescent, or bioluminescent molecule. In some embodiments, the detectable label is a fluorescent moiety. In certain embodiments, the change in the detectable label comprises a change in fluorescence of the fluorescent moiety. In some embodiments, the detectable label is a FRET donor and a FRET acceptor pair. In some embodiments, the FRET donor and acceptor pair is 7-diethylaminocoumarin-3-carboxylic acid (DEAC) and fluorescein isothiocyanate; [2-(1-sulfonyl-5-naphthyl)-aminoethylamide] EDANS and 4,4-dimethylazobenzene-4'carbonyl (DABCYL); fluorescein isothiocyanate and tetramethylrhodamine (TMR); Tryptophan or tyrosine and dinitrophenyl moieties; or a fluorescein isothiocyanate and a fluorescein isothiocyanate. In some embodiments, the fluorescent moiety is a Cy5.5 emitter or FITC, Texas red, tetramethylrhodamine (TMR), AlexaFluor dyes, HiLyte Fluorophores, or [2-(1-sulfonyl-5-naphthyl)-aminoethylamide] EDANS. In certain embodiments, the polypeptide further comprises a quenching moiety. In some embodiments, the quenching moiety is QXL-520™, BHQ3, Iowa black, 4,4-dimethylazobenzene-4'carbonyl (DABCYL), BHQ1, BHQ10, QXL-570, QXL-620, dinitrophenyl (DNP) containing groups, or QSY-7, 9-21, or 35. In some embodiments, the polypeptide comprises the amino acid sequence set forth as STPVSSANMK (SEQ ID NO:1). In certain embodiments, the polypeptide comprises the amino acid sequence set forth as STPVSFANMK (SEQ ID NO:2). In some embodiments, the polypeptide comprises the amino acid sequence set forth as STPVSRANMK (SEQ ID NO:3). In some embodiments, the polypeptide comprises the amino acid sequence set forth as EYIPTVFDNK (SEQ ID NO:4). In some embodiments, the polypeptide comprises the amino acid sequence set forth as EYRPTVFDNK (SEQ ID NO:5). In certain embodiments, the polypeptide comprises the amino acid sequence set forth as EYIPTVDDNK (SEQ ID NO:6). In some embodiments, the polypeptide comprises the amino acid sequence set forth as EPGPTEAPK (SEQ ID NO:25). In some embodiments, the polypeptide comprises the amino acid sequence set forth as EDAVTPGPK (SEQ ID NO:26). In some embodiments, the protease cleavage site is a proteinase K cleavage site, a trypsin cleavage site, a chymotrypsin cleavage site, a thermolysin cleavage site, Staphylococcal peptidase I cleavage site, Proline-endopeptidase cleavage site, Pepsin cleavage site, Glutamyl endopeptidase cleavage site, Factor Xa cleavage site, Granzyme B Lysyl endopeptidase cleavage site, Asp-N Endopeptidase cleavage site, or enterokinase cleavage site.

According to another aspect of the invention, methods of detecting O-glycosylation of a polypeptide are provided. The methods include (a) contacting a glucosyltransferase enzyme and a UDP-sugar with a molecule that includes a detectably labeled polypeptide having: (i) an O-glycosylation site and (ii) a specific protease cleavage site positioned in the polypeptide such that the rate of cleavage of the polypeptide by the specific protease at the specific protease cleavage site is different when the polypeptide is O-glycosylated at the glycosylation site than when the polypeptide is not O-glycosylated at the glycosylation site, wherein the detectable label is positioned in the polypeptide such that a change in the detectable label identifies cleavage of the polypeptide by the specific protease; (b) adding to the contacted polypeptide the specific protease that cleaves at the specific protease cleavage site of the polypeptide; and (c) monitoring the cleavage of the polypeptide, wherein the rate of cleavage is characteristic of the level of O-glycosylation of the glycosylation site. In some embodiments, the O-glycosylation site comprises a serine or threonine amino acid residue. In certain embodiments, monitoring cleavage comprises monitoring cleavage rate. In some embodiments, wherein the sugar is a UDP-GlcNAc, UDP-GalNAc, UDP-Gal, UDP-Glc, UDP-GlcA (UDP-glucuronic acid), GDP-fucose, CMP-sialic acid, or UDP-xylose. In some embodiments, the glucosyltransferase enzyme is O-GlcNAc transferase; an N-acetylgalactosaminyltransferase; UDP-D-xylose proteoglycan core protein (3 D-xylosyltransferase, UDP GalNAc:polypeptide N-acetylgalactosaminyltransferase, ppGalNAcTs, GDP-fucose protein O-fucosyltransferase 1 (POFUT1), UDP-glucose:protein glucosyltransferase (glycogen initiator synthase or EGF-glucosyltransferase), or a Rho-glucosylating toxin (*C. difficile* Toxin A and Toxin B).

According to yet another aspect of the invention, methods of identifying an agent that modulates polypeptide O-glycosylation are provided. The methods include (a) contacting a glucosyltransferase enzyme, a sugar donor, and a candidate modulating compound with a molecule that includes a detectably labeled polypeptide having: (i) a glycosylation site and (ii) a specific protease cleavage site positioned in the polypeptide such that the rate of specific protease cleavage of the polypeptide glycosylated at the glycosylation site is different than the rate of specific protease cleavage of the polypeptide not glycosylated at the glycosylation site, wherein the detectable label is positioned in the polypeptide such that a change in the detectable label identifies cleavage of the polypeptide by the specific protease at the specific protease cleavage site; (b) adding to the contacted polypeptide the specific protease; (c) monitoring specific protease cleavage of the polypeptide; and (d) comparing the specific protease cleavage of the polypeptide to a control specific protease cleavage, wherein a difference in the control specific protease cleavage compared to the cleavage of the polypeptide contacted with the candidate modulating compound identifies the candidate modulating compound as modulating O-glycosylation of the polypeptide. In certain embodiments the O-glycosylation site comprises a serine or threonine amino acid residue. In some embodiments the glucosyltransferase enzyme is O-GlcNAc transferase; an N-acetylgalactosaminyltransferase; UDP-D-xylose proteoglycan core protein β D-xylosyltransferase, UDP GalNAc:polypeptide N-acetylgalactosaminyltransferase, ppGalNAcTs, GDP-fucose protein O-fucosyltransferase 1 (POFUT1), UDP-glucose:protein glucosyltransferase (glycogen initiator synthase or EGF-glucosyltransferase), or a Rho-glucosylating toxin (*C. difficile* Toxin A and Toxin B). In some embodiments, the sugar donors is UDP-GlcNAc, UDP-GalNAc, UDP-Gal, UDP-Glc, UDP-GlcA (UDP-glucuronic acid), GDP-fucose, CMP-sialic acid, or UDP-xylose. In some embodiments the sugar donor is a UDP-sugar. In certain embodiments the control level of cleavage is the level of specific protease cleavage of a essentially equivalent polypeptide of (a) contacted with glucosyltranferase enzyme, the sugar donor, and the specific protease; but not contacted with the candidate modulating agent. In some embodiments monitoring cleavage comprises monitoring the rate of cleavage. In some embodiments the specific protease cleavage of the polypeptide contacted with the candidate modulating agent is increased compared to the control cleavage identifying the candidate modulating agent as an inhibitor of the O-glycosylation of the O-glycosylation site.

According to another aspect of the invention, kits for identifying an agent that modulates O-glycosylation are provided. The kits include a package housing a first container containing a polypeptide substrate of any forgoing aspects of the invention, and instructions for using the polypeptide to identify modulators of O-glycosylation. In certain embodiments, the kit also includes a second container containing the specific protease that cleaves at the specific protease site of the polypeptide. In some embodiments, the polypeptide comprises the amino acid sequence set forth as one of SEQ ID NOs:1-6, 25, or 26.

According to yet another aspect of the invention, compositions that include an isolated compound of the compounds set forth as compounds 1-28 or a derivative, analog, or variant of one of compounds 1-28 and a pharmaceutically acceptable carrier are provided. The invention also provides compositions that include other isolated compounds that are disclosed herein and act as inhibitors of O-linked glycosylation. In some embodiments, an inhibitor compound of the invention may be provided in a composition that also includes a pharmaceutically acceptable carrier.

According to another aspect of the invention, methods for treating an O-glycosylation-associated disease or condition in a subject are provided. The methods include administering to a subject in need of such treatment an effective amount of an O-glycosylation inhibiting compound to treat the O-glycosylation-associated disease or condition, wherein the O-glycosylation-inhibiting compound is any one of compounds 1-28 or an analog, derivative, or variant of any one of compounds 1-28 that inhibits O-glycosylation activity. In some embodiments, the subject is human. In certain embodiments, the O-glycosylation-inhibiting compound is linked to a targeting molecule. In some embodiments, the O-glycosylation-inhibiting compound is administered prophylactically to a subject at risk of having an O-glycosylation-associated disease or disorder. In some embodiments, the O-glycosylation-inhibiting compound is administered in combination with an additional drug for treating an O-glycosylation-associated disease or disorder. In some embodiments, the O-glycosylation-associated disease or disorder is Alzheimer's disease; cancer; diabetes mellitus, insulin resistance, a complication of diabetes, tumorigenesis, metastasis, bacterial infection and associated complications such as sepsis. In certain embodiments, the complication of diabetes is microvascular damage, insulin resistance, vascular damage, nephropathy, skin ulcers, circulatory damage, diabetic nephropathy, diabetic retinopathy, macro-vascular disease, micro-vascular disease, or diabetic neuropathy. The invention also provides methods of treating an O-glycosylation-associated disease or condition that includes administration of one or more compounds disclosed herein that act as inhibitors of O-linked glycosylation.

According to another aspect of the invention, kits for treating a subject in accordance with any embodiments of the forgoing aspect of the invention are provided. The kits include (a) a package housing a first container containing at least one dose of an O-glycosylation-inhibiting compound, and (b) instructions for using the O-glycosylation-inhibiting compound in the treatment of an O-glycosylation-associated disease or disorder. In some embodiments, the O-glycosylation-inhibiting compound is one of the compounds set forth as compounds 1-28 or an analog, derivative, or variant of one of the compounds set forth as compounds 1-28 that inhibits O-glycosylation activity. In some embodiments, the O-glycosylation-inhibiting compound is linked to a targeting molecule. In certain embodiments, the O-glycosylation-inhibiting compound is administered prophylactically to a subject at risk of having an O-glycosylation-associated disease or disorder. In some embodiments, the O-glycosylation-inhibiting compound is administered in combination with an additional drug for treating an O-glycosylation-associated disease or disorder. In some embodiments, the O-glycosylation-associated disease or disorder is Alzheimer's disease; cancer; diabetes mellitus, insulin resistance, a complication of diabetes, tumorigenesis, metastasis, bacterial infection and associated complications such as sepsis. In certain embodiments, the complication of diabetes is microvascular damage, insulin resistance, vascular damage, nephropathy, skin ulcers, circulatory damage, diabetic nephropathy, diabetic retinopathy, macro-vascular disease, micro-vascular disease, or diabetic neuropathy.

According to yet another aspect of the invention, methods for inhibiting O-glycosylation activity in a cell or tissue are provided. The methods include contacting the cell or tissue with an effective amount of an O-glycosylation-inhibiting compound to inhibit O-glycosylation activity in the cell, or tissue. In some embodiments, the O-glycosylation-inhibiting compound is one of the compounds set forth as compounds 1-28 or an analog, derivative, or variant of one of the compounds set forth as compounds 1-28 that inhibits O-glycosylation activity. In some embodiments, the O-glycosylation-inhibiting compound is linked to a targeting molecule.

According to yet another aspect of the invention, methods of detecting de-glycosylation of a polypeptide are provided. The methods include (a) contacting a glycosidase enzyme with a molecule that includes a detectably labeled polypeptide substrate having: (i) a glycosylated O-glycosylation site and (ii) a specific protease cleavage site positioned in the polypeptide such that the rate of cleavage of the polypeptide by the specific protease at the specific protease cleavage site is different when the polypeptide is O-glycosylated at the glycosylation site than when the polypeptide is not O-glycosylated at the glycosylation site, wherein the detectable label is positioned in the polypeptide such that a change in the detectable label identifies cleavage of the polypeptide by the specific protease; (b) adding to the contacted polypeptide the specific protease that cleaves at the specific protease cleavage site of the polypeptide; and (c) monitoring the cleavage of the polypeptide, wherein the rate of cleavage is characteristic of the level of de-glycosylation of the glycosylation site. In certain embodiments, the O-glycosylation site includes a serine or threonine amino acid residue. In some embodiments, monitoring cleavage comprises monitoring cleavage rate. In some embodiments, the glycosidase enzyme is N-acetyl β-glucosaminidase.

According to another aspect of the invention, methods for identifying an agent that modulates polypeptide de-glycosylation are provided. The methods include (a) contacting a glycosidase enzyme and a candidate modulating compound with a molecule that includes a detectably labeled polypeptide substrate having: (i) an O-glycosylated glycosylation site and (ii) a specific protease cleavage site positioned in the polypeptide such that the rate of specific protease cleavage of the polypeptide glycosylated at the glycosylation site is different than the rate of specific protease cleavage of the polypeptide not glycosylated at the glycosylation site, wherein the detectable label is positioned in the polypeptide such that a change in the detectable label identifies cleavage of the polypeptide by the specific protease at the specific protease cleavage site; (b) adding to the contacted polypeptide the specific protease; (c) monitoring specific protease cleavage of the polypeptide; and (d) comparing the specific protease cleavage of the polypeptide to a control specific protease cleavage, wherein a difference in the control specific protease cleavage compared to the cleavage of the polypeptide contacted with the candidate modulating compound identifies the candidate modulating compound as modulating de-glycosylation of the polypeptide. In some embodiments, the O-glycosylation site comprises a serine or threonine amino acid residue. In certain embodiments, the glycosidase enzyme is N-acetyl β-glucosaminidase. In some embodiments, the control level of cleavage is the level of specific protease cleavage of a essentially equivalent polypeptide of (a) contacted with the glycosidase enzyme and the specific protease; but not contacted with the candidate modulating agent. In some embodiments, monitoring cleavage comprises monitoring the rate of cleavage. In certain embodiments, the specific protease cleavage of the polypeptide contacted with the candidate modulating agent is decreased compared to the control cleavage identifying the candidate modulating agent as an inhibitor of the de-glycosylation of the O-glycosylation site.

According to yet another aspect of the invention, kits identifying an agent that modulates de-glycosylation are provided. The kits include a package housing a first container containing a polypeptide substrate of any embodiment of a foregoing aspect of the invention, and instructions for using the polypeptide to identify modulators of de-glycosylation. In some embodiments, additionally including a second container containing the specific protease that cleaves at the specific protease site of the polypeptide. In some embodiments, the polypeptide comprises the amino acid sequence set forth as one of SEQ ID NOs:1-6, 25, or 26.

These and other objects of the invention will be described in further detail in connection with the detailed description of the invention.

BRIEF DESCRIPTION OF THE DRAWINGS

FIG. 17 shows the results for the protease protection assay for ppGalNacT1.

DETAILED DESCRIPTION OF THE INVENTION

Figure 1:
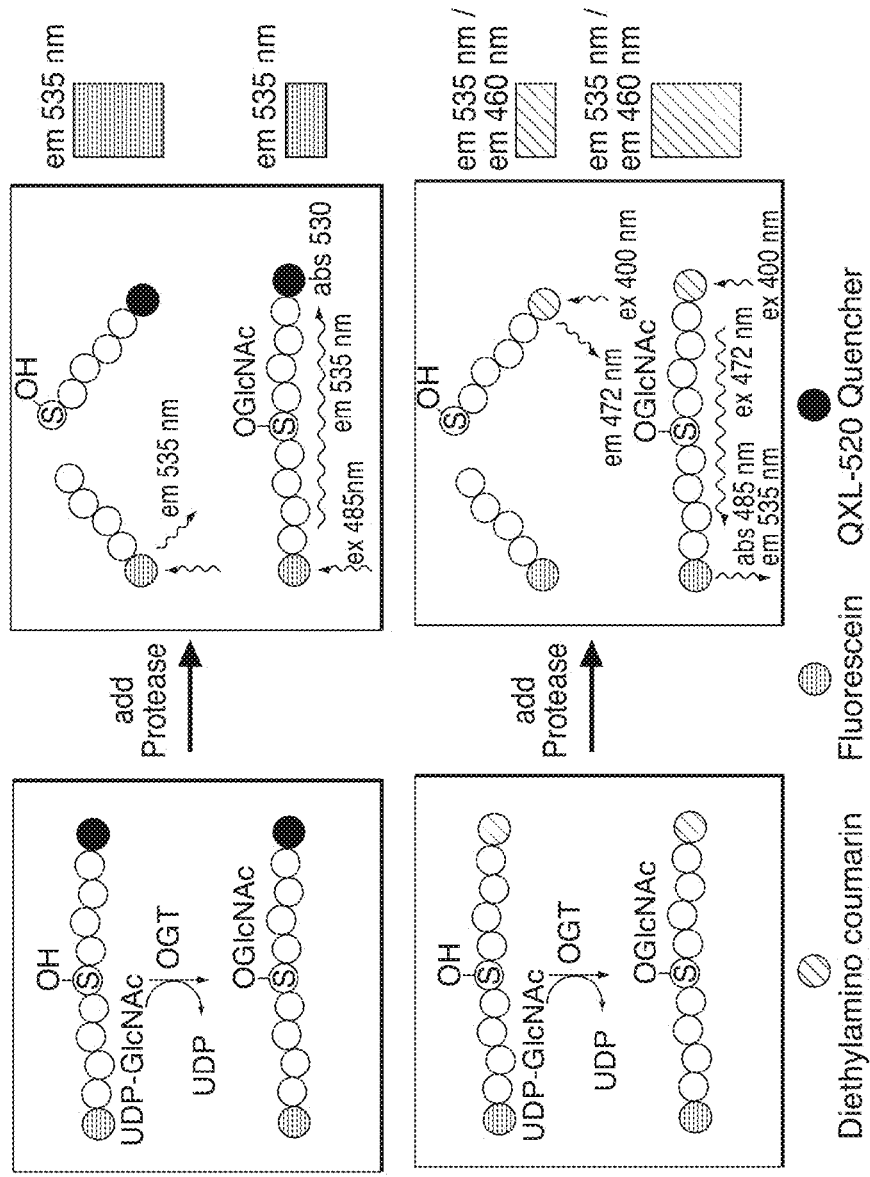
FIG. 1 shows a schematic diagram of a FRET and a quencher/fluorescence pair detectable labels.

Methods and products of the invention, in part, involve assays to determine O-glycosylation of polypeptides and to identify compounds that modulate activity of enzymes that O-glycosylate polypeptides. The invention also includes compounds, and compositions that contain compounds that modulate O-glycosylation of polypeptides. In some embodiments, the modulation is inhibition and the compounds may reduce O-glycosylation of polypeptides by an O-glycosylating enzyme. In certain embodiments, the inhibition may be enhancement of O-glycosylation and the compound may increase the O-glycosylation of polypeptides by an O-glycosylating enzyme. Methods of the invention may include administration of one or more compounds that modulate O-glycosylation of an O-glycosylation site in a polypeptide. For example, a compounds of the invention include compounds that modulate O-glycosylation of serine and/or threonine in a polypeptide.

O-glycosylating enzymes catalyze the transfer of the N-acetylglucosamine from an activated sugar donor to a serine or threonine residue in a polypeptide, e.g. to a protein or polypeptide substrate. Examples of O-glycosylating enzymes whose activity may be monitored using assays of the invention, and whose activity may be modulated by compounds of the invention, include, but are not limited to, the enzymes O-Glc-NAc transferase (OGT), N-acetylgalactosaminyltransferase UDP-D-xylose:proteoglycan core protein beta-D-xylosyltransferase; UDP GalNAc:polypeptide N-acetylgalactosaminyltransferases: ppGalNAcTs, GDP-fucose protein O-fucosyltransferase 1 (POFUT1), UDP-glucose:protein glucosyltransferase (glycogen initiator synthase OR EGF-glucosyltransferase); and Rho-glucosylating toxins such as C. difficile Toxin A and Toxin B, etc. The invention, in some aspects, also includes the use of O-glycosylation enzyme splice variants. Non-limiting examples of sugar donors useful in methods of the invention include: UDP-GlcNAc, UDP-GalNAc, UDP-Gal, UDP-Glc, UDP-GlcA (UDP-glucuronic acid), GDP-fucose, CMP-sialic acid, and UDP-xylose.

Compositions of the invention include compounds that modulate O-glycosylation activity in cells, tissues, and subjects. As used herein, the term "O-glycosylation-inhibiting compound" means a compound that reduces O-glycosylation of serine and/or threonine residues in a polypeptide. Methods of the invention, in some aspects, involve the administration of one or more O-glycosylation-inhibiting compounds to a cell, tissue, or subject and are useful to reduce or prevent cell death and/or damage or disease associated with hyper O-glycosylation of polypeptides such as that resulting in an O-glycosylation-associated disease or disorder. In some embodiments, methods of the invention include administration of one or more de-glycosylation inhibiting compounds to a cell, tissue, or subject and are useful to reduce damage or disease that is associated with hypo O-glycosylation of polypeptides such as that resulting from an de-glycosylation-associated disease or disorder. The terms "O-glycosylation" and "glycosylation" are used interchangeably herein and the terms "protein," "polypeptide," and "peptide" are used interchangeably.

Diseases and Disorders

As used herein, the term "O-glycosylation-associated disease or disorder" includes, but is not limited to diseases and disorders in which there is abnormal O-glycosylation enzyme activity and/or abnormal levels of O-glycosylation. As used herein, the term "O-glycosylation enzyme activity" means O-glycosylation enzyme-mediated O-glycosylation. In some disease and conditions an abnormal level of O-glycosylation enzyme activity and/or O-glycosylation of a polypeptide may be a level that is higher than a normal level (hyper-O-glycosylation). In certain diseases or conditions an abnormal level of O-glycosylation may be a level that is lower than a normal level (hypo-O-glycosylation). As used herein, a "normal" level of O-glycosylation is the level of O-glycosylation in a cell, tissue, or subject that does not have a disease or disorder associated with O-glycosylation enzyme activity, glycosylase enzyme activity, and/or with the O-glycosylation state of polypeptides.

Examples of diseases and disorders associated with O-glycosylation enzyme activity and/or O-glycosylation of polypeptides include, but are not limited to neurodegenerative disorders such as Alzheimer's disease; cancer; diabetes mellitus, insulin resistance, and complications of diabetes, tumorigenesis, metastasis, bacterial infection and associated complications such as sepsis, and complications of other O-glycosylation-associated diseases. As used herein, the term "complication of diabetes" is used to mean a disorder that is associated with diabetes. Non-limiting examples of complications of diabetes include microvascular damage, insulin resistance, vascular damage, nephropathy, skin ulcers, circulatory damage, diabetic nephropathy, diabetic retinopathy, macro-vascular disease, micro-vascular disease, and diabetic neuropathy. In some aspects of the invention, an O-glycosylation-inhibiting compound may be used to treat a subject with diabetes.

The term "diabetic" as used herein, means a subject who, at the time the sample is taken, has a primary deficiency of insulin. The term diabetic includes, but is not limited to, individuals with juvenile diabetes (Type 1 diabetes), adult-onset diabetes (Type 2 diabetes), gestational diabetes, and any other conditions of insulin deficiency and/or abnormally high levels of β-glycosylating enzyme activity and/or abnormally high levels of O-glycosylation of polypeptides. The terms "diabetic" and "diabetes" are terms of art, known and understood by those practicing in the medical profession, a formal definition of which can be found in Harrison's Principles of Medicine (Harrisons, Vol 14, Principles of Internal Medicine, Eds. Fauci, A. S., E. Braunwald, K. J. Isselbacher, J. D. Wilson, J. B. Martin, D. L. Kasper, S. L. Hauser, D. L. Longo, McGraw-Hill, New York, 1999).

Subjects with blood glucose levels that are higher than normal but not yet in the range associated with a diagnosis of diabetes may be considered to have "pre-diabetes." Pre-diabetes is also known in the art as "impaired fasting glucose" (IFG) or "impaired glucose tolerance" (IGT). Subjects with pre-diabetes have a higher risk of developing type 2 diabetes, which is also known as adult-onset diabetes or noninsulin-dependent diabetes. Subjects with pre-diabetes frequently go on to develop type 2 diabetes within 10 years, without intervention—such as diet change and/or activity changes. Health effects associated with diabetes may include heart attack, stroke, blindness, deafness, amputations, kidney failure, burning foot syndrome, venous insufficiency with ulceration and stasis dermatitis. Subjects with pre-diabetes also have a higher risk of heart disease. Insulin resistance can also occur in people who have type 1 diabetes, especially if they are overweight.

Assays

In some aspects the invention includes assays to assess activity of glycosidase enzymes and assays to identify compounds that modulate the deglycosylation of polypeptides. De-glycosylation is the removal of sugars from proteins. An example of a glycosidase enzyme, though not intended to be limiting is: N-acetyl β-glucosaminidase (EC 3.2.1.52). Assays of the invention may be used to identify compounds that modulate de-glycosylation of polypeptides. Compounds that modulate de-glycosylation of polypeptides are referred to herein as de-glycosylation modulating compounds. Deglycosylation modulating compounds of the invention may be de-glycosylation inhibitors (e.g., glycosidase inhibitors) or de-glycosylation enhancers (e.g., glycosidase enhancers). Such compounds may be administered to a cell, tissue, or subject to prevent or treat de-glycosylation-associated diseases or disorders. Diseases and disorders associated with de-glycosylation are referred to herein as de-glycosylation-associated diseases and disorders and include, but are not limited to, ischemia and traumatic injury and complications thereof. De-glycosylation modulating compounds of the invention may be used to treat or prevent ischemic and/or traumatic injury. A de-glycosylation inhibitor may inhibit activity of a glycosylase enzyme.

Methods of the invention may include assays for determining activity of O-glycosylating enzymes in the O-glycosylation of polypeptides. Assays of the invention may also be used to assess whether or not a candidate compound modulates O-glycosylation of polypeptides, e.g., whether it modulates O-glycosylating enzyme activity.

Assays of the invention may include a molecule that comprises a detectably labeled polypeptide. The molecule may be a polypeptide or any other type of molecule and includes a detectably labeled polypeptide substrate sequence. In some embodiments, the molecule consists only of a detectably labeled polypeptide substrate sequence. In other embodiments of the invention the detectably labeled polypeptide may be part of a larger molecule that may have any structure or composition, as long as the molecule can function and can be used in an assay of the invention. For example, a molecule used in an assay of the invention may be a polypeptide, the sequence of which includes but is longer than the detectably labeled polypeptide substrate. Such a molecule may be used in methods and assays of the invention as long as the molecule's structure permits detection of O-glycosylation or de-glycosylation of the peptide substrate portion of the molecule in an assay of the invention.

Assays of the invention may include contacting a glycosylating enzyme and a sugar donor with a molecule comprising a polypeptide substrate of the invention under conditions that permit glycosylation of the glycosylation site in the polypeptide substrate. The polypeptide substrate is then contacted with a specific protease that recognizes the cleavage site for the specific protease that is included in the polypeptide substrate. Because the rate of cleavage by the protease will differ depending on whether or not the polypeptide substrate is glycosylated at the glycosylation site, a determination can be made based on the cleavage (e.g. rate of cleavage) whether the polypeptide substrate is or is not glycosylated. The rate of cleavage therefore is an indicator of glycosylation of the polypeptide substrate. This permits the assay to be used to determine whether a polypeptide substrate is glycosylated (e.g., whether a glycosylating enzyme has activity). Also, assays of the invention may be used to assess candidate compounds that can be included in the assay to see whether they modulate glycosylating activity and glycosylation. In some embodiments, an increase in cleavage by the protease in the presence of the candidate modulating compound indicates that glycosylation is inhibited by the candidate modulating compound.

In some embodiments, assays of the invention may include contacting a glycosidase with a molecule that includes a polypeptide substrate of the invention that is O-glycosylated at an O-glycosylation site in the polypeptide substrate. The polypeptide substrate is then contacted with a specific protease that recognizes the cleavage site for the specific protease that is included in the polypeptide substrate. Because the rate of cleavage by the protease will differ depending on whether or not the polypeptide substrate is glycosylated at the glycosylation site, a determination can be made based on the cleavage (e.g. rate of cleavage) whether the polypeptide substrate is or is not glycosylated. The rate of cleavage therefore is an indicator of glycosylation of the polypeptide substrate. This permits the assay to be used to determine whether a polypeptide substrate contacted with a glycosidase has been de-glycosylated (e.g., whether the glycosidase was effective). Also, assays of the invention may be used to assess candidate compounds that can be included in the assay to see whether they modulate the de-glycosylating activity and de-glycosylation (e.g. whether they modulate a glycosidase).

Polypeptide Substrates

A polypeptide substrate of the invention useful in methods and assays of the invention can be any suitable length for use in an assay, and includes, at least, a) an O-glycosylation site and b) a specific protease cleavage site. The O-glycosylation site consists of an amino acid that can accept a sugar transferred by an O-glycosylating enzyme. Examples of O-glycosylation sites that may be included in a polypeptide substrate of the invention are the amino acids serine or threonine. In some embodiments the polypeptide substrate is detectably labeled.

Methods and assays of the invention may be performed under conditions that permit glycosylation of the polypeptide substrate. For example, when an assay of the invention includes contacting a glucosyltransferase enzyme and a sugar donor with a molecule that includes a detectably labeled polypeptide substrate, the contact is carried out under suitable conditions for glycosylation of the polypeptide. Conditions, (e.g., temperature, length of incubation, buffer constituents, pH, etc.) under which the contact is carried out are conditions under which the glucosylatranferase enzyme is able to utilize the sugar donor (e.g., UDP-sugar or other suitable sugar donor) and glycosylate the polypeptide substrate at the O-glycosylation site. Such conditions are known in the art and may be optimized for a given glycosylating enzyme and sugar using routine methods. Examples, though not intended to be limiting, of conditions for glycosylating polypeptide substrates of the invention are provided the Examples section herein. Alternative conditions that may be used with methods and compounds of the invention are known and may be selected by those of ordinary skill in the art. Methods and assays of the invention may also include the use of assays of the invention to assess the ability of candidate agents to modulate glycosylation of a polypeptide substrate of the invention. In such embodiments, an assay may include conditions that are conducive to allowing glycosylation but may also include a candidate compound to be tested for its ability to modulate (inhibit or enhance) O-glycosylation.

Polypeptide substrates of the invention also include a specific protease cleavage site that is positioned in the polypeptide substrate such that the rate of cleavage by the specific protease at the specific protease cleavage site is different when the polypeptide is glycosylated at the O-glycosylation site than the rate of cleavage when the polypeptide is not glycosylated at the O-glycosylation site. As used herein, the term "positioned" means placed in the amino acid sequence of the polypeptide substrate. In some embodiments, a specific protease cleavage site may be located adjacent to the O-glycosylation site (e.g. directly next to the serine or threonine). In some embodiments, the specific protease cleavage site may be located within 1, 2, 3, 4, or 5 amino acids of the O-glycosylation site. The specific protease cleavage site may be located on either the N-terminal side of the O-glycosylation site or on the C-terminal side of the O-glycosylation site. The protease cleavage site may be on the N-terminal side of the O-glycosylation site, which means the protease cleavage site is closer to the N terminus of the polypeptide substrate than is the O-glycosylation site. Similarly, in some embodiments the protease cleavage site may be on the C-terminal side of the O-glycosylation site, which means the protease cleavage site is closer to the C terminus of the polypeptide substrate than is the O-glycosylation site. Thus, in some embodiments of the invention the position of the specific protease cleavage site may be exemplified as follows:

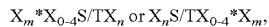

$$X_m*X_{0-4}S/TX_n \text{ or } X_nS/TX_{0-4}*X_m,$$

where m and n are independently any number of amino acids 1 or higher, X can be any amino acid, with the number of amino acids determined by the subscript, * is the specific protease cleavage site, and S/T is either serine or threonine. In some embodiments of the invention there is only a single specific cleavage site in the polypeptide substrate. There may be other of the specific cleavage sites outside of the polypeptide substrate as long as cleavage at the additional sites does not interfere with detection of cleavage of the polypeptide substrate. In certain embodiments, there is only one of the specific protease cleavage sites in the polypeptide substrate. In some embodiments of the invention, there is only one of the specific protease cleavage sites between two detectable labels or between a detectable label and its quenching partner in the polypeptide substrate.

As used herein the term "specific protease cleavage site" means the specific location that the protease cleaves the polypeptide. Thus, the specific protease cleavage site is located between two adjacent amino acids. It will be understood by those of ordinary skill in the art that the recognition site for a specific protease may include one, two, three, four, or more amino acids depending on the specific recognition requirements of the protease for the polypeptide. Those of ordinary skill in the art will readily be able to identify cleavage sites and recognition sites for specific proteases. Details of specific protease cleavage sites and protease recognition sites are well known in the art, including for example, at the PeptideCutter pages of ExPASY. (www.expasy.ch/tools/peptidecutter/) and Keil, B. Specificity of proteolysis. Springer-Verlag Berlin-Heidelberg-NewYork, pp. 335. (1992). Those of ordinary skill in the art can use available tools and published information to identify a specific protease site for inclusion in a polypeptide substrate for use in methods and compositions of the invention. Examples of proteases that may be used in methods of the invention, include, but are not limited to: proteinase K, trypsin, chymotrypsin, thermolysin, Staphylococcal peptidase I, Proline-endopeptidase, Pepsin, Glutamyl endopeptidase, Factor Xa, Granzyme B Lysyl endopeptidase, Asp-N Endopeptidase, and enterokinase, etc. Those of skill in the art will be able to utilize additional proteases cleavage sites in polypeptide substrates of the invention and will be able to determine glycosylation and de-glycosylation status of polypeptides based on cleavage by specific proteases in methods of the invention without undue experimentation.

Methods and assays of the invention may be performed under standard conditions that permit cleavage of the specific protease cleavage site by the specific protease. For example, when an assay of the invention includes contacting a polypeptide substrate with a protease, the contact is carried out under suitable standard conditions that permit the specific protease to function. Conditions, (e.g., temperature, length of incubation, buffer constituents, pH, etc.) under which the contact is carried out are conditions under which the protease is able to cleave a polypeptide substrate at the specific protease cleavage site. Such standard conditions are known in the art and may be optimized for the specific protease using routine methods. Examples, though not intended to be limiting, of conditions for protease cleavage are provided the Examples section herein. Alternative conditions that may be used with methods and compounds of the invention are known and may be selected by those of ordinary skill in the art without undue experimentation. In some embodiments, glycosylation of a polypeptide substrate may reduce or eliminate cleavage by a specific protease under standard conditions that permit normal cleavage of the polypeptide substrate by the specific protease.

In methods and molecules of the invention, the positioning of the O-glycosylation site in relation to the specific protease cleavage site in the polypeptide substrate is such that the rate of cleavage of the polypeptide substrate by the specific protease is different with the polypeptide is glycosylated at the O-glycosylation site than the rate of cleavage is with the O-glycosylation site is not glycosylated. Thus, the presence of the O-glycosylated serine or threonine alters the rate of cleavage of the polypeptide substrate by the specific protease. In some embodiments of the invention, the rate of cleavage of the polypeptide substrate is higher when the polypeptide is not glycosylated at the O-glycosylation site than when the polypeptide substrate is glycosylated at the O-glycosylation site. Thus, in some embodiments, the difference in rate of cleavage indicates whether a polypeptide substrate (or a plurality of the polypeptide substrate) is glycosylated or is not glycosylated at the O-glycosylation site. For example, the rate of cleavage by a specific protease at the specific protease cleavage site may be 2, 5, 10, 20, 30, 40, 50, 60, 70, 80, 90, 100, 200, 300, 400, 500, 600, or more times faster (including all times numbers in between the listed numbers) in unglycosylated versus glycosylated polypeptide substrates of the invention.

Detection

Detection of cleavage and cleavage rate of a polypeptide substrate of the invention can be performed using numerous methods. Polypeptide length and the presence of fragments may be assessed as an indication of cleavage. Such assessment may be done using polypeptide substrates that are detectably labeled but methods of the invention may also be used with polypeptide substrates that are not detectably labeled, for example assessment of cleavage may be performed using assay methods such as gel electrophoresis, centrifugation separation, etc. Those of ordinary skill in the art will recognize numerous methods available that can be used to determine substrate length or the presence and/or identify of cleavage fragments.

In some embodiments of the invention, polypeptide substrates are detectably labeled and detection of the detectable labels is used to determine cleavage and/or rate of cleavage of a polypeptide substrate. A detectable label on a polypeptide substrate may be positioned in the polypeptide such that a change in the detectable label identifies cleavage of the polypeptide by the specific protease at the specific protease cleavage site, and as indicated elsewhere herein, cleavage of the polypeptide substrate (e.g. rate of cleavage) indicates whether the polypeptide substrate is glycosylated or not glycosylated at the O-glycosylation site.

The use of detectable labels for determining cleavage is well known by those of ordinary skill in the art. A detectable moiety may be positioned at one location on a polypeptide substrate such that removal of the label from the remainder of the substrate by cleavage of the substrate indicates cleavage of the substrate. A variety of methods may be used to detect the label, depending on the nature of the label and other assay components. A detectable moiety may be directly detected through optical or electron density, radioactive emissions, nonradiative energy transfers, etc. or indirectly detected with antibody conjugates, strepavidin-biotin conjugates, etc. Methods for detecting the labels are well known in the art. In some embodiments, a detectable moiety may be biotin, a fluorophore, chromophore, enzymatic, or a radioactive moiety.

In assays and methods of the invention, following a glycosylation step and incubation with the protease specific for the protease site in the polypeptide substrate, the rate of protease cleavage of the polypeptide may be detected by any convenient method available to the user. Detection may be effected in any convenient way for the assay, for example for a high-throughput assay detection may be most convenient using a detectable label that is a fluorescent or luminescent moiety that allows for high sensitivity and rapid detection. In other embodiments and assays, other types of detectable labels and detection methods may be used. A wide variety of detectable labels can be used, such as those that provide direct detection (e.g., radioactivity, luminescence, optical or electron density, etc.) or indirect detection (e.g., epitope tag such as the FLAG epitope, enzyme tag such as horseradish peroxidase, etc.).

As used herein the term detectable label, includes, but is not limited to a fluorescent or bioluminescent detectable moiety. Detection of a fluorescent or bioluminescent detectable label of the invention may be performed using any suitable imaging method, including, but not limited to video microscopy, real-time imaging, or other means that permit imaging of detectable labels of the invention.

In some aspects of the invention, a detectable moiety is attached to a polypeptide substrate in a form that is not detectable, (e.g., is quenched or not fluorescent or luminescent at an appropriate detection wavelength) until cleavage of the polypeptide substrate. For example, a fluorescent moiety may be conjugated to one end of the polypeptide substrate and a light-quenching moiety such as BHQ3 or Iowa black may be conjugated on to another position of the polypeptide substrate, for example with the protease cleavage site between the fluorescent and light-quenching moieties. Thus, when the polypeptide substrate is intact, the fluorescence emitted from the fluorescent moiety is quenched and when the polypeptide substrate is cleaved by the specific protease at the specific protease cleavage site, the fluorescence is unquenched and may be detected. Similarly, FRET methods and molecules may be used in methods and on polypeptide substrates of the invention such that a detectable shift in fluorescence occurs when the polypeptide substrate is cleaved at the specific protease cleavage site, thus separating the donor and acceptor FRET molecules. The detectable label will be detectable when the polypeptide substrate has been cleaved thus indicating cleavage at the protease cleavage site. FIG. 1 illustrates examples of assays utilizing FRET moieties and quenching/fluorescent moieties.

In some embodiments, a fluorescent or luminescent molecule is attached to a polypeptide substrate (using standard methods) in conjunction with another fluorescent molecule such that FRET and/or BRET methods result in a wavelength of light emission that shifts when there is cleavage of the polypeptide substrate and the first fluorescent molecule is no longer in close enough proximity to the second fluorescent molecule. In each case, a change in the level or wavelength of detectable light emitted from the detectably labeled polypeptide substrate of the invention upon cleavage by the specific substrate can be used to detect the cleavage of the polypeptide substrate. As indicated above herein, the rate at which cleavage of a polypeptide substrate occurs indicates the glycosylation state of the O-glycosylation site of the polypeptide substrate. Thus, the rate of cleavage of a polypeptide substrate of the invention indicates whether the O-glycosylation site on the polypeptide substrate is or is not glycosylated.

In some embodiments of the invention, detection of cleavage (and thus detection of glycosylation or lack of glycosylation of a polypeptide substrate) is based on the appearance of a fluorescent or luminescent signal that had originally been quenched, e.g., the unquenching of a quenched signal. As used herein, a quenching moiety is a quenching molecule that is attached to a polypeptide substrate of the invention. In some embodiments of the invention, a quenching moiety is an absorbance moiety that does not fluoresce and is able to quench the fluorescent signal of the fluorescent moiety or detectable label. A dark quencher absorbs the fluorescent energy from the fluorophore, but does not fluoresce itself. Rather, the dark quencher dissipates the absorbed energy, typically as heat. Non-limiting examples of dark or non-fluorescent quenchers are Dabcyl, Black Hole Quenchers, Iowa Black, BH3Q, QSY-7, AbsoluteQuencher, Eclipse non-fluorescent quencher, and metal clusters such as gold nanoparticles. Those of ordinary skill in the art will be able to identify and use additional dark quenchers in the methods of the invention without undue experimentation.

In some embodiments of the invention, detection of a target may be based on a shift in fluorescence frequency of a fluorescent or luminescent moiety of the cleaved polypeptide substrate. Examples of detection methods that utilize such a shift are FRET and BRET methods, both of which are methods routinely used in the art. Thus, in some embodiments, a detectable label is a fluorescence donor or donor fluorophore and the quencher is a fluorescence acceptor or acceptor fluorophore. In some embodiments, the donor and acceptor fluorophores form a FRET (fluorescence resonance energy transfer) pair. If the donor fluorophore is excited, for instance by a laser light, a portion of the energy absorbed by the donor is transferred to acceptor fluorophore if the acceptor fluorophores are spatially close enough to the donor molecules (i.e., the distance between them must approximate or be less than the Forster radius or the energy transfer radius). Once the acceptor fluorophore absorbs the energy, it in turn fluoresces in its characteristic emission wavelength, resulting in a shift in frequency of fluorescence. Non-limiting examples of FRET donors include Alexa 488, Alexa 546, BODIPY 493, Oyster 556, Fluor (FAM), Cy3 and TMR (TAMRA). Examples of FRET acceptors include Cy5, Alexa 594, Alexa 647, Oyster 656, Texas red, tetramethylrhodamine (TMR), AlexaFluor dyes, HiLyte Fluorophores, and [2-(1-sulfonyl-5-naphthyl)-aminoethylamide] EDANS.

FRET generally requires only one excitation source (and thus wavelength) and only one detector. The detector may be set to either the emission spectrum of the donor or acceptor fluorophore. The detector is set to the donor fluorophore emission spectrum if FRET is detected by quenching of donor fluorescence. Alternatively, the detector is set to the acceptor fluorophore emission spectrum if FRET is detected by acceptor fluorophore emission. In some embodiments, FRET emissions of both donor and acceptor fluorophores can be detected. In still other embodiments, the donor is excited with polarized light and polarization of both emission spectra is detected.

In other embodiments, the resonance energy transfer signal is due to luminescence resonance energy transfer (LRET; Mathis, G. Clin. Chem. 41, 1391-1397, 1995) and the donor moiety is a luminescent moiety. In some embodiments the luminescent moiety is a chemiluminescent moiety (CRET; Campbell, A. K., and Patel, A. Biochem. J. 216, 185-194, 1983). In some embodiments the luminescent moiety is bioluminescent moiety (BRET; Xu, Y., Piston D. W., Johnson, Proc. Natl. Acad. Sci., 96, 151-156, 1999).

When the resonance energy signal is due to chemiluminescence, the donor moiety can be a lanthanide like Europium or Terbium. Furthermore, where the resonance energy signal is due to chemiluminescence, the donor moiety can be a lanthanide chelate such as DTPA-cytosine, DTPA-cs124, BCPDA, BHHCT, Isocyanato-EDTA, Quantum Dye, or W1024 and the acceptor moiety can be Cy-3, ROX or Texas Red. In some embodiments, due to the range of effective resonance energy transfer of the lanthanide chelate, multiple acceptor moieties may be employed. The donor moiety can be a lanthanide chelate and the acceptor moiety can be a phycobiliprotein. In certain embodiments, the phycobiliprotein is Red Phycoerythrin (RPE), Blue Phycoerythrin (BPE), or Allophycocyanin (APC).

In BRET, the donor protein is a bio-luminescent protein and the acceptor protein is a fluorescent protein. Donor luminescent protein used in BRET may include, but are not limited to *Renilla* luciferase or firefly luciferase. In some embodiments the fluorescent acceptor protein in BRET is a green, red, cyan or yellow fluorescent protein.

The positioning of the detectable labels on the polypeptide substrate is such that a change in the detection of the detectable label indicates cleavage of the substrate. Examples of effective distances between a quenching moiety and a detectable label (or between two members of a FRET or BRET pair) on a polypeptide substrate of the invention are provided herein in the Examples section and those of ordinary skill in the art will recognize routine methods to determine and to optimize the distance between a detectable label and a quencher (or two fluorescent or luminescent labels) for use in methods and compositions of the invention. The use of quenching and fluorescence pairs is well known in the art and those of ordinary skill in the art will be able to utilize and optimize the use of such pairs in methods of the invention without undue experimentation.

In some embodiments, the signal of a quenched detectable label is quenched by at least 1%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%, including all percentages in between each percentage listed. In some embodiments a FRET partner or fluorescent label is on the N-terminal side of the protease cleavage site in the polypeptide substrate and the other member of the FRET pair or a quenching moiety, respectively is on the C-terminal side of the protease cleavage site. In some embodiments a FRET partner or fluorescent label is on the C-terminal side of the protease cleavage site and the other FRET partner or the quenching moiety, respectively, is on the N-terminal side of the protease cleavage site of the polypeptide substrate.

Assay Controls

The rate of cleavage of a polypeptide substrate of the invention can be compared to a control rate of cleavage as a determination of the glycosylation or de-glycosylation of the polypeptide substrate. For example, when testing a candidate compound for activity as a glycosylation enzyme inhibitor or as a glycosidase inhibitor, a test sample that includes the enzyme or inhibitor can be run in an assay of the invention and the rate of cleavage of the polypeptide substrate can be compared to a control rate of cleavage. A difference can indicate whether or not the candidate compound inhibited the activity of the enzyme.

In methods and assays of the invention that are used to evaluate an effect of a candidate compound on O-glycosylating enzyme activity, the results in a test sample may be compared to the results in a control sample that is essentially identical to the test sample, but lacks the candidate compound. Differences in the levels of glycosylation of a glycosylation site in a test and control sample may be compared as a measure of effect of the candidate compound on the O-glycosylation of the polypeptide. Those of ordinary skill in the art will recognize the manner of using control values and samples in conjunction with assays and methods of the invention.

Similarly, in some embodiments of methods and assays of the invention, a control amount or level of O-glycosylating enzyme activity may be the amount in an control sample that is substantially identical to a test sample, but the control sample lacks one or more constituents that are included in the test sample. For example, a test sample for an assay to determine whether a candidate compound modulates O-glycosylation of a polypeptide, may include: a candidate inhibitor compound and (i) a substrate polypeptide that includes an O-glycosylation site and (ii) a specific protease cleavage site positioned in the polypeptide such that the rate of cleavage by the specific protease at the specific protease cleavage site is different when the polypeptide is glycosylated at the O-glycosylation site than when the polypeptide is not glycosylated at the O-glycosylation site, wherein the detectable is label positioned in the polypeptide such that a change in the detectable label identifies cleavage of the polypeptide by the specific protease at the specific protease cleavage site. A control sample may include (i) a substrate polypeptide that includes an O-glycosylation site and (ii) a specific protease cleavage site positioned in the polypeptide such that the rate of cleavage by the specific protease at the specific protease cleavage site is different when the polypeptide is glycosylated at the O-glycosylation site than when the polypeptide is not glycosylated at the O-glycosylation site, wherein the detectable is label positioned in the polypeptide such that a change in the detectable label identifies cleavage of the polypeptide by the specific protease at the specific protease cleavage site, but may not include the candidate inhibitor compound. The specific protease may be added to both the control and test samples under essentially equivalent conditions that permit cleavage of the unglycosylated polypeptide at the protease cleavage site and the rate of cleavage of the polypeptide in each sample may be determined. The rate of cleavage in the sample and the control can be compared to each other to determine whether the candidate modulating compound altered the level of glycosylation of the polypeptide, thus resulting in a difference in the rate of cleavage between the control and the sample tested.

Screening for Compounds

The invention further provides efficient methods of identifying pharmacological compounds or lead compounds and compounds that inhibit (or enhance) O-glycosylating enzyme activity and/or O-glycosylation of polypeptides. Generally, the screening methods involve assaying for compounds that modulate (enhance or inhibit) the level of O-glycosylating enzyme activity and/or O-glycosylation of polypeptides. As will be understood by those of ordinary skill in the art, the screening methods may measure the level of O-glycosylating enzyme activity directly, (e.g. binding and/or catalytic activity). Examples of screening methods are provided in the Examples section. In addition, screening methods may be utilized that measure a secondary effect of O-glycosylating enzyme activity and/or O-glycosylation of polypeptides, for example, the level of cell damage and/or cell death in a cell or tissue sample or by measuring physiological and/or behavioral characteristics of an O-glycosylation-associated disease.

A wide variety of assays for O-glycosylation-inhibiting compounds can be used in accordance with this aspect of the invention, including, O-glycosylating enzyme activity assays, O-glycosylating enzyme displacement assays, purified enzyme assays, cell-free assays, cell-based assays, cell-viability assays, etc. An example of such an assay that is useful to test candidate O-glycosylation-inhibiting compounds is a purified enzyme assay provided in the Examples section. In assays for O-glycosylating enzyme activity modulating compounds, the assay mixture comprises a candidate compound. Typically, a plurality of assay mixtures is run in parallel with different compound concentrations to obtain a different response to the various concentrations. Typically, one of these concentrations serves as a negative control, i.e., at zero concentration of compound or at a concentration of agent below the limits of assay detection.

It is contemplated that cell based assays can also be performed to assess the ability of compounds of the invention to inhibit O-glycosylation activity. Such cell-based assays can be performed using cell samples and/or cultured cells. Biopsy cells and tissues as well as cell lines grown in culture are useful in the methods of the invention.

Candidate compounds useful in accordance with the invention encompass numerous chemical classes, although typically they are organic compounds. Preferably, the candidate compounds are small organic compounds, i.e., those having a molecular weight of more than 50 yet less than about 2500, preferably less than about 1000 and, more preferably, less than about 500. Candidate compounds comprise functional chemical groups necessary for structural interactions with proteins and/or nucleic acid molecules. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid molecule, the agent typically is a DNA or RNA molecule, although modified nucleic acid molecules are also contemplated.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological compounds may be subjected to directed or random chemical modifications such as acylation, alkylation, esterification, amidification, etc. to produce structural analogs of the compounds. Candidate compounds also include analogs, derivatives, and/or variants of the O-glycosylation-modulating compounds described herein.

A variety of other reagents also can be included in the assay mixture. These include reagents such as salts, buffers, neutral proteins (e.g., albumin), detergents, etc. which may be used to facilitate optimal binding, or to reduce non-specific or background interactions of the reaction components. Other reagents that improve the efficiency of the assay such as protease inhibitors, nuclease inhibitors, antimicrobial agents, and the like may also be used.

An exemplary purified enzyme assay that is a kinetic O-glycosylation-inhibition assay is described in the Examples section herein. An O-glycosylation-inhibition assay may be used to assess O-glycosylation of a polypeptide and to identify candidate compounds that inhibit O-glycosylation of polypeptides and physiological effects thereof.

In general, the mixture of the foregoing assay materials is incubated under conditions whereby, in the presence of the candidate compound, the rate of cleavage of the polypeptide is enhanced or reduced, depending on whether the candidate compound is a inhibitor or enhancing compound. The order of addition of components, incubation temperature, time of incubation, and other parameters of the assay may be readily determined by those of ordinary skill in the art. Such experimentation merely involves optimization of the assay parameters, not the fundamental composition of the assay. Incubation temperatures may vary at different steps of assays of the invention. For example, temperatures for the glycosylation step may differ from temperatures for the protease cleavage step. Typically temperatures are between 4° C. and 40° C. and can be optimized for the specific protease during protease cleavage steps of the assay and can be independently optimized for the other steps of the assay. Incubation times preferably are minimized to facilitate rapid, high throughput screening, and typically are between 0.1 and 10 hours.

Amino Acids and Sequences

The invention also includes in part, amino acid sequences and nucleic acid sequences that encode the amino acid sequences that are useful in the assays of the invention. For example amino acid sequences of polypeptide substrates that are useful in assays of the invention. As used herein the term 'polypeptide substrate" means a polypeptide that has: (a) an O-glycosylation site and (b) a specific protease cleavage site positioned in the polypeptide such that the rate of cleavage by the specific protease at the specific protease cleavage site is different when the polypeptide is glycosylated at the O-glycosylation site than when the polypeptide is not glycosylated at the O-glycosylation site, wherein the detectable is label positioned in the polypeptide such that a change in the detectable label identifies cleavage of the polypeptide by the specific protease at the specific protease cleavage site. Exemplary amino acid sequences of polypeptide substrates that are useful in assays, methods, and compositions, of the invention include, but are not limited to STPVSSANMK (SEQ ID NO:1) STPVSFANMK (SEQ ID NO:2); STPVSRANMK (SEQ ID NO:3); EYIPTVFDNK (SEQ IF NO:4); EYRPTVFDNK (SEQ ID NO:5); AND EYIPTVDDNK (SEQ ID NO:6); EPGPTEAPK (SEQ ID NO:25); EDAVTPGPK (SEQ ID NO:26). It will be understood that natural and non-natural amino acids may be used in polypeptide substrate molecules of the invention. In some embodiments of the invention, all amino acids of a polypeptide substrate are naturally occurring amino acids. In some embodiments of the invention, a polypeptide substrate includes at least one natural and at least one non-natural amino acid. In certain embodiments, all amino acids of a polypeptide substrate are non-naturally occurring amino acids.

The invention, in some aspects, includes polypeptide substrates and nucleic acids that encode polypeptide substrates of O-glycosylation and also includes homologs and alleles of the sequences. In general, homologs and alleles typically will share at least 80%, 85%, 90%, 91%, 92%, 93%, 94%, 95%, 96%, 97%, 98%, 99% nucleotide identity and/or at least 95% amino acid identity to the sequences of an encoding nucleic acid and polypeptide substrate, respectively, in some instances will share at least 95% nucleotide identity and/or at least 97% amino acid identity, in other instances will share at least 97% nucleotide identity and/or at least 98% amino acid identity, in other instances will share at least 99% nucleotide identity and/or at least 99% amino acid identity, and in other instances will share at least 99.5% nucleotide identity and/or at least 99.5% amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

The invention also includes degenerate nucleic acids that include alternative codons to those present in the native materials and materials of the invention. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide substrate. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); ARC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides for polypeptide substrates that are modified from those specifically disclosed herein, and the use of such polypeptide substrates. Modified polypeptide substrate sequences may include additions, substitutions, and/or deletions of one or more amino acids. For use in methods and assays of the invention, the modified polypeptides are detectably labeled and retain a glycosylation site and retain a protease specific site (which may differ from one exemplified in a polypeptide substrate disclosed herein), but the remaining amino acids may be modified. The modified polypeptides retain the ability to be glycosylated and to be cleaved by a protease in such a manner that the rate of cleavage of the polypeptide substrate indicates whether the polypeptide substrate is or is not glycosylated. For example, modified polypeptides having single amino acid changes can be prepared. Likewise, modified polypeptides having two amino acid changes can be prepared. Numerous modified polypeptides like these will be readily envisioned by one of skill in the art. Additional polypeptides having additional substitutions (i.e., 3 or more), additions or deletions also can be prepared and are embraced by the invention as readily envisioned by one of ordinary skill in the art. Any of the foregoing polypeptides can be tested by routine experimentation for retention of the ability to be used as a polypeptide substrate in an assay of the invention. As used herein the terms: "deletion", "addition", and "substitution" mean deletion, addition, and substitution changes to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more amino acids of a polypeptide sequence of the invention.

Compounds

Some assays of the invention can be used to monitor glycosylation of polypeptides and can also be used to assess whether or not a candidate agent can modulate activity of an O-glycosylation enzyme and to determine whether an agent modulates O-glycosylation. Thus, assays and methods of the invention may be used to identify compounds that are useful for treating O-glycosylation-associated diseases or disorders. Deleterious effects seen in O-glycosylation-associated diseases and/or disorders that are triggered by abnormal O-glycosylating enzyme activity may be ameliorated by the administration of compounds and/or compositions that modulate O-glycosylating enzyme activity. Compounds of the invention include compounds that modulate O-glycosylation enzyme activity in the O-glycosylation of polypeptides in cells and/or tissues, thereby reducing the cell and tissue damage and clinical manifestations of an O-glycosylation-associated disease or disorder. In some embodiments of the invention, the compounds inhibit activity of an O-glycosylating enzyme and reduce O-glycosylation. Table 1 provides examples of O-glycosylation-inhibiting compounds of the invention.

TABLE 1

O-glycosylation-inhibiting compounds.
Compounds 1-28

TABLE 1-continued
O-glycosylation-inhibiting compounds.
Compounds 1-28
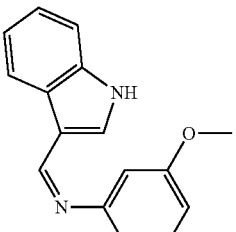
Compound 5
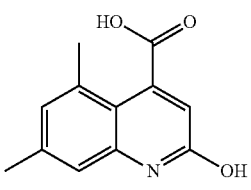 [SMILES: Cc1cc(C)c2c(C(=O)O)cc(O)nc2c1]
Compound 6
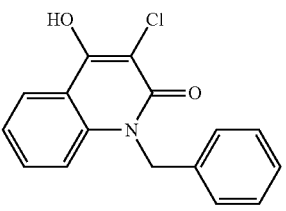 [SMILES: O=c1c(Cl)c(O)c2ccccc2n1Cc1ccccc1]
Compound 7
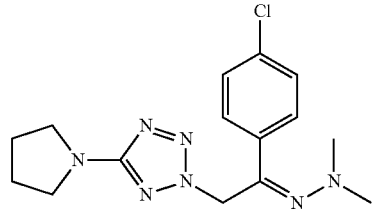 [SMILES: CN(C)/N=C(/Cn1nnc(N2CCCC2)n1)c1ccc(Cl)cc1]
Compound 8
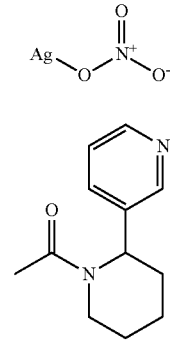
Compound 9
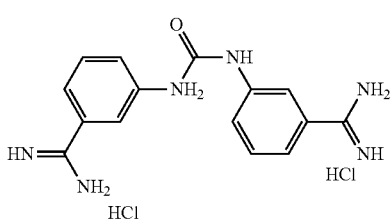 [SMILES: N=C(N)c1cccc(NC(=O)Nc2cccc(C(=N)N)c2)c1 ; Cl ; Cl]
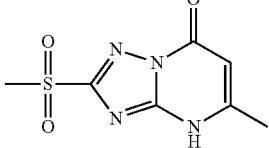
Compound 10
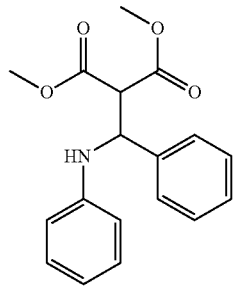 [SMILES: COC(=O)C(C(=O)OC)C(Nc1ccccc1)c1ccccc1]
Compound 11
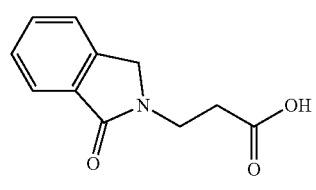 [SMILES: O=C(O)CCN1Cc2ccccc2C1=O]
Compound 12
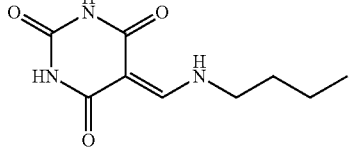
Compound 13
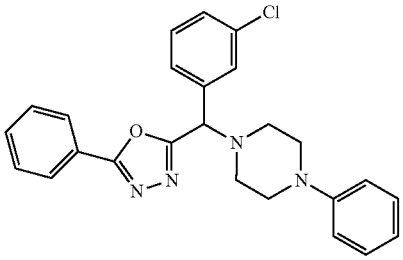 [SMILES: Clc1cccc(C(c2nnc(-c3ccccc3)o2)N2CCN(c3ccccc3)CC2)c1]
Compound 14
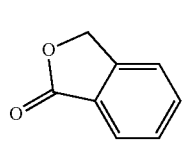
Compound 15
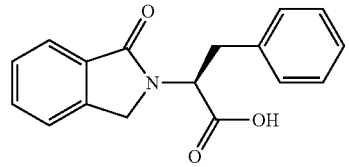 [SMILES: O=C(O)[C@H](Cc1ccccc1)N1Cc2ccccc2C1=O]
Compound 16
Compound 17

TABLE 1-continued

O-glycosylation-inhibiting compounds.
Compounds 1-28

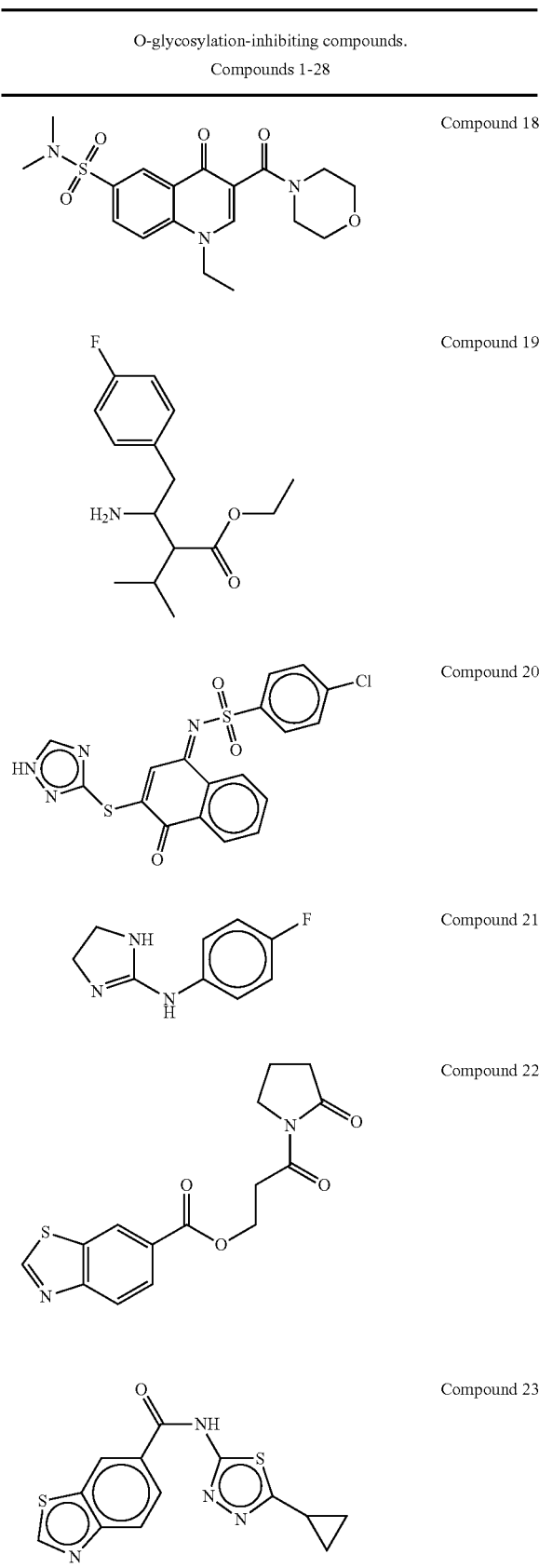

Compound 18

Compound 19

Compound 20

Compound 21

Compound 22

Compound 23

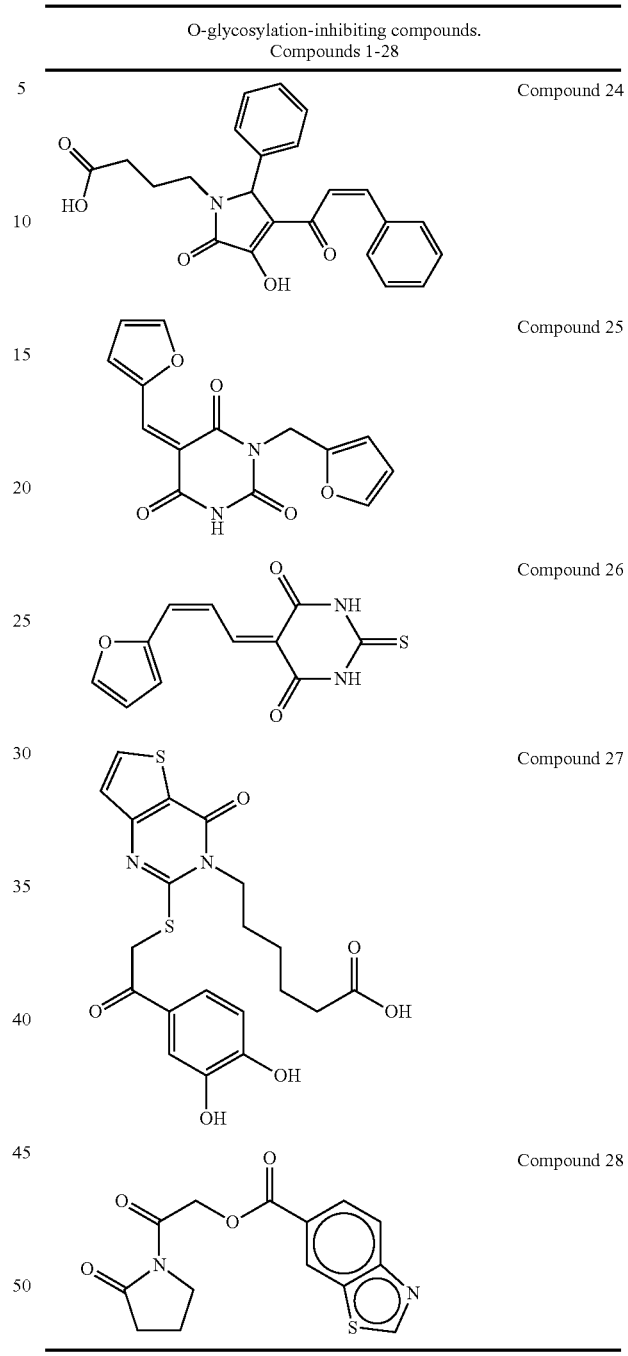

Compound 24

Compound 25

Compound 26

Compound 27

Compound 28

Compounds presented herein as compounds 1-27 may be useful to inhibit O-glycosylation of proteins by O-glycosylating enzymes. Compounds such as those exemplified by compounds 1-27 may be used to treat an O-glycosylation-associated disease or disorder in a subject in need of such treatment. It will be understood by those of ordinary skill in the art that analogs, derivatives, or variants of one or more core compounds or other compounds disclosed herein may be used as inhibitors of O-glycosylation, and in some aspects of the invention, such inhibitors may be used to treat or prevent an O-glycosylation-associated disease or condition, e.g., cancer, diabetes, pre-diabetes, etc.

Some assays of the invention can be used to monitor de-glycosylation of polypeptides and can also be used to assess whether or not a candidate agent can modulate activity of a glycosidase enzyme and to determine whether an agent modulates de-glycosylation. Thus, assays and methods of the invention may be used to identify compounds that are useful for treating de-glycosylation-associated diseases or disorders. Deleterious effects seen in de-glycosylation-associated diseases and/or disorders that are triggered by abnormal de-glycosylating enzyme activity may be ameliorated by the administration of compounds and/or compositions that modulate de-glycosylating enzyme activity. Compounds of the invention include compounds that modulate glycosidase activity in the de-glycosylation of polypeptides in cells and/or tissues, thereby reducing the cell and tissue damage and clinical manifestations of a de-glycosylation-associated disease or disorder. In some embodiments of the invention, the compounds inhibit activity of a glycosidase and reduce de-glycosylation.

A compound of the invention may be an isolated compound. By "isolated", it is meant present in sufficient quantity to permit its identification or use according to the procedures described herein. Because an isolated material may be admixed with a carrier in a preparation or composition, such as, for example, for adding to a sample or for analysis, the isolated material may comprise only a small percentage by weight of the preparation.

In some aspects of the invention, one or more of compounds 1-27 may be administered to a subject that is free of indications for a previously determined use of the compound(s). By "free of indications for a previously determined use", it is meant that the subject does not have symptoms that call for treatment with one or more of the compounds of the invention for a previously determined use of that compound, other than the indication that exists as a result of this invention. As used herein the term "previously determined use" of a compound means the use of the compound that was previously identified. Thus, the previously determined use is not the use of inhibiting O-glycosylation enzyme activity and/or the O-glycosylation of polypeptides.

Methods of the invention may include administration of an O-glycosylation-inhibiting compound that preferentially targets neuronal or vascular cells and/or tissues or other specific cell or tissue types. In addition, the compounds can be specifically targeted to neuronal or vascular tissue or other specific tissue types. Targeting may be done using various delivery methods, including, but not limited to: administration to neuronal or vascular tissue or other specific target tissue, and/or the addition of one or more targeting molecules to direct the compounds of the invention to neuronal or other tissues (e.g. glial cells, nerve cells, vascular cells, etc.). Additional methods to specifically target compounds and compositions of the invention to specific tissues, such as neuronal tissues, vascular tissues, or other types of tissues may also be used with the compounds and compositions of the invention, and are known to those of ordinary skill in the art.

The invention involves, in part, compounds that inhibit O-glycosylation activity in cells, tissues, and/or subjects and use of such compounds to inhibit an O-glycosylation enzyme. The O-glycosylation inhibitors of the invention may be used for treatment of cells, tissues, and/or subjects and for research purposes. As used herein, the term "O-glycosylation activity" means the O-glycosylation of polypeptides. It is understood that hyper O-glycosylation of polypeptides, which is the O-glycosylation of polypeptides at a level above a normal level, may occur in certain diseases, including, but not limited to, diabetes and pre-diabetes conditions. The hyper O-glycosylation of polypeptides may also occur in other conditions and in other tissues as a result of disease and may result in cell and tissue damage. For example, levels of O-glycosylation (e.g., O-GlcNAcylation) that are above normal levels may result in insulin resistance.

O-glycosylation-inhibiting compounds of the invention may be administered to a subject to reduce the risk of an O-glycosylation-associated disorder. Reducing the risk of a disorder associated with above-normal O-glycosylation means using treatments and/or medications to reduce O-glycosylating enzyme activity levels and or to reduce the level or O-glycosylation of polypeptides in the subject, therein reducing, for example, the subject's risk of Alzheimer's disease; cancer; diabetes mellitus, insulin resistance, a complication of diabetes, tumorigenesis, metastasis, bacterial infection and associated complications such as sepsis, vascular complications including but not limited to: diabetic nephropathy, diabetic retinopathy, macro-vascular disease, micro-vascular disease, and diabetic neuropathy, etc.

As used herein, the term "subject" means any mammal. Subjects include but are not limited to: humans, non-human primates, cats, dogs, sheep, pigs, horses, cows, rodents such as mice, rats, etc. In some embodiments, a subject is a mammal that may be in need of treatment with an O-glycosylation-modulating compound or a glycosylase-modulating compound of the invention. In some embodiments, assays of the invention may be run in vitro and compounds that inhibit O-glycosylation may be tested and used in vitro in cells, for example in cultured cells.

As used herein the term "inhibit" with reference to O-glycosylation activity means to reduce the amount of O-glycosylating enzyme activity and/or O-glycosylation of polypeptides a level or amount that is statistically significantly less than an initial level, which may be a control level of O-glycosylation enzyme activity and/or O-glycosylation. As used herein, an initial level may be a level in a cell, tissue, or subject not contacted with an O-glycosylation-inhibiting compound of the invention. In some cases, the decrease in the level of O-glycosylation of polypeptides means the level of O-glycosylation is reduced from an initial level to a level significantly lower than the initial level. In some cases, the reduced level may be zero.

In some embodiments, a control level of O-glycosylating enzyme activity and/or O-glycosylation of polypeptides is the level that represents the normal level of O-glycosylation enzyme activity and/or O-glycosylation in a cell, tissue, and/or subject. For example, a control level may be a level that is not associated with hyper O-glycosylation and cell damage and/or death. In some instances, a control level will be the level in a disorder-free cell, tissue, or subject, that does not have abnormally high levels of O-glycosylation enzyme activity (e.g. hyper O-glycosylation activity) and/or abnormally high levels of O-glycosylation, and may be useful, for example, to monitor a change in the level of O-glycosylating enzyme activity and/or O-glycosylation in a cell. In other instances a control level of O-glycosylating enzyme activity and/or O-glycosylation will be the level in a cell, tissue, or subject with a disorder such as pre-diabetes or diabetes, etc. that is associated with O-glycosylating enzyme activity and/ or O-glycosylation, and may be useful, for example, to monitor a decrease in the level of O-glycosylating enzyme activity and/or O-glycosylation of polypeptides in a cell, tissue, or subject. In other embodiments, a control level of O-glycosylating enzyme activity and/or O-glycosylation will be the level in a cell, tissue, or subject with a disorder such as a neurodegenerative disorder, e.g. Alzheimer's disease, or cancer, etc. and may be useful, for example, to monitor a change in the level of O-glycosylating enzyme activity and/or O-glycosylation in a cell, tissue, and/or subject. These and other types of control levels are useful in assays to assess the efficacy of an O-glycosylating enzyme-activity modulating and/or O-glycosylation modulating compound of the invention.

It will be understood by one of ordinary skill in the art that a control level of O-glycosylating enzyme activity and/or O-glycosylation may be a predetermined value, which can take a variety of forms. It can be a single value, such as a median or mean. It can be established based upon comparative groups, such as in disease-free groups that have normal levels of O-glycosylating enzyme activity and/or O-glycosylation of polypeptides. Other comparative groups may be groups of subjects with specific disorders, e.g. pre-diabetes, insulin resistance, type 1 diabetes, type 2 diabetes, complications of diabetes, neurodegenerative disorders, Alzheimer's disease, cancer, etc. It will be understood that disease-free cells and/or tissues may be used as comparative groups for cells or tissues that have a O-glycosylating enzyme activity-related disorder and/or an O-glycosylation-associated disorder.

In some embodiments, a compound that inhibits and thereby reduces the level of O-glycosylating activity and/or O-glycosylation is a compound that reduces the likelihood or risk of having an O-glycosylation-associated disease or disorder. A level of O-glycosylating enzyme activity and/or O-glycosylation in a cell, tissue, and/or subject may be one that is below the O-glycosylating enzyme activity level in cells, tissues, and/or subjects with diabetes or pre-diabetes, e.g. may be a level that is clinically asymptomatic, but may still be treated and further reduced by administration of a compound of the invention. The invention relates in part to the administration of an O-glycosylation-inhibiting compound of the invention to a cell, tissue, and/or subject in an amount effective to reduce O-glycosylating enzyme activity and/or O-glycosylation of polypeptides in cells, tissues, and/or subjects with an O-glycosylation-associated disease or disorder.

Compound Analogs, Derivatives, Variants

In some aspects of the invention, O-glycosylation-modulating (inhibiting or enhancing) compounds include functional analogs, derivatives, and/or variants of the O-glycosylation-modulating compounds of the invention specifically disclosed herein. Thus, the term "O-glycosylation-modulating compounds" may include functional analogs, derivatives, and/or variants of the compounds presented herein as compounds 1-27. For example, functional analogs, derivatives, and variants of the O-glycosylation-modulating compounds of Table 1 may be made to enhance a property of a compound, such as stability. Functional analogs, derivatives, and variants of the compounds of Table 1 may also be made to provide a novel activity or property to a compound of Table 1, for example, to enhance detection, to enhance potency, to reduce side effects, etc. In some embodiments of the invention, modifications to an O-glycosylation-modulating compound of the invention can be made to the structure or side groups of the compound and can include one or more deletions, substitutions, and additions of atoms, or side groups. Alternatively, modifications can be made by addition of a linker molecule, addition of a detectable moiety, such as biotin or a fluorophore, chromophore, enzymatic, and/or radioactive label, and the like.

Analogs of the O-glycosylation-modulating compounds of Table 1 that retain some or all of the O-glycosylation-modulating properties also can be used in accordance with aspects of the invention. In some embodiments, an analog of a molecule may have a higher level of O-glycosylation-modulating activity than the original compound. Chemical groups that can be added to or substituted in the molecules include: hydrido, alkyl, alkenyl, alkynyl, cycloalkyl, heterocycyl, aryl, heteroaryl, alkoxy, aryloxy, sulfoxy, acyl, amino, acyloxy, acylamino, carboalkoxy, carboxyamido, carboxyamido, halo and thio groups. Substitutions can replace one or more chemical groups or atoms on the molecules provided herein, e.g., compounds 1-27. Examples of substituted compounds are provided in the Examples section.

Molecular terms, when used in this application, have their common meaning unless otherwise specified. The term "hydrido" denotes a single hydrogen atom (H). The term "acyl" is defined as a carbonyl radical attached to an alkyl, alkenyl, alkynyl, cycloalkyl, heterocyclyl, aryl or heteroaryl group, examples of such radicals being acetyl and benzoyl. The term "amino" denotes a nitrogen radical containing two substituents independently selected from the group consisting of hydrido, alkyl, cycloalkyl, heterocyclyl, aryl, and heteroaryl. The term "acyloxy" denotes an oxygen radical adjacent to an acyl group. The term "acylamino" denotes a nitrogen radical adjacent to an acyl group. The term "carboalkoxy" is defined as a carbonyl radical adjacent to an alkoxy or aryloxy group. The term "carboxyamido" denotes a carbonyl radical adjacent to an amino group. The term "carboxy" embraces a carbonyl radical adjacent to an alkyl, alkenyl, alkynyl, cycloalkyl, heterocyclyl, aryl or heteroaryl group. The term "halo" is defined as a bromo, chloro, fluoro or iodo radical. The term "thio" denotes a radical containing a substituent group independently selected from hydrido, alkyl, cycloalkyl, heterocyclyl, aryl and heteroaryl, attached to a divalent sulfur atom, such as, methylthio and phenylthio.

The term "alkyl" is defined as a linear or branched, saturated radical having one to about ten carbon atoms unless otherwise specified. Preferred alkyl radicals are "lower alkyl" radicals having one to about five carbon atoms. One or more hydrogen atoms of an alkyl can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of alkyl groups include methyl, tert-butyl, isopropyl, and methoxymethyl.

The term "alkenyl" embraces linear or branched radicals having two to about twenty carbon atoms, preferably three to about ten carbon atoms, and containing at least one carbon-carbon double bond. One or more hydrogen atoms of an alkenyl can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of alkenyl groups include ethylenyl or phenyl ethylenyl.

The term "alkynyl" denotes linear or branched radicals having from two to about ten carbon atoms, and containing at least one carbon-carbon triple bond. One or more hydrogen atoms of an alkynyl can also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of alkynyl groups include propynyl.

The term "aryl" denotes aromatic radicals in a single or fused carbocyclic ring system, having from five to twelve ring members. One or more hydrogen atoms of an aryl may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of aryl groups include phenyl, naphthyl, biphenyl, and terphenyl. "Heteroaryl" embraces aromatic radicals which contain one to four hetero atoms selected from oxygen, nitrogen and sulfur in a single or fused heterocyclic ring system, having from five to fifteen ring members. One or more hydrogen atoms of an heteroaryl may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of heteroaryl groups include pyridinyl, thiazolyl, thiadiazoyl, isoquinolinyl, pyrazolyl, oxazolyl, oxadiazoyl, triazolyl, and pyrrolyl groups.

The term "cycloalkyl" is defined as a saturated or partially unsaturated carbocyclic ring in a single or fused carbocyclic ring system having from three to twelve ring members. One or more hydrogen atoms of a cycloalkyl may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of a cycloalkyl group include cyclopropyl, cyclobutyl, cyclohexyl, and cycloheptyl.

The term "heterocyclyl" embraces a saturated or partially unsaturated ring containing zero to four hetero atoms selected from oxygen, nitrogen and sulfur in a single or fused heterocyclic ring system having from three to twelve ring members. One or more hydrogen atoms of a heterocyclyl may also be replaced by a substituent group selected from acyl, amino, acylamino, acyloxy, carboalkoxy, carboxy, carboxyamido, cyano, halo, hydroxy, nitro, thio, alkyl, alkenyl, alkynyl, cycloalkyl, heterocyclyl, aryl, heteroaryl, alkoxy, aryloxy, sulfoxy, and formyl. Examples of a heterocyclyl group include morpholinyl, piperidinyl, and pyrrolidinyl. The term "alkoxy" denotes oxy-containing radicals substituted with an alkyl, cycloalkyl or heterocyclyl group. Examples include methoxy, tert-butoxy, benzyloxy and cyclohexyloxy. The term "aryloxy" denotes oxy-containing radicals substituted with an aryl or heteroaryl group. Examples include phenoxy. The term "sulfoxy" is defined as a hexavalent sulfur radical bound to two or three substituents selected from the group consisting of oxo, alkyl, cycloalkyl, heterocyclyl, aryl and heteroaryl, wherein at least one of said substituents is oxo.

O-glycosylation-modulating compounds of the invention also include, but are not limited to any pharmaceutically acceptable salts, esters, or salts of an ester of each compound. Examples of salts that may be used, which is not intended to be limiting include: chloride, acetate, hydrochloride, methansulfonate or other salt of a compound of Table 1 or a functional analog, derivative, variant, or fragment of the compound.

Derivatives of the compounds of Table 1 include compounds which, upon administration to a subject in need of such administration, deliver (directly or indirectly) a pharmaceutically active O-glycosylation-modulating (e.g. inhibiting) compound as described herein. An example of pharmaceutically active derivatives of the invention includes, but is not limited to, pro-drugs. A pro-drug is a derivative of a compound that contains an additional moiety that is susceptible to removal in vivo yielding the parent molecule as a pharmacologically active agent. An example of a pro-drug is an ester that is cleaved in vivo to yield a compound of interest. Pro-drugs of a variety of compounds, and materials and methods for derivatizing the parent compounds to create the pro-drugs, are known to those of ordinary skill in the art and may be adapted to the present invention.

Analogs, variants, and derivatives of the compounds of the invention set forth in Table 1 may be identified using standard methods known to those of ordinary skill in the art. Useful methods involve identification of compounds having similar chemical structure, similar active groups, chemical family relatedness, and other standard characteristics. For the purposes of this invention, the chemical elements are identified in accordance with the Periodic Table of the Elements, CAS version, Handbook of Chemistry and Physics $75^{th}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito. 1999, the contents of which are incorporated herein by reference in their entirety.

Using the structures of the compounds disclosed herein, one of ordinary skill in the art is enabled to make predictions of structural and chemical motifs for analogs, variants, and/or derivatives that possess similar functions of the compounds disclosed in Table 1. Using structural motifs as search, evaluation, or design criteria, one of ordinary skill in the art is enabled to identify classes of compounds (functional derivatives, analogs, and/or variants of the OGT-modulating compounds) that possess the inhibitory function of the compounds disclosed herein. These compounds may be synthesized using standard synthetic methods and tested for activity as described herein. Examples of derivatives, analogs, and variants are known to those of skill in the art.

The invention also involves methods for determining the functional activity of O-glycosylation-modulating compounds described herein. The function or status of a compound as an O-glycosylation-modulating compound can be determined according to assays known and those described herein. For example, the enzyme assays described herein may be used to assess compounds for O-glycosylation-modulating ability. In addition, cell assays can be used to assess O-glycosylation-modulating ability of compounds. For example, cells can be contacted with a candidate O-glycosylation-modulating compound under conditions that produce O-glycosylation activity, and standard procedures can be used to determine whether O-glycosylating enzyme activity is modulated (e.g., inhibited or enhanced) by the compound and/or whether O-glycosylation is modulated by the candidate compound. Such methods may also be utilized to determine the status of analogs, variants, and derivatives as inhibitors of O-glycosylation enzyme activity and O-glycosylation. Although not intended to be limiting, examples of methods with which the ability of an O-glycosylation-modulating compound to modulate or change O-glycosylating enzyme activity and/or O-glycosylation can be tested, are purified enzyme assays, in vitro and in vivo assay systems provided herein in the Examples section.

Using such assays the level of O-glycosylating enzyme activity (e.g. binding and/or catalytic activity) and/or O-glycosylation can be measured in a system both before and after contacting the system with a candidate O-glycosylation-modulating compound as an indication of the effect of the compound on the level of O-glycosylating enzyme activity and/or O-glycosylation. Secondary screens may further be used to verify the efficacy of compounds identified as modulators of O-glycosylating enzyme and/or O-glycosylation. Examples of initial displacement screens and secondary screens are provided in PCT application PCT/US2007/008806, which was filed Apr. 11, 2007. It will be understood by those of ordinary skill in the art that O-glycosylating enzymes and O-glycosylation substrates that may be used in methods and assays of the invention include any suitable O-glycosylating enzymes and polypeptide substrates that can be O-glycosylated and that ones specifically disclosed herein are exemplary O-glycosylating enzymes and O-glycosylation polypeptide substrates and are not intended to be limiting.

In addition, derivatives, analogs, and variants of O-glycosylation-modulating compounds can be tested for their O-glycosylating enzyme activity modulation and/or modulation of O-glycosylation by using an activity assay (see examples). An example of an assay method, although not intended to be limiting, is a kinetic enzyme assay described herein. Such a kinetic assay may include contacting a derivative, analog, or variant of an O-glycosylation-modulating compound with a glucosyltransferase enzyme and a sugar donor (e.g., a UDP-sugar) and a polypeptide that includes (i) an O-glycosylation site, (ii) a specific protease cleavage site positioned in the polypeptide such that the rate of cleavage of the polypeptide by the specific protease at the specific protease cleavage site is different when the polypeptide is O-glycosylated at the glycosylation site than when the polypeptide is not O-glycosylated at the glycosylation site, and (iii) a detectable marker positioned in the polypeptide such that detection of the detectable marker identifies whether the polypeptide has been cleaved by the specific protease. In addition to the contacting step another step includes the addition to the contacted polypeptide of the specific protease that cleaves at the specific protease cleavage site of the polypeptide and the monitoring of the mixture of enzyme and the polypeptide for cleavage rate of the polypeptide. In such an assay, the rate of cleavage is characteristic of the level of O-glycosylation of the glycosylation site.

Other cells and tissue-based assays may include contacting a tissue or cell sample with an O-glycosylation-modulating compound and determining the compound's modulatory activity as described herein. Contacting a similar cell or tissue sample with an analog of the O-glycosylation-modulating compound, determining its activity, and then comparing the two activity results can serve as a measure of the efficacy of the derivative, variant, and/or analog's O-glycosylation-modulating activity.

In addition to the in vitro assays described above and the purified enzyme assays and other assays described in the Examples section, an in vivo assay may be used to determine the functional activity of O-glycosylation-modulating compounds described herein. In such assays, animal models of O-glycosylation-associated disease and/or disorders can be treated with an O-glycosylation-modulating compound of the invention. O-glycosylation-modulation (e.g. inhibition) may be assayed using methods described herein, which may include labeling or imaging methods. Additionally, animals with and without O-glycosylation-modulating compound treatment can be examined for behavior and/or survival as an indication of the effectiveness and/or efficacy of the compound. Behavior may be assessed by examination of symptoms of abnormal O-glycosylating enzyme activity and/or abnormal O-glycosylation of polypeptides as described herein. These measurements can then be compared to corresponding measurements in control animals. For example, test and control animals may be examined following administration of an O-glycosylation-modulating compound of the invention. In some embodiments, test animals are administered an O-glycosylation-modulating compound of the invention and control animals are not. Any resulting change in O-glycosylating enzyme activity and/or in the level of O-glycosylation of polypeptides can then be determined for each type of animal using known methods in the art such as, but not limited to, methods described herein. Such assays may be used to compare levels of O-glycosylating enzyme activity and/or O-glycosylation of polypeptides in animals administered the candidate O-glycosylation-modulating compound to control levels of O-glycosylating enzyme activity and/or O-glycosylation of polypeptides in animals not administered the O-glycosylation-modulating compound as an indication that the putative O-glycosylation-modulating compound is effective to alter (e.g. increase or decrease) O-glycosylating enzyme activity and/or O-glycosylation of polypeptides. In other embodiments, a candidate O-glycosylation-modulating compound is administered to both a test and control animal and the effect on O-glycosylating enzyme activity and/or O-glycosylation of polypeptides may be compared as a measure of the efficacy of the compound.

Once one or more O-glycosylation-modulating compounds are verified as inhibiting O-glycosylating enzyme activity and/or O-glycosylation of polypeptides using art-known assays or assays as described herein (e.g., in Examples), further biochemical and molecular techniques may be used to identify the targets of these compounds and to elucidate the specific roles that these target molecules play in the process of O-glycosylating enzyme activity and/or O-glycosylation of polypeptides in associated diseases and/or disorders. An example, though not intended to be limiting, is that the compound(s) may be labeled and contacted with a cell to identify the host cell proteins with which these compounds interact. Such proteins may be purified, e.g., by labeling the compound with an immunoaffinity tag and applying the protein-bound compound to an immunoaffinity column.

Treatment

An O-glycosylation-modulating compound of the invention (e.g., an O-glycosylation inhibitor) may be used to treat a subject with an O-glycosylation-associated disease or disorder. As used herein, the term "treat" includes active treatment of a subject that has an OGT disease or disorder (e.g., a subject diagnosed with such a condition) and also includes prophylactic treatment of a subject who is has not yet been diagnosed. Compounds of the invention may be administered prophylactically to a subject at risk of an O-glycosylation-associated disorder or disorder. Determination of a subject at risk for an O-glycosylation-associated disease or disorder, and/or the determination of a diagnosis of an O-glycosylation-associated disease or disorder in a subject, may be done by one of ordinary skill in the art using routine methods.

An O-glycosylation-modulating compound of the invention may be delivered to a cell using standard methods known to those of ordinary skill in the art. Various techniques may be employed for introducing O-glycosylation-modulating compounds of the invention to cells, depending on whether the compounds are introduced in vitro or in vivo in a host.

When administered, the O-glycosylation-modulating compounds (also referred to herein as therapeutic compounds and/or pharmaceutical compounds) of the present invention are administered in pharmaceutically acceptable preparations. Such preparations may routinely contain pharmaceutically acceptable concentrations of salt, buffering agents, preservatives, compatible carriers, and optionally other therapeutic agents.

The term "pharmaceutically acceptable" carrier means a non-toxic material that does not interfere with the effectiveness of the biological activity of the active ingredients. The characteristics of the carrier will depend on the route of administration.

The therapeutics of the invention can be administered by any conventional route, including injection or by gradual infusion over time. The administration may for example, be oral, intravenous, intraperitoneal, intrathecal, intramuscular, intranasal, intracavity, subcutaneous, intradermal, mucosal, transdermal, or transdermal.

The therapeutic compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the therapeutic agent into association with a liquid carrier, a finely divided solid carrier, or both, and then, if necessary, shaping the product.

Compositions suitable for parenteral administration conveniently comprise a sterile aqueous preparation of the therapeutic agent, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Compositions suitable for oral administration may be presented as discrete units such as capsules, cachets, tablets, or lozenges, each containing a predetermined amount of the therapeutic agent. Other compositions include suspensions in aqueous liquors or non-aqueous liquids such as a syrup, an elixir, or an emulsion.

In some embodiments of the invention, an O-glycosylation-modulating compound of the invention may be delivered in the form of a delivery complex. The delivery complex may deliver the O-glycosylation-modulating compound into any cell type, or may be associated with a molecule for targeting a specific cell type. Examples of delivery complexes include an O-glycosylation-modulating compound of the invention associated with: a sterol (e.g., cholesterol), a lipid (e.g., a cationic lipid, virosome or liposome), or a target cell specific binding agent (e.g., an antibody, including but not limited to monoclonal antibodies, or a ligand recognized by target cell specific receptor). Some complexes may be sufficiently stable in vivo to prevent significant uncoupling prior to internalization by the target cell. However, the complex can be cleavable under appropriate conditions within the cell so that the O-glycosylation-modulating compound is released in a functional form.

An example of a targeting method, although not intended to be limiting, is the use of liposomes to deliver an O-glycosylation-modulating compound of the invention into a cell. Liposomes may be targeted to a particular tissue, such neuronal cells, or other cell type, by coupling the liposome to a specific ligand such as a monoclonal antibody, sugar, glycolipid, or protein. Examples of neuronal cells include, but are not limited to hippocampal cells. Such proteins include proteins or fragments thereof specific for a particular cell type, antibodies for proteins that undergo internalization in cycling, proteins that target intracellular localization and enhance intracellular half life, and the like.

For certain uses, it may be desirable to target the compound to particular cells, for example specific neuronal cells, including specific tissue cell types, e.g. tissue-specific nervous system cells. In some embodiments, it may be desirable to target an O-glycosylation-modulating compound to another cell type, including, but not limited to, cardiac cells, pancreatic cells, vascular cells, etc. In such instances, a vehicle (e.g. a liposome) used for delivering an O-glycosylation-modulating compound of the invention to a cell type (e.g. a neuronal cell, vascular cell, etc.) may have a targeting molecule attached thereto that is an antibody specific for a surface membrane polypeptide of the cell type or may have attached thereto a ligand for a receptor on the cell type. Such a targeting molecule can be bound to or incorporated within the O-glycosylation-modulating compound delivery vehicle. Where liposomes are employed to deliver an O-glycosylation-modulating compound of the invention, proteins that bind to a surface membrane protein associated with endocytosis may be incorporated into the liposome formulation for targeting and/or to facilitate uptake.

Liposomes are commercially available from Invitrogen, for example, as LIPOFECTIN™ and LIPOFECTACE™, which are formed of cationic lipids such as N-[1-(2,3 dioleyloxy)-propyl]-N,N, N-trimethylammonium chloride (DOTMA) and dimethyl dioctadecylammonium bromide (DDAB). Methods for making liposomes are well known in the art and have been described in many publications.

The invention provides a composition of the above-described agents for use as a medicament, methods for preparing the medicament and methods for the sustained release of the medicament in vivo. Delivery systems can include time-release, delayed release or sustained release delivery systems. Such systems can avoid repeated administrations of the therapeutic agent of the invention, increasing convenience to the subject and the physician. Many types of release delivery systems are available and known to those of ordinary skill in the art. They include, but are not limited to, polymer-based systems such as polylactic and polyglycolic acid, poly(lactide-glycolide), copolyoxalates, polyanhydrides, polyesteramides, polyorthoesters, polyhydroxybutyric acid, and polycaprolactone. Microcapsules of the foregoing polymers containing drugs are described in, for example, U.S. Pat. No. 5,075,109. Nonpolymer systems that are lipids including sterols such as cholesterol, cholesterol esters and fatty acids or neutral fats such as mono-, di- and tri-glycerides; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In one particular embodiment, the preferred vehicle is a biocompatible microparticle or implant that is suitable for implantation into the mammalian recipient. Exemplary bioerodible implants that are useful in accordance with this method are described in PCT International application no. WO 95/24929, entitled "Polymeric Gene Delivery System". describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the compound(s) of the invention is encapsulated or dispersed within the biocompatible, preferably biodegradable polymeric matrix disclosed in WO 95/24929. The polymeric matrix preferably is in the form of a microparticle such as a microsphere (wherein the compound is dispersed throughout a solid polymeric matrix) or a microcapsule (wherein the compound is stored in the core of a polymeric shell). Other forms of the polymeric matrix for containing the compounds of the invention include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used. The polymeric matrix composition can be selected to have both favorable degradation rates and also to be formed of a material which is bioadhesive, to further increase the effectiveness of transfer when the device is administered to a vascular surface. The matrix composition also can be selected not to degrade, but rather, to release by diffusion over an extended period of time.

Both non-biodegradable and biodegradable polymeric matrices can be used to deliver agents and compounds of the invention of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the agents and/or compounds of the invention are delivered using the bioerodible implant by way of diffusion, or by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic kid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein by reference, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

Use of a long-term sustained release implant may be particularly suitable for treatment of subjects with an established neurological disorder or complication of diabetes as well as subjects at risk of developing a neurological disorder, insulin resistance, pre-diabetes, diabetes, or a complication of diabetes.

"Long-term" release, as used herein, means that the implant is constructed and arranged to deliver therapeutic levels of the active ingredient for at least 7 days, and preferably 30-60 days, and most preferably months or years. The implant may be positioned at or near the site of the neurological damage or the area of the brain or nervous system affected by or involved in the neurodegenerative disorder. Long-term release implants may also be used in non-neuronal tissues and organs to allow regional administration of an OGT-modulating compound of the invention. Long-term sustained release implants are well known to those of ordinary skill in the art and include some of the release systems described above.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The preparations of the invention are administered in effective amounts. An effective amount is that amount of a pharmaceutical preparation that alone, or together with further doses, stimulates the desired response. In the case of treating a disorder or condition that is associated with abnormal O-glycosylating enzyme activity and/or abnormal O-glycosylation of polypeptides, desired response is reducing the onset, stage or progression of the abnormal O-glycosylating enzyme activity and/or O-glycosylation of polypeptides and associated effects. This may involve only slowing the progression of the damage temporarily, although more preferably, it involves halting the progression of the damage permanently. An effective amount for treating abnormal O-glycosylating enzyme activity and/or O-glycosylation of polypeptides is that amount that alters (increases or reduces) the amount or level of O-glycosylating enzyme activity and/or O-glycosylation of polypeptides, when the cell or subject is a cell or subject with an O-glycosylation-associated disease or disorder, with respect to that amount that would occur in the absence of the active compound.

The invention involves, in part, the administration of an effective amount of an O-glycosylation-modulating compound of the invention. The O-glycosylation-modulating compounds of the invention are administered in effective amounts. Typically effective amounts of an O-glycosylation-modulating compound will be determined in clinical trials, establishing an effective dose for a test population versus a control population in a blind study. In some embodiments, an effective amount will be that amount that diminishes or eliminates an O-glycosylation-associated disease or disorder and its effects in a cell, tissue, and/or subject. Thus, an effective amount may be the amount that when administered reduces the amount of cell and or tissue damage and/or cell death from the amount that would occur in the subject or tissue without the administration of a O-glycosylation-modulating compound of the invention.

The pharmaceutical compound dosage may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days. It will be recognized by those of skill in the art that some of the O-glycosylation-modulating compounds may have detrimental effects at high amounts. Thus, an effective amount for use in the methods of the invention may be optimized such that the amount administered results in minimal negative side effects and maximum O-glycosylation modulation.

The absolute amount will depend upon a variety of factors, including the material selected for administration, whether the administration is in single or multiple doses, and individual subject parameters including age, physical condition, size, weight, and the stage of the disease or disorder. These factors are well known to those of ordinary skill in the art and can be addressed with no more than routine experimentation.

The pharmaceutical compounds of the invention may be administered alone, in combination with each other, and/or in combination with other drug therapies that are administered to subjects with O-glycosylation-associated diseases. Additional drug therapies (for active treatment and/or prophylaxis) that may be administered with pharmaceutical compounds of the invention include, art-known methods of O-glycosylation-associated disorders such as treatments for diabetes, complications of diabetes, insulin resistance, neurodegenerative disease, cancer, etc. Alternative drug therapies are known to those of ordinary skill in the art and are administered by modes known to those of skill in the art. The drug therapies are administered in amounts that are effective to achieve the physiological goals (to reduce symptoms and damage from O-glycosylation-associated disease or disorder in a subject, e.g. cell damage and/or cell death), in combination with the pharmaceutical compounds of the invention. Thus, it is contemplated that the alternative drug therapies may be administered in amounts that are not capable of preventing or reducing the physiological consequences of the O-glycosylation-associated disease and/or disorder when the drug therapies are administered alone, but which are capable of preventing or reducing the physiological consequences of an O-glycosylation-associated disease and/or disorder when administered in combination with one or more O-glycosylation-modulating compounds of the invention.

Examples of alternative drug therapies for regulating blood sugar levels, e.g. therapies for pre-diabetes and/or diabetes, include oral therapies with hypoglycemic agents an/or oral anti-diabetic agents, injectable therapies, and the like. Non-drug therapies for regulating blood sugar level include, but are not limited to, diatetic and/or exercise control measures.

Diet and exercise alterations include, but are not limited to, reducing caloric intake, and/or increasing fiber intake, and/or decreasing fat intake, and/or increasing exercise level.

Oral drug therapies for regulating blood sugar levels include hypoglycemic agents that may include, but are not limited to: Acarbose; Acetohexamide; Chlorpropamide; Darglitazone Sodium: Glimepiride; Glipizide; Glyburide, Repaglinide; Troglitazone; Tolazamide; Tolbutamide.

Oral drug therapies for regulating blood sugar levels include antidiabetic agents that may include but are not limited to: Acarbose, Acetohexamide; Buformin; Butoxamine Hydrochloride; Camiglibose; Chlorpropamide; Ciglitazone; Englitazone Sodium; Etoformin Hydrochloride; Gliamilide; Glibornuride; Glicetanile Gliclazide Sodium; Gliflumide; Glipizide; Glucagon; Glyburide; Glyhexamide; Glymidine Sodium; Glyoctamide; Glyparamide; Insulin; Insulin, Dalanated; Insulin Human; Insulin Human, Isophane; Insulin Human Zinc; Insulin Human Zinc, Extended; Insulin, Isophane; Insulin Lispro; Insulin, Neutral; Insulin Zinc; Insulin Zinc, Extended; Insulin Zinc, Prompt; Linogliride; Linogliride Fumarate; Metformin; Methyl Palmoxirate; Palmoxirate Sodium; Pioglitazone Hydrochloride; Pirogliride Tartrate; Proinsulin Human; Repaglinide; Seglitide Acetate; Tolazamide; Tolbutamide; Tolpyrramide; Troglitazone; Zopolrestat.

Injectable therapies for regulating blood sugar levels may include, but are not limited to:
Fast-Acting Insulin:
  Insulin Injection: regular insulin; Prompt Insulin Zinc Suspension; Semilente® insulin. These categories include preparations such as: Humalog® Injection; Humulin® R; Iletin II; Novolin R, Purified Pork Regular Insulin; Velosulin BR Human Insulin;
Intermediate-Acting Insulin:
  Isophane Insulin Suspension: NPH insulin, isophane insulin; Insulin Zinc Suspension Lente® Insulin. These categories include preparations such as: Humulin® L; Humulin® R; Humulin® N NPH; Iletin® II, Lente®; Iletin® II, NPH; Novolin® L, Novolin® N, Purified Pork Lente® insulin, Purified Pork NPH isophane isulin;
Intermediate and Rapid-Acting Insulin Combinations:
  Human Insulin Isophane Suspension/Human Insulin Injection. This category includes preparations such as: Humulin® 50/50; Humulin®70/30; Novolin®70/30
Long-Acting Insulin:
Protamine Zinc Insulin Suspension; Extended Insulin Zinc Suspension. These categories include preparations such as: Ultralente® Insulin, Humulin® U.

Diagnostic tests known to those of ordinary skill in the art may be used to assess the level of O-glycosylating enzyme activity and/or O-glycosylation of polypeptides in a subject and the effects thereof, and to evaluate a therapeutically effective amount of a pharmaceutical compound administered. Examples of diagnostic tests are set forth below. A first determination of O-glycosylating enzyme activity and/or the effects thereof in a cell and/or tissue may be obtained using one of the methods described herein (or other methods known in the art), and a second, subsequent determination of the level of O-glycosylating enzyme activity. A comparison of the O-glycosylating enzyme activity and/or O-glycosylation of polypeptides and/or the effects thereof on the subject at the different time points may be used to assess the effectiveness of administration of a pharmaceutical compound of the invention as a prophylactic or an active treatment of the O-glycosylation-associated disease or disorder. Family history or prior occurrence of an O-glycosylation-associated disease or disorder, even if the O-glycosylation-associated disease or disorder is absent in a subject at present, may be an indication for prophylactic intervention by administering a pharmaceutical compound described herein to reduce or prevent abnormal O-glycosylating enzyme activity and/or abnormal O-glycosylation of polypeptides.

An example of a method of diagnosis of abnormal O-glycosylating enzyme activity and/or abnormal O-glycosylation of polypeptides that can be performed using standard methods such as, but not limited to: imaging methods, electrophysiological methods, blood tests, and histological methods. Additional methods of diagnosis and assessment of OGT-associated disease or disorders and the resulting cell death or damage are known to those of skill in the art.

In addition to the diagnostic tests described above, clinical features of O-glycosylation-associated diseases and/or disorders can be monitored for assessment of O-glycosylating enzyme activity following onset of an O-glycosylation-associated disease or disorder. These features include, but are not limited to: assessment of the presence of cell damage, cell death, neuronal cell lesions, brain lesions, organ lesions, abnormal cell growth, vascular damage, blood abnormalities, sugar processing abnormalities, and behavioral abnormalities. Such assessment can be done with methods known to one of ordinary skill in the art, such as behavioral testing, blood testing, and imaging studies, such as radiologic studies, CT scans, PET scans, etc.

Kits

The invention also provides a pharmaceutical kit comprising one or more containers comprising one or more O-glycosylation-modulating compounds of the invention and/or formulations or compositions of the invention. The kit may also include instructions for the use of the one or more O-glycosylation-modulating compounds or formulations of the invention for the treatment of an O-glycosylation-associated disease or disorder. The kits of the invention may also comprise one or more containers containing additional drugs for treating an O-glycosylation-associated disease or disorder. The invention also includes in some aspects, kits for testing candidate compounds to assess their ability to inhibit O-glycosylating enzyme activity.

The invention will be more fully understood by reference to the following examples. These examples, however, are merely intended to illustrate the embodiments of the invention and are not to be construed to limit the scope of the invention.

EXAMPLES

Introduction

Preparation of polypeptide substrates and their use in assays for glycosylation modulators.

Example 1

Synthesis of Polypeptide Substrates

A polypeptide substrate was identified that satisfied three requirements: 1) the peptide had to be a good substrate for O-Linked N-acetylglucosaminyltransferase (OGT); 2) there must have been a large difference in the rate of proteolysis between glycosylated and unglycosylated peptide; and 3) the composition/location of the FRET pair on the polypeptide must have yielded a large change in signal upon proteolysis.

Figures 1, 2:
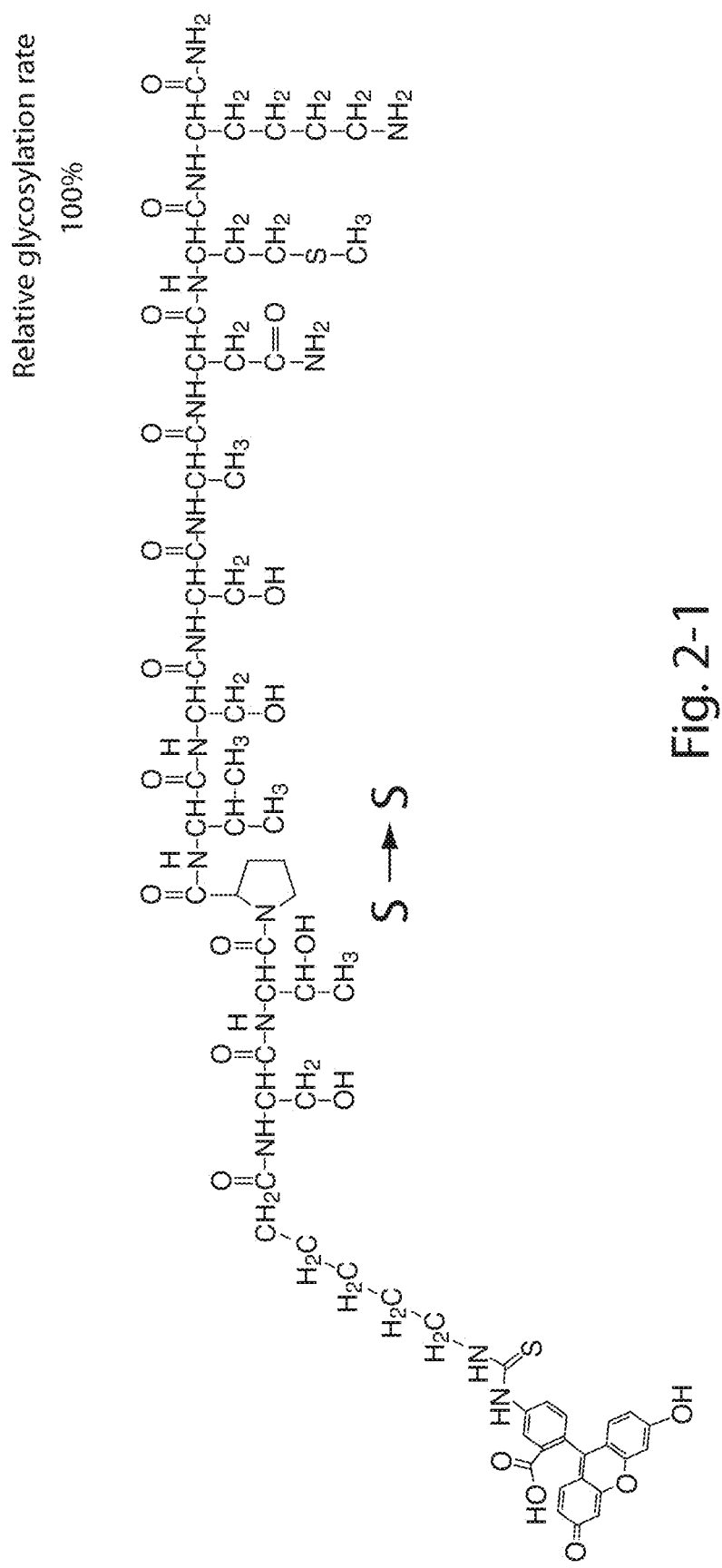
FIG. 2 shows structures of polypeptides 4.1, 4.4, and 4.5 and their relative glycosylation rate with polypeptide 4.1 having as the natural (wild-type) sequence having a glycosylation rate of 100%. (Polypeptide 4.1 S→S (SEQ ID NO:1); Polypeptide 4.2 S→F (SEQ ID NO:2); Polypeptide 4.5 S→R (SEQ ID NO:3)).
Figure 2:
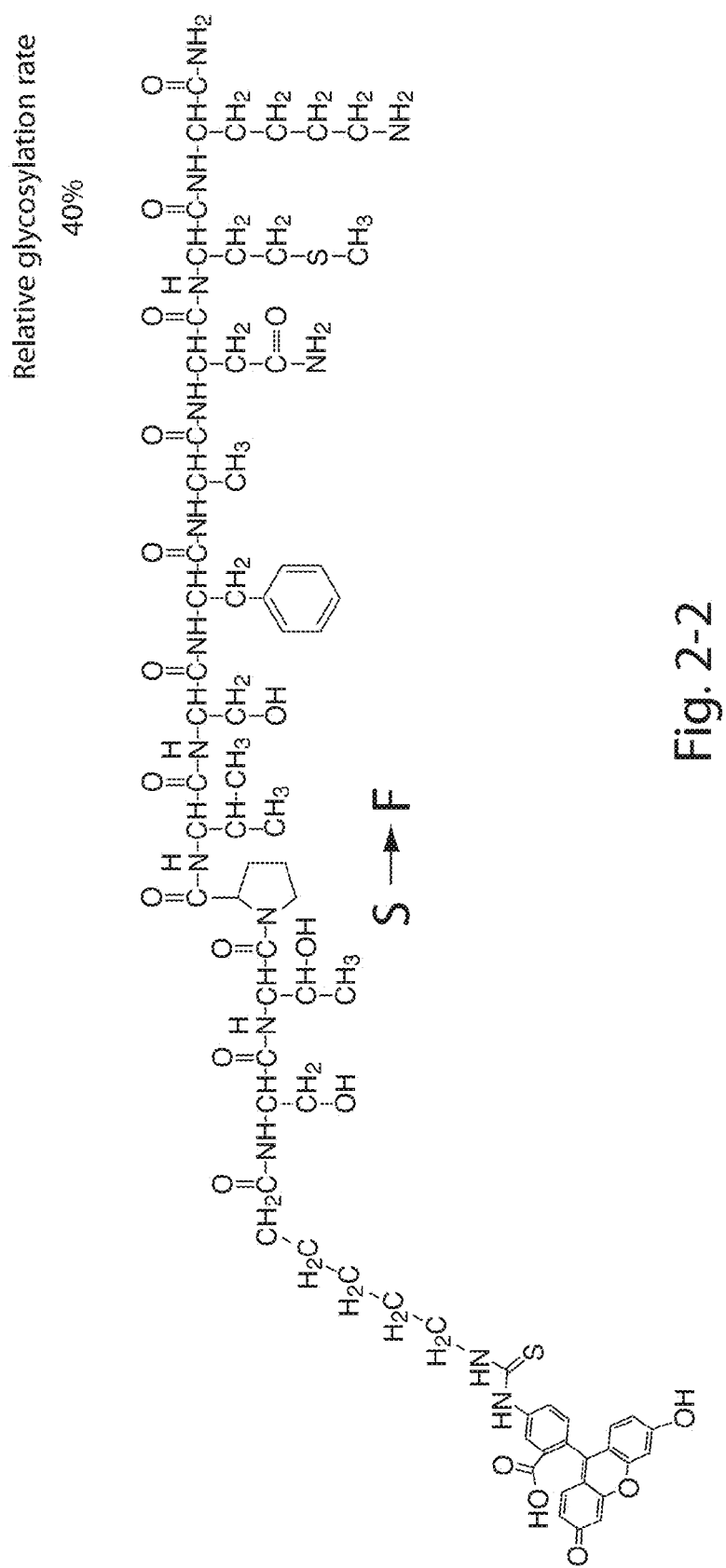

To address the first requirement, a panel of polypeptides was synthesized based on a truncated version of the CKII polypeptide [CKII peptide PGGSTPVSSNAMM (SEQ ID NO:20)]. The polypeptide was modified from the native sequence in several ways. First, a fluorescein was installed on the N-terminus during synthesis. Second, a lysine was added to the C-terminus so that a second dye or quencher could be installed by reaction with the appropriate N-hydroxysuccinimidyl ester. These modifications allowed two different FRET approaches. The first approach required the installation of a coumarin derivative on the polypeptide. The second required installation of a quencher molecule, which measured total fluorescence intensity. (See Examples 2 and 3). Finally, the residues on either side of the glycosylated serine of the truncated CK2 polypeptide were changed to phenylalanine, leucine or arginine to introduce proteolytic cleavage sites for common proteases (such as trypsin, chymotrypsin and thermolysin) that were not present in the native sequence. It was reasoned that cleavage adjacent to the glycosylation site would yield the largest difference in the rate of proteolysis between glycosylated and native polypeptides. This series of polypeptides was synthesized and screened for OGT activity using by LC/MS. Peak integration (measured at 445 nm) was used to quantitative products and reactants and mass spectrometry was used to confirm peak identity. The results are presented in Table 2 and some of the peptides (peptide 4.1, 4.4, and 4.5 top to bottom) are illustrated in FIG. 2.

TABLE 2

Peptide derivatives of CK2. Mutated residues are shown in italics and the glycolsylated serine is bold.

| polypeptide | mutation | sequence | Relative rate of glycosylation |
|---|---|---|---|
| 4.1 | wt | FITC(Aha)STPVSSANMK (SEQ ID NO: 7) | 1 |
| 4.2 | V → F | FITC(Aha)STP*F*SSANMK (SEQ ID NO: 8) | 0.15 |
| 4.3 | V → R | FITC(Aha)STP*R*SSANMK (SEQ ID NO: 9) | 0 |
| 4.4 | S → F | FITC(Aha)STPVS*F*ANMK (SEQ ID NO: 10) | 0.4 |
| 4.5 | S → R | FITC(Aha)STPVS*R*ANMK (SEQ ID NO: 11) | 0.7 |

The most striking result from this panel was that all polypeptides lacking the valine residue N-terminal to the glycosylated serine were poor glycosyl acceptors. This result experimentally confirmed one aspect of OGT acceptor sequence specificity that had been recently proposed based on data from the growing O-GlcNAcome—that a beta-branched amino acid directly N-terminal to the glycosylated serine is favored in the polypeptide acceptor sequence[25]. It also appeared that OGT tolerated significant variation in the position C-terminal to the glycosylated residue, accepting both phenylalanine and arginine with little loss of activity. Polypeptides 4.1, 4.4, and 4.5 were then derivatized at the ε—$NH_2$ of the C-terminal lysine with the FRET donor 7-diethylaminocoumarin-3-carboxylic acid (DEAC) using the commercially available NHS ester derivative, resulting in polypeptides 4.6-4.8. These molecules were purified using RP-HPLC, enzymatically glycosylated, then screened for cleavage using a variety of proteases.

TABLE 3

DEAC modified polypeptide derivatives of CKII. Mutated residues are shown in italics and the glycolsylated serine is bold.

| peptide | mutation | sequence |
|---------|----------|----------|
| 4.6 | Wt | FITC(Aha)STPVSSANMK(DEAC) (SEQ ID NO: 12) |
| 4.7 | S → F | FITC(Aha)STPVS*F*ANMK(DEAC) (SEQ ID NO: 13) |
| 4.8 | S → R | FITC(Aha)STPVS_R_ANMK(DEAC) (SEQ ID NO: 14) |

Coumarin excitation (ex=400 nm) and subsequent emission (em=472 nm) in an intact polypeptide will efficiently excite a fluorescein analog (ex=485 nm), resulting in both coumarin (472 nm) and fluorescein (525 nm) emission. When the polypeptide was cut, the amount of fluorescein excitation (and subsequent fluorescein emission) was greatly reduced, resulting in a large change in 535 nm/460 nm emission ratio. One advantage of this readout was that the ratiometric response was independent of changes in volume and even small changes in FRET-probe concentration[21].

The glycosylated and unglycosylated polypeptides were proteolysed with serial dilutions of trypsin, chymotrypsin, proteinase K, and thermolysin. All proteolysis led to a large (15-fold) and similar change in emission ratio, however only Proteinase K showed a large difference in the rate of proteolysis between glycosylated and unglycosylated polypeptides, cutting the unglycosylated polypeptides 4.6 and 4.8~100-500 times faster than the corresponding glycosylated polypeptides. The resulting assay window (defined as the area in between the curve for the glycosylated and unglycosylated polypeptide, (FIG. 3) is very large and is roughly the same for both 4.6 and 4.8.

Figures 2, 3:
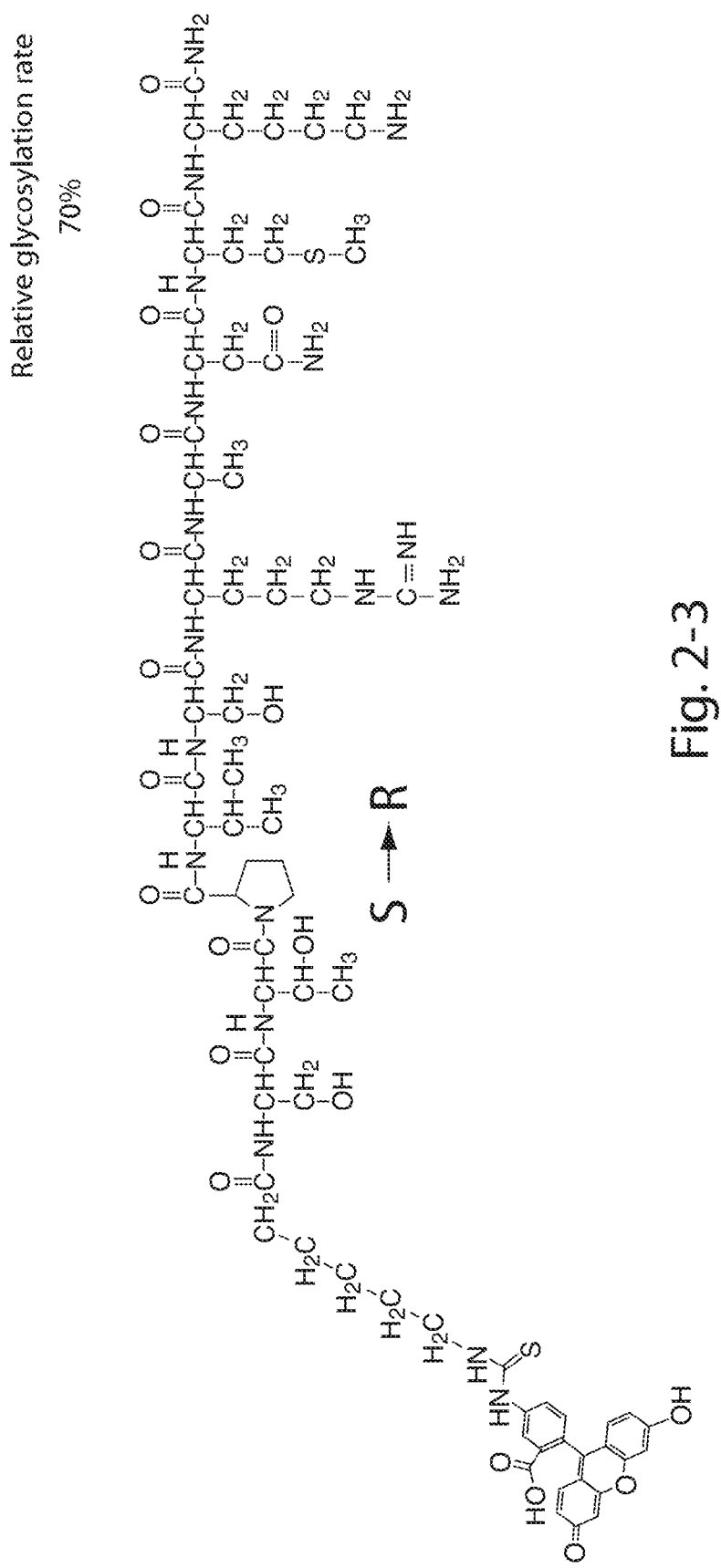
FIG. 3 shows graphs demonstrating proteolysis of glycosylated (squares) and un-glycosylated (diamonds) polypeptide 4.8 (SEQ ID NO: 3). Proteolysis with serial dilutions of trypsin (FIG. 3B) and proteinase K (FIG. 3A) are shown, with the cleavage site of each peptide shown above (FITC-AhaSTPV (SEQ ID NO:21); SRANMK-DEAC (SEQ ID NO:22); FITC-AhaSTPVSR (SEQ ID NO:23); ANMK-DEAC (SEQ ID NO: 24). The x-axis of both graphs is mg/mL protease concentration and the y-axis is the 535/460 emission ratio.
Figure 3A:
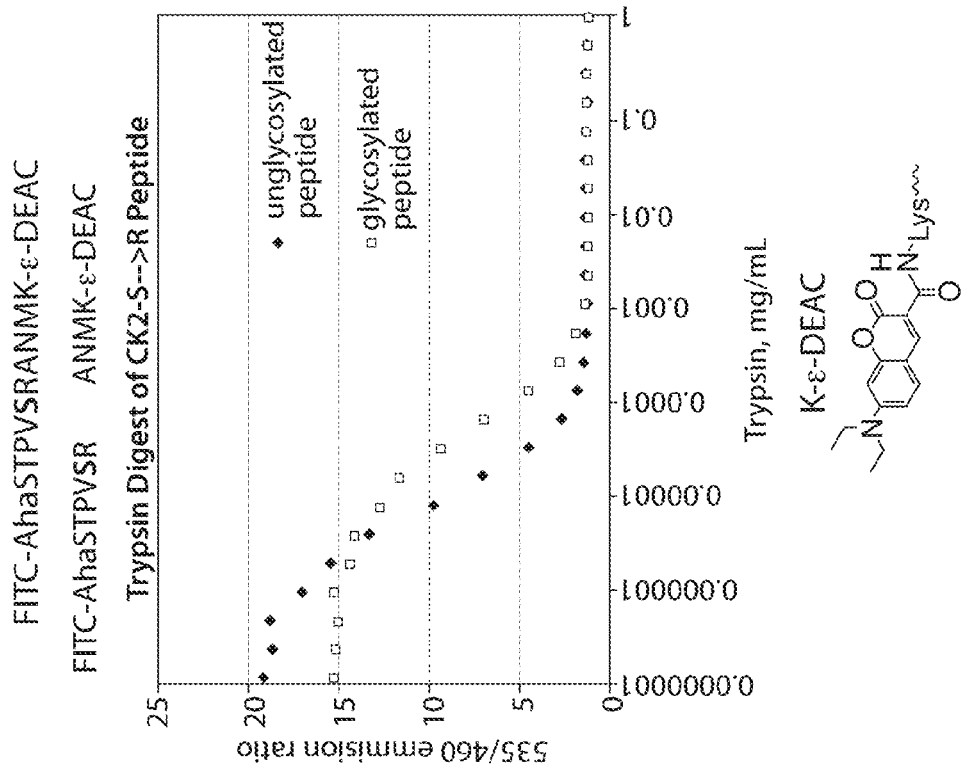
Figure 3B:
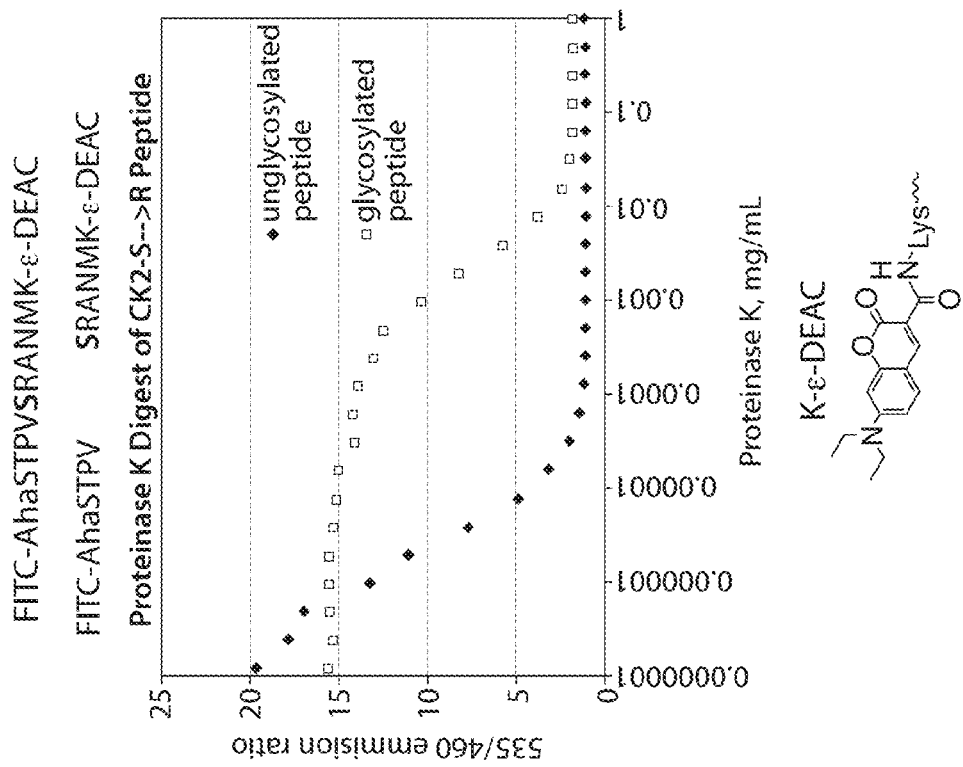

This was an unexpected and fortuitous result. It was anticipated that cleavage would occur at the protease site designed into the polypeptide (i.e. after the arginine for trypsin or the phenylalanine for chymotrypsin) and therefore would not be directly adjacent to the glycosylated serine. This increase of one residue from the glycoserine resulted in a greatly reduced difference in proteolytic rate between the glycosylated and unglycosylated polypeptide, as can be seen in the trypsin digest (FIG. 3). Although the substrate specificity for proteinase K is somewhat ambiguous, the enzyme is known to cleave C-terminal to hydrophobic residues such as valine. The large difference in cleavage rate, indicative of cleavage directly adjacent to the glycosylated residue, as well as the fact that both 4.6 and 4.8 have similar assay windows led to the conclusion that proteinase K was cleaving after the valine, which was confirmed by analysis of the cleavage products by LC/MS.

From FIG. 3, the concentration of proteinase K that gives the largest assay window could be estimated; under the conditions above this value is ~50 ng/mL. Using this concentration of protease, several hundred positive (BSA) and negative (OGT) control wells were analyzed and a Z' of 0.95 was calculated. This is the highest Z' of any assay piloted at the ICCB (Harvard University, Boston, Mass.)[26].

Before high-throughput screening, it was necessary to address several concerns regarding the use of the DEAC/HTC label pair. Autofluorescence of library members can be problematic in screening as they lead to false positives. Unlike a fluorescence polarization assay, there is no way to identify autofluorescent compounds during data analysis with a FRET or fluorescence intensity readout, so the effects of compound autofluorescence are beneficially reduced during assay development. The use of DEAC was concerning for two reasons. First, the DEAC requires excitation at 400 nm, which is significantly blue-shifted compared to fluorescein excitation at 485 nm, indicating that autofluorescence could be more problematic than in the previous assay. The coumarin core, many of which will likely be as fluorescent as the derivate used in the FRET polypeptide, is present in 1.5% of the compounds in the ICCB libraries. Second, although the FRET polypeptide was used at quite high fluorophore concentrations (5 µM) during assay development, the planned final assay volume (20 µL) and pin transfer volume of inhibitor (100 nL) corresponds to an average inhibitor concentration of ~70 µM. Thus, compounds with a ten-fold lower quantum yield and/or extinction coefficient than DEAC would likely yield significant interference.

Figure 4:
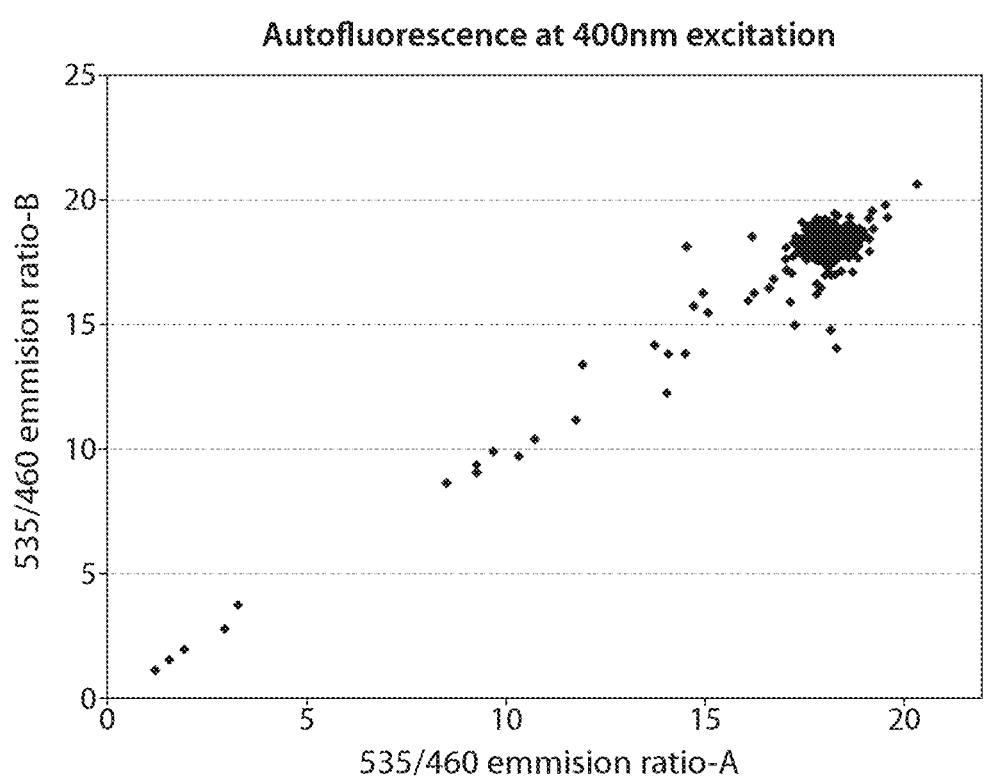
FIG. 4 shows a scatter plot of 535/460 emission ratio of polypeptide 4.5 in the presence of known bioactive small molecules. The drop in ratio for ~5% of these compounds is dues to compound autofluorescence.

To test for autofluorescence, 100 nL of ICCB plate 1364 (a mixture of commercially available known bioactive compounds) was pin transferred in duplicate into 20 µL of a 5 µM solution of polypeptide 4.8 in buffer and the plates were read at 460 nm and 535 nm. These compounds are structurally diverse and represented the spectral characteristics of the larger libraries. A scatter plot of the duplicate 535 nm/460 nm ratio (FIG. 4) revealed that roughly 5% of these compounds reproducibly autofluoresced near 460 nm, and would be registered as positive in a high-throughput assay (since increased 460 nm emission will result in a decrease in the 535 nm/460 nm ratio).

Peptide Synthesis:
All polypeptides were purchased from Tufts University core facility (Boston, Mass.). The mass of crude product was verified and the polypeptides were labeled under the following conditions: Polypeptide was dissolved in 250 mM NaHCO$_3$ buffer, pH 8.2 at a 5 mM concentration and the appropriate NHS-Ester (0.5 eq) was dissolved in DMSO (a volume of 1/10 of the aqueous buffer was used). The DMSO solution was quickly added to the peptide and the reaction proceeded at room temperature for 30 minutes. This was repeated 2 more times (four more times for polypeptide 4.10). The reaction was monitored by LC/MS. LCMS conditions for polypeptides 4.1-4.8—Agilent Eclipse 5 µm XD8-C8 column, 0→100% CH$_3$CN+0.1% formic acid over 20 minutes. LCMS conditions for polypeptides 4.9-4.10—Agilent Eclipse 5 µm XD8-C8 column, 0→100% CH$_3$CN+0.1% NH$_4$OH over 20 minutes. Each polypeptide was purified by preparative HPLC. Conditions for polypeptides 4.1-4.8 were: —Phenomonex Luna C18 5 µm column, 0→100% CH$_3$CN+0.1% TFA over 40 minutes. Conditions for polypeptides 4.9-4.10 were: —Phenomonex Luna C18 5 µm column, 0→100% CH$_3$CN+0.1% NH$_4$OH over 40 minutes. Products were confirmed by LC/MS.

Preparative Glycosylation of Labeled Polypeptides:
Purified FRET labeled polypeptides were added (20-50 µM final concentration) to assay buffer (50 mM Tris, 20 mM CaCl$_2$, 0.05% Tween-20, 0.05% NP-40, pH=7.8), 200 µM UDP-GlcNAc, 0.05 units of alkaline phosphatase, and 5 µM OGT. Reactions were monitored using LCMS: conditions for polypeptides 4.1-4.8—Agilent Eclipse 5 µm XD8-C8 column, 10→60% CH$_3$CN+0.1% formic acid over 20 minutes. LCMS conditions for polypeptides 4.9-4.10—Agilent Eclipse 5 µm XD8-C8 column, 10→60% CH$_3$CN+0.1% NH$_4$OH over 20 minutes, and when complete were purified using the same column and conditions. Polypeptides 4.1-4.8 were quantitated by absorption at 492 nm using an extinction coefficient of 86,000 cm$^{-1}$M$^{-1}$; polypeptide 4.9 was quantitated by absorption at 530 nm using an extinction coefficient of 26,000 cm$^{-1}$M$^{-1}$; polypeptide 4.10 was quantitated by absorption at 530 nm using an extinction coefficient of 52,000 cm$^{-1}$M$^{-1}$.

Fluorescence Resonance Energy Transfer (FRET)-Peptide Approach #1

Figure 5:
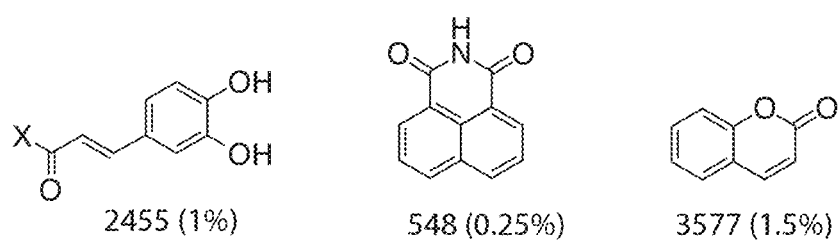
FIG. 5 shows three large classes of autofluorescent compounds. The number and percentage below each compound is the number of members of each class represented in the ICCB library and percent of the total library. X═C,O,N.

This approach required the installation of a coumarin derivative on the polypeptide. Given that the ICCB cherry pick limit of 0.2%, autofluorescence at a frequency of 1 compound in 1000 would result in roughly 50% of the compound picked would be false positives. Use of the coumarin/FITC pair resulted in 50-fold more autofluorescence than this upper limit, requiring adaptation of the assay. One possibility was to add an additional read step in between compound transfer and proteolysis. Although this would successfully identify autofluorescent compounds, it would also eliminate data for ~5% of the library members, which include entire structural classes (FIG. 5). Due to concerns that the elimination of such a large number of compounds would adversely affect the number of OGT inhibitors identified, the FRET pair was adjusted to reduce the number of compounds that autofluoresce.

Fluorescence Resonance Energy Transfer (FRET)-Peptide Approach #2

An alternative FRET strategy, the use of a donor/quencher pair was employed (FIG. 1). The readout using a quencher approach was raw fluorescence and was not ratiometric, thus the signal was subject to well-to-well volume variations introduced during liquid handling. Given the high Z' and excellent signal-to-noise of this assay, it was reasoned that a 3-5% variation from liquid handling would not be detrimental. The syntheses of the donor/quencher polypeptides 4.9 and 4.10 was undertaken and involved a one step coupling of QXL™ 520 acid-SE (Anaspec, San Jose, Calif.) with the ε-NH2 of the C-terminal lysine. Some solubility issues were observed with polypeptides 4.6-4.8, prompting the synthesis of a more soluble variant, polypeptide 4.10. Improved polypeptide solubility increased the glycosylation rate by 2-3 fold. In addition to improved solubility, polypeptide 4.10 had two modified QXL™ 520 lysine residues. It was hypothesized that adding a second quencher would increase the change in RFU when the polypeptide was cut. A small increase in window size was observed, but the difference was marginal. The assay windows of both polypeptides were similar to that of the corresponding DEAC/FITC polypeptides 4.6 and 4.8, though the optimal proteinase K concentration was five-fold lower (~10 ng/mL). Several hundred positive (BSA) and negative (OGT) control wells were assayed with these polypeptides, yielding Z' values of ~0.90.

Figure 6:
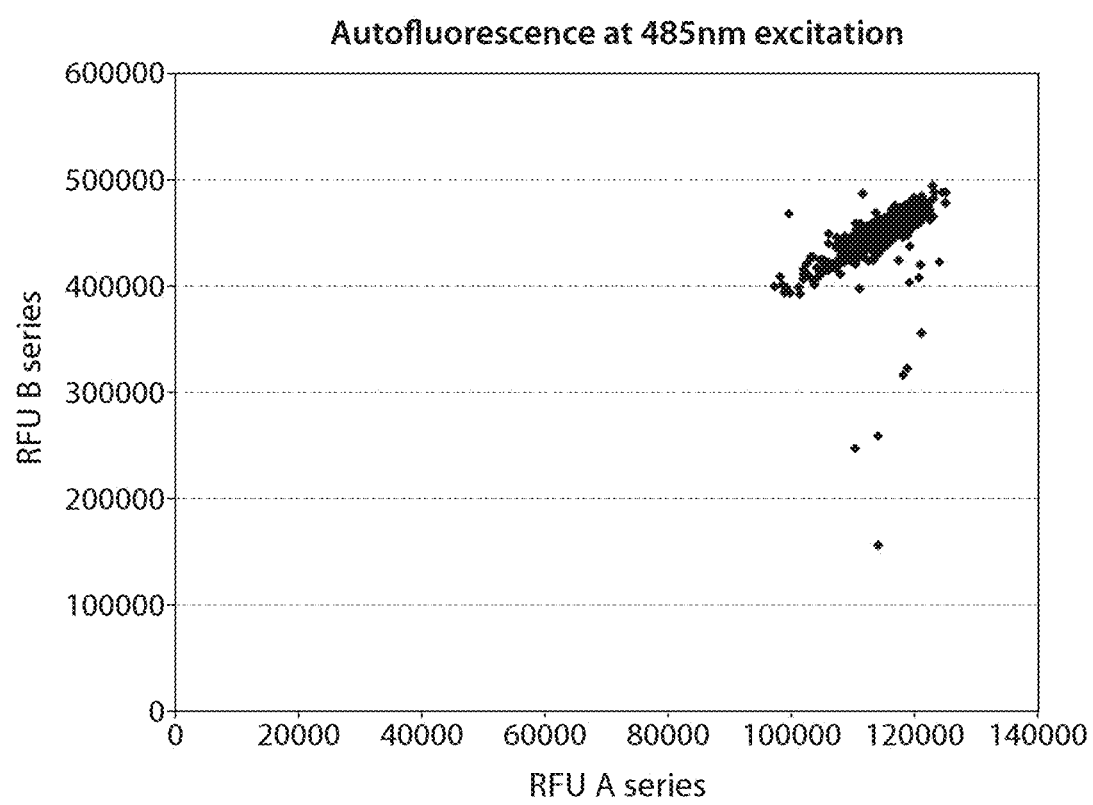
FIG. 6 shows a scatter plot of 535 emission (RFU) of polypeptide 4.9 in the presence of known bioactive small molecules. In this case, autofluorescence would lead to a reproducible increase in signal.

Compound autofluorescence with polypeptides 4.9 and 4.10 was then assessed using the same pilot experiment described above. The difference was striking (FIG. 6). Using the FITC/QXL-520 labeled polypeptides, no compound autofluorescence was observed with excitation at 485 nm. Note that since the readout is total fluorescence, in this case autofluorescence would lead to a reproducible increase in signal.

Figure 7:
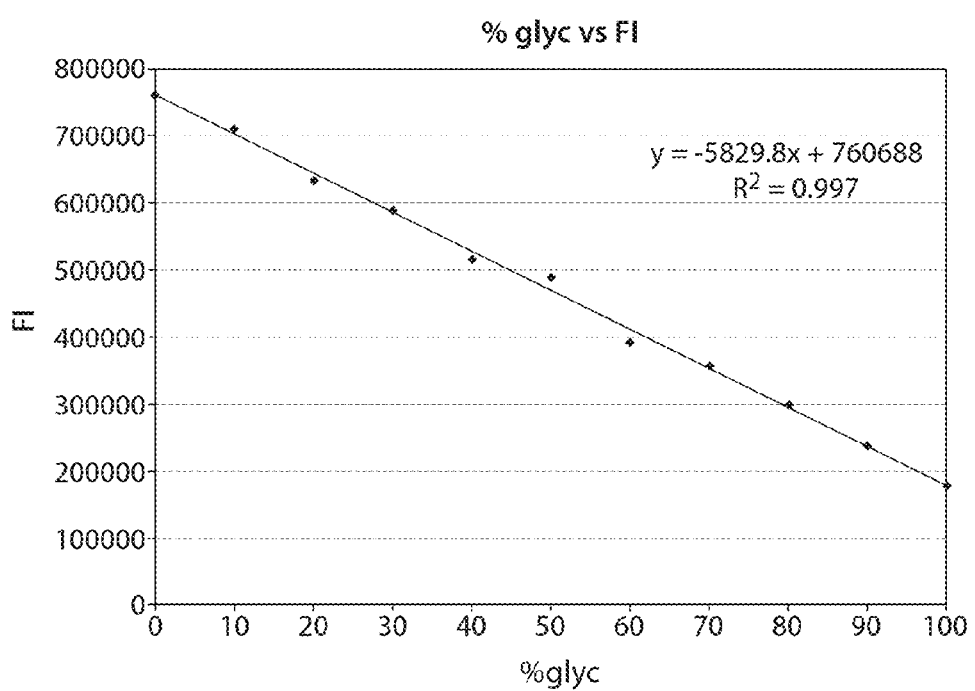
FIG. 7 is a graph showing 535 nm emission (RFU) of mixtures of glycosylated and unglycosylated polypeptide 4.9. RFU is shown on the y-axis, and percent glycopeptide is shown on the x-axis. The slope and $R^2$ values are shown.

Another advantage of the quencher approach was assay linearity over the entire glycosylation range observed with both polypeptides 4.9 and 4.10 (FIG. 7). This was not expected, and was not seen with in any polypeptides 4.6 or 4.8. Linearity allows use of this assay for lower throughput applications that require greater sensitivity, such as kinetics. It also makes a quantitative data workup possible, which was exploited after the high-throughput screen (see below).

Conversion Target for Negative Controls

In kinetic assays it is important to establish an appropriate conversion target for the negative controls (in this case, the extent of glycosylation in the absence of inhibitors) and determine the concentration of reagents (i.e. OGT and both substrates) required to achieve this level of conversion. A reasonable conversion goal is 80%, since this will result in a large assay window but still ensure that the reaction is not run past completion, potentially missing weak inhibitors. The target time window to achieve this conversion was 2-4 hours, which is sufficiently long to ensure that small variations in the timing of liquid handling steps would not significantly affect the outcome, but short enough to be practical. After significant optimization, it was found that 4 μM of polypeptide 4.10, 20 μM UDP-GlcNAc, and 50-100 nM sOGT (depending on the enzyme batch) would reproducibly give 70-80% conversion in 2-4 hours. Because of the small but inherent variability, an aliquot of assay mix for each round of high throughput screening was analyzed by LC/MS to determine the actual conversion for that run.

High Throughput Screening

With the final assay conditions established, 124,226 compounds were screened in duplicate at the ICCB (Harvard University, Boston, Mass.) over two days; the highest throughput of any assay performed at the ICCB screening facility[27]. Small molecule libraries from several commercial vendors were screened as well as known bioactive compounds, natural product extracts, and molecules made using diversity oriented synthetic approaches[28]. Included in this set were 52,026 of the 64,416 compounds screened using a donor displacement method such as that described in PCT application PCT/US2007/008806, which was filed Apr. 11, 2007. The vast majority compounds screened were small molecules (average MW ~350) that were optimized to have favorable physico-chemical properties such as solubility, decreased toxicity, and increased stability[29]. All of the commercial compounds at the ICCB are plated at a stock concentration of 5 mg/mL, which, given a 20 μL reaction volume, corresponds to a 25 μg/mL inhibitor concentration in

TABLE 4

DEAC modified polypeptide derivatives of CK2.
Mutated residues are shown in italics and the
glycolsylated serine is bold.

| peptide | Mutation | Sequence |
|---------|----------|----------|
| 4.9 | S → R | FITC(Aha)STPVS*R*ANMK(QXL ™ 520) (SEQ ID NO: 15) |
| 4.10 | S → R | FITC(Aha)STPVS*R*ANMK(QXL ™ 520)R K(QXL ™ 520) (SEQ ID NO: 16) | each well. The format of most compound plates at the ICCB has the last two columns of each 384-well plate empty. This allowed each assay plate to have column of negative controls (run without inhibitor) and column of positive controls (run without sOGT), which allowed a Z' to be calculated for each plate. These values typically ranged from 0.7-0.8.

Data workup began by calculating the average positive and negative control values independently for both duplicates of each plate. Using the linear relationship between percent glycosylation and fluorescence shown above (FIG. 7), the percent glycosylation was calculated for each well, with 0% corresponding to the average value of the positive controls and 100% corresponding to the average value of the negative controls. In actuality the range is roughly 0%480% glycosylated polypeptide since the reaction was not allowed to proceed to completion. However, this simplification was employed to facilitate the comparison of different sets of plates. There were remarkably few compounds that reproducibly appeared to inhibit OGT, which enabled hits to be selected using a very high cutoff. Compounds with <70% activity in one duplicate and <80% activity in the second duplicate were scored as hits. Even using this lax criterion, the total unfiltered hit set only numbered 84, corresponding to a hit rate of 0.065%.

Hit Validation for Both Assays

Figure 8:
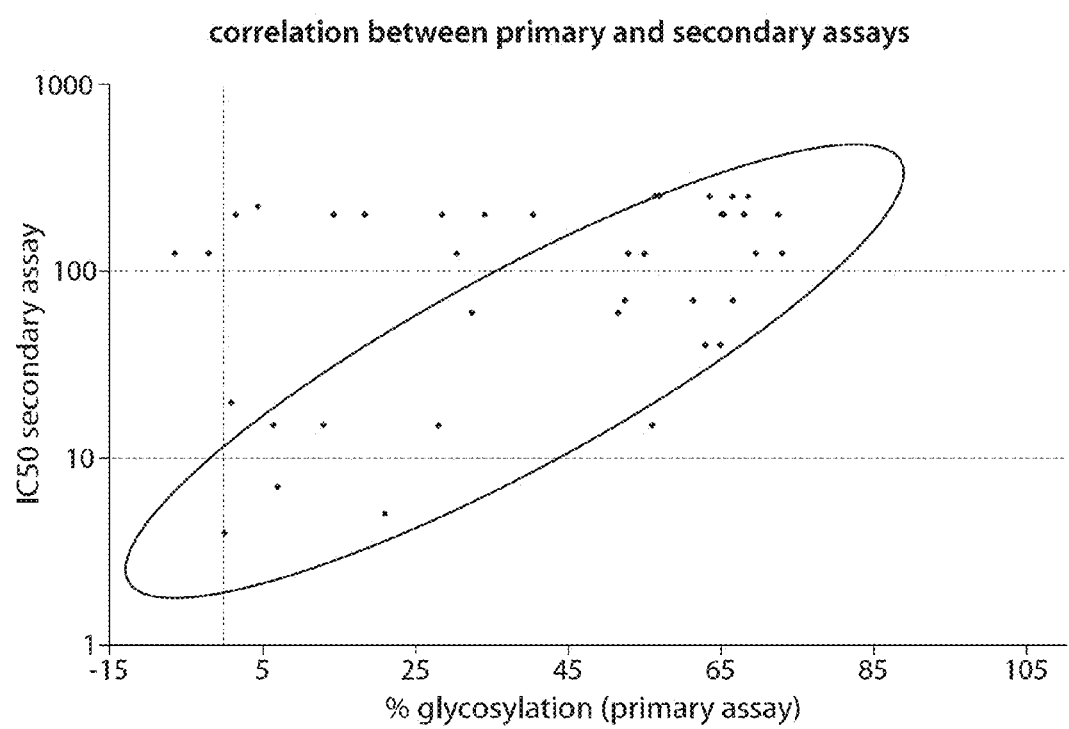
FIG. 8 shows a graph demonstrating the correlation between hit potencies in the primary and secondary assay. Although some strong hits inhibit weakly in the secondary assay, in general the stronger the primary hit, the more potent the inhibitor.

To validate the hits from the high throughput screen, a radiometric secondary assay was used (adapted from that described in described in PCT Application PCT/US2007/008806, which was filed Apr. 11, 2007). All 84 compounds were "cherry picked" and eight point $IC_{50}$ curves (with inhibitor concentration ranging from 125 μM to 970 nM) were generated. The CK23K polypeptide concentration was set at 250 μM, which is roughly 1.1× the $K_m$ value. The logic behind this was to mimic as much as possible the sub-$K_n$, FRET-peptide concentration present in the primary assay, so that polypeptide competitive inhibitors would not be swamped out by the higher CK23K concentrations used to screen the donor displacement assay. In addition, the buffer used in high throughput screening, which had no NaCl and contains detergents, was used in secondary screening. Of the 84 compounds assayed, 38 (45%) showed detectable inhibition at 125 μM, and 9 compounds (11%) had $IC_{50}$ values≤20 μM. A relationship existed between hit potency in the primary and secondary assay (FIG. 8), though there seemed to be a group of structurally unrelated weak validated inhibitors ($IC_{50}$ 125-250 μM) that inhibited strongly in the primary assay.

The low primary hit rate and high hit validation percentage indicated that the assay had a remarkably low false positive rate, especially considering that the raw hits were not filtered. In particular, two types of false positives, promiscuous inhibitors and fluorescent compounds, were almost entirely absent in this hit set. Given the large overlap of compounds between the two screens (52,026 compounds), it is a certainty that both types of compounds are present in the libraries screened, but were engineered out of the hit set during assay design. Although not all of the validated hits had been analyzed for promiscuous inhibitory behavior, it was not likely that a sizable number of these compounds inhibited non-specifically. First, the structures of the hits (see below) had few features of promiscuous inhibitors[30, 31]. Shoichet and co-workers have recently proposed methods of greatly reducing promiscuous hit in high throughput screening, the most important of which is the use of detergent in the assay buffer[30, 32]. These data obtained in these experiments corroborated that finding. Another important consideration is that any promiscuous inhibitor would likely inhibit the protease (which is present at 1/100,000 the concentration of OGT). Protease inhibition mimics polypeptide glycosylation and thus a negative well.

Figure 9:
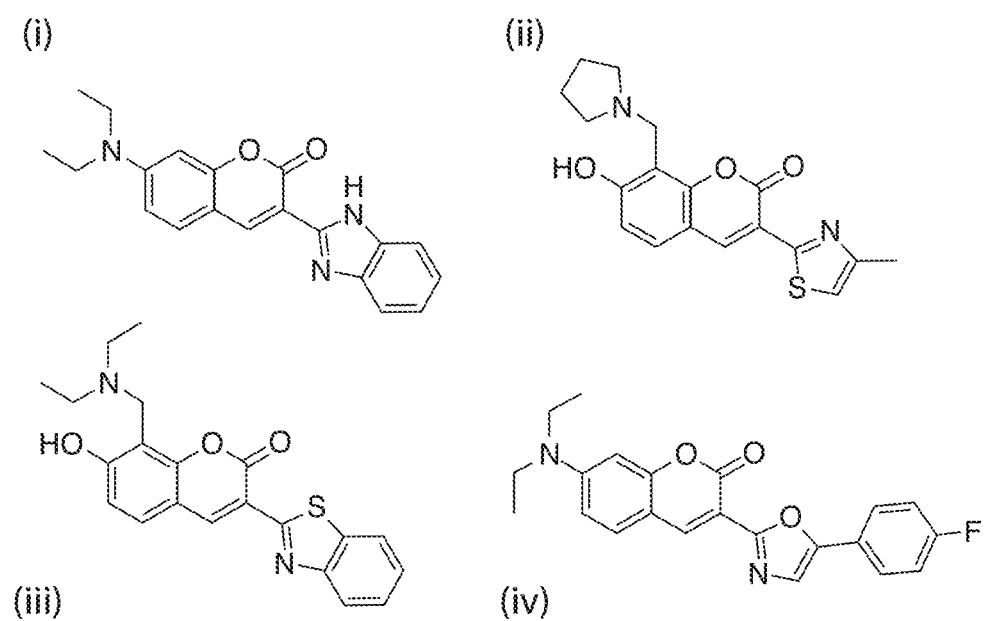
FIG. 9 shows representative fluorescent compounds (identified here as compounds i, ii, iii, and iv) found in the primary hit set.

Fluorescent compounds were found in the hit set, but at a very low frequency (11 fluorescent compounds; 13% of total hits). As expected, none of these compounds showed inhibitory activity in the secondary assay. Because both assays used a fluorescein-labeled probe molecule, the difference in the frequency of fluorescence interference was due solely to the dye concentration, which is 50 nM in the donor displacement high-throughput screen and 4 μM in the kinetic assay. Supporting this fact is that the structures of most of the 11 false positives have a similar, coumarin-2-thiazole/oxazole/imidazole structure (FIG. 9), which is known to be highly fluorescent.

Figure 10:
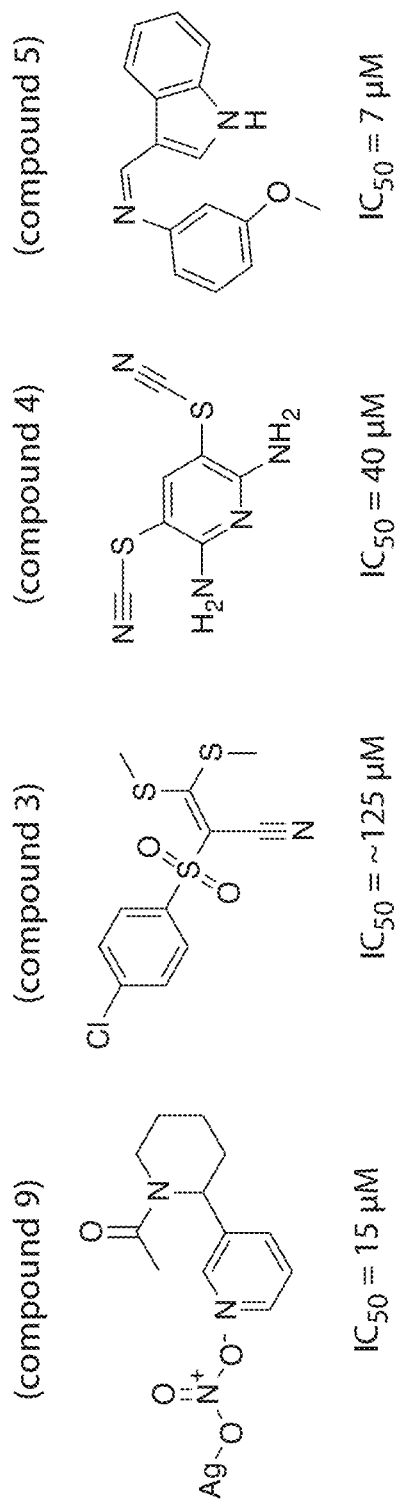
FIG. 10 shows compounds, identified here as compounds 9, 3, 4, and 5, which were hits with reactive or potentially reactive functional groups. Schiff base hydrolysis unmasks an aldehyde (far right, compound 5).
Figure 11:
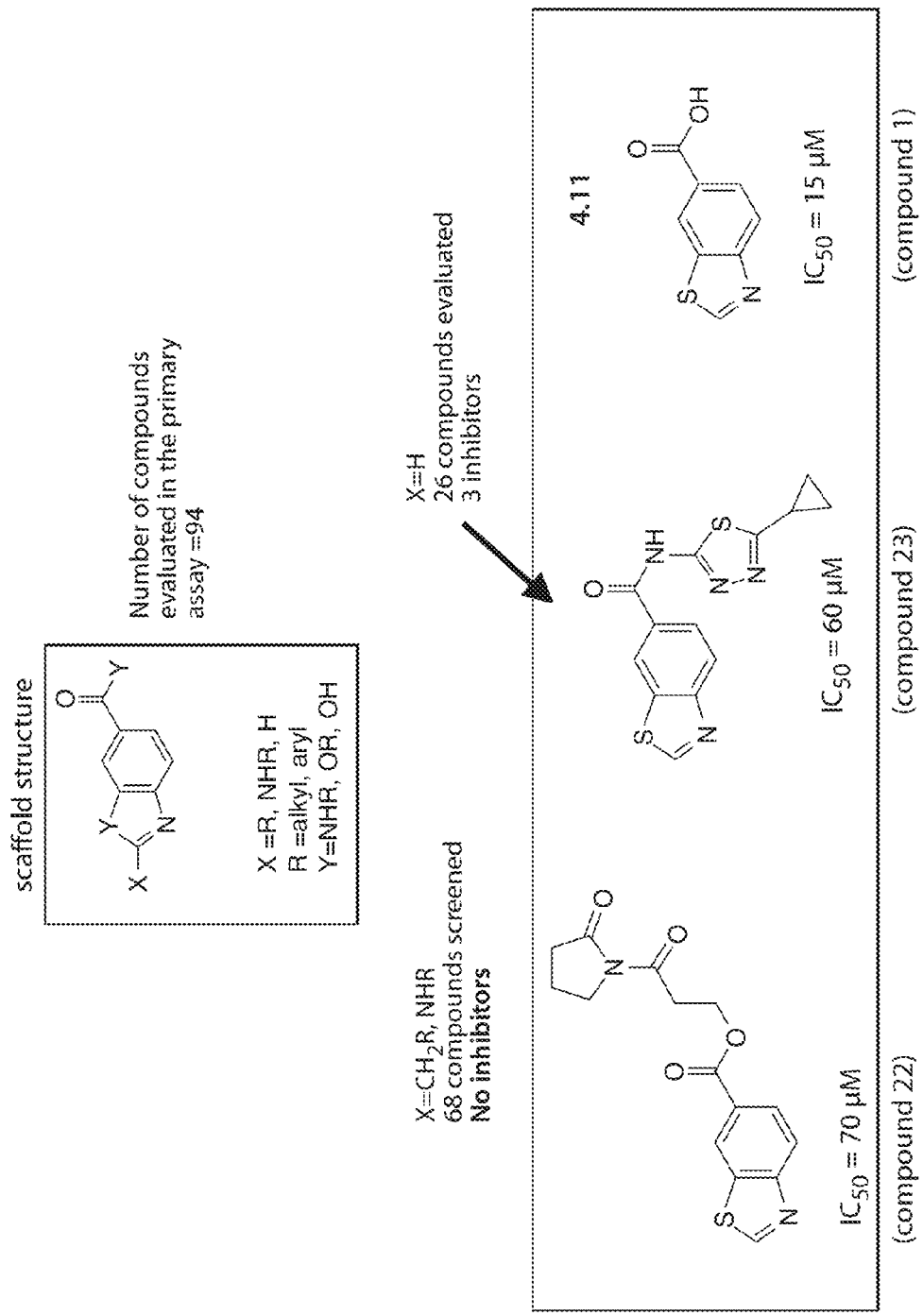
FIG. 11 shows benzothiazole-6-carboxylic scaffold (at top) and compounds 22, 23 and 1.
Figure 12:
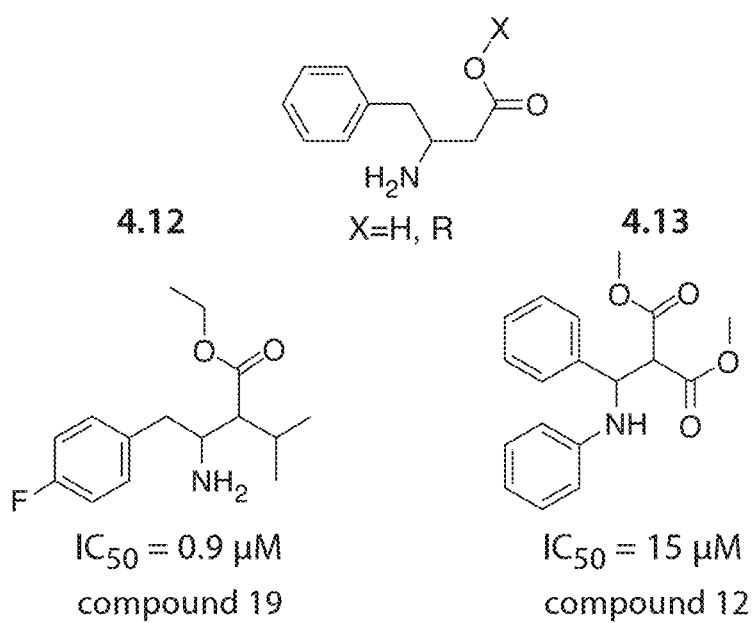
FIG. 12 shows 3-amino-4-phenylbutanoic acid scaffold (at top) and compounds 19 and 12.

Of the 38 confirmed inhibitors, 23 (60%; 27% of the total hits) had $IC_{50}$ values 5125 μM. Of these 23 compounds, four compounds contained reactive or potentially reactive groups (FIG. 10). Five of the remaining 19 hits clustered into two classes with shared structural elements. The first of these are compounds that contain a benzothiazole-6-carboxylic acid scaffold (FIG. 11). 94 compounds containing this core were assayed in the primary screen. Insufficient data exists to comment on SAR trends for the Y position, but of the three inhibitors, the free carboxylic acid compound 4.11 (and smallest compound) is the most potent. It is notable that no substitution was tolerated at the X position, even $NH_2$ and $CH_3$ with Y=OH. The second clustering of compounds contains a core with a β-amino acid. Although this grouping contains only two members, it is notable for several reasons. First, both compounds, 4.12 and 4.13 (FIG. 12), have similar sterics at the α-amino position, and could potentially mimic the valine that was determined to be critical for OGT catalysis previous work[25]. Second, there are only six compounds with this conserved 3-amino-4-phenylbutanoic acid scaffold (shown at top of FIG. 12) in the screened libraries, and only two of these six, 4.12 and 4.13, have branched groups at the α-amino position. Third, 4.12 is the most potent OGT inhibitor discovered to date, with an $IC_{50}$=900 nM. Finally, 4.13 is the only inhibitor discovered in this assay that was a hit in the primary donor analog displacement assay (see PCT Application PCT/US2007/008806, which was filed Apr. 11, 2007). This compound did not inhibit when screened in the secondary assay, perhaps because of the higher polypeptide concentration used.

Figure 13:
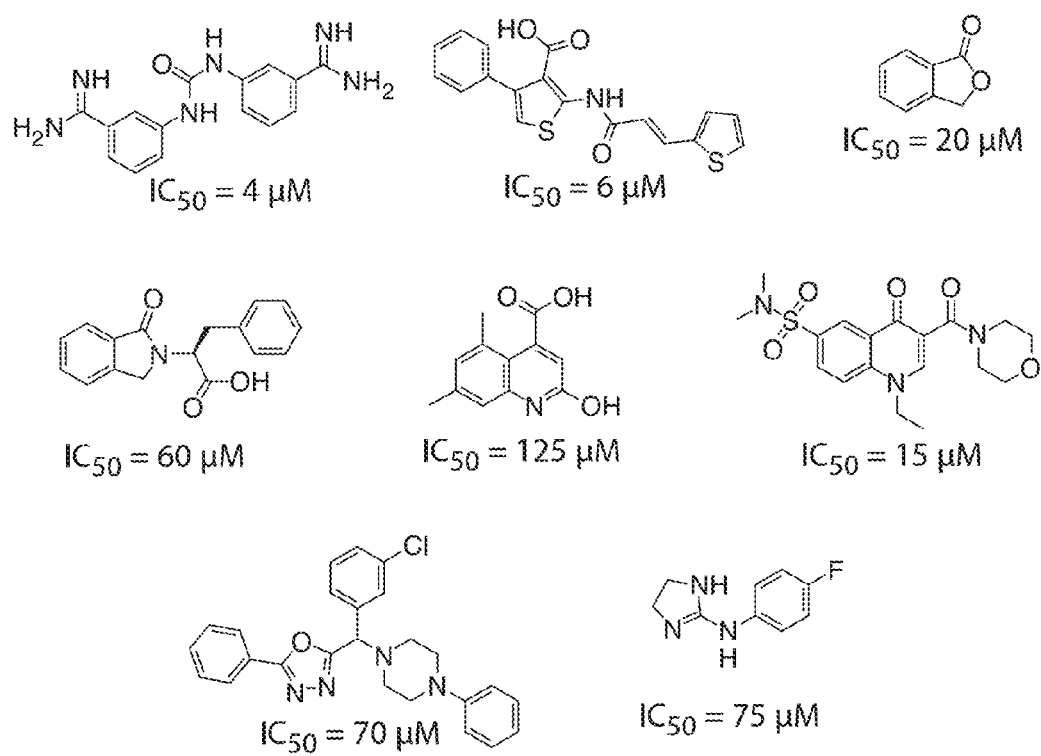
FIG. 13 shows compounds that were singleton hits with the assay. Top row, left to right, shows compounds 10, 2 and 16. Middle row, left to right shows compounds 17, 6, and 18. Bottom row, left to right, shows compounds 15 and 21.

The remainder of the identified inhibitors appeared to have no conserved structural features, however it should be noted that many of these hits contained a free carboxylic acid (FIG. 13). Most of these compounds were unique in the screened libraries, with few and often no strongly related compounds.

Discussion

Although most of the compounds did not cluster, two structural scaffolds could be identified. Almost all of the hits, singletons and clusters, were poorly represented in the ICCB commercial libraries and few analogs were commercially available. The syntheses of small chemical libraries are being explored to obtain SAR data around several of the compounds.

Another motivation guiding assay development was to add compounds that inhibit through other binding modes to the set of available tools since UDP-GlcNAc competitive inhibition might affect normal O-GlcNAc processes (which occurs at low HSP flux and UDP-GlcNAc levels) before pathological ones (occurs with increased flux)[33].

The assay described herein is the first kinetic assay that is readily adaptable to high-throughput screening. A similar approach is used to screen other glycosyltransferases that utilize polypeptide acceptor substrates, such as the enzymes involved in mucin biosynthesis and notch signaling.

Assay Development and Validation

Screening Protocol 384-well plates (Costar #3710) were filled using a liquid handling robot with 10 µL of a mixture of 8 µM polypeptide 4.10, 40 µM UDP-GlcNAc, and buffer (50 mM Tris, 20 mM CaCl$_2$, 0.05% Tween-20, 0.05% NP-40, pH=7.8, 500 µM tris(hydroxypropyl)phosphine). Compound libraries were then transferred to the assay plates using a 100 nL pin array and 10 µL of 500 nM sOGT in buffer (50 mM Tris, 20 mM CaCl$_2$, 0.05% Tween-20, 0.05% NP-40, pH=7.8, 500 µM tris(hydroxypropyl)phosphine) was added using a liquid handling robot. The compounds were assayed at a concentration of 25 µg/mL or ~70 µM, assuming an average compound MW of 350. After 2-3 hours, 20 µL of a 20 ng/mL proteinase K solution in buffer (50 mM Tris, 20 mM CaCl$_2$, 0.05% Tween-20, 0.05% NP-40, pH=7.8) was added and allowed to react for 30-90 minutes. The plates were read using a Perkin-Elmer Envision® microplate reader with a 480 nm excitation filter and 530 nm emission filter.

Hit Validation Protocols

Hits were examined using the secondary assay as described in PCT Application PCT/US2007/008806, which was filed Apr. 11, 2007, with minor modifications. One microliter aliquots (5 mg/mL) of the hits were obtained from the ICCB, and these were normalized to 5.0 mM with DMSO. These compounds were screened at 8 two-fold dilutions ranging from 125 µM to 900 nM. The reaction mixture containing 250 µM polypeptide, 6.25 µM UDP-$^{14}$C-GlcNAc, ~20-40 nM sOGT, and buffer (50 mM Tris, 20 mM CaCl$_2$, 0.05% Tween-20, 0.05% NP-40, pH=7.8, 500 µM tris(hydroxypropyl)phosphine). Reactions were run for 20-30 minutes, then spotted on Whatman P81 phosphocellulose discs, washed three times for five minutes in 1% phosphoric acid, and counted by liquid scintillation counting. The IC$_{50}$ curve was fit to the following equation using Prism 4 software (GraphPad Software, Inc., San Diego, Calif.).

$$Y=Y\min+(Y\max-Y\min)/(1+10^{\wedge}((\log(X)-\log(IC50))*h))$$

where: X is the inhibitor concentration, Y is the reaction rate, and h is the hill slope.

Example 2

An Additional Glycosylation Screening Assay

The sequelae associated with *Clostridium difficile* infection is caused mainly by the endocytosis of the bacterially produced toxins, ToxA (Genbank Accession No. P16154) and ToxB (Genbank Accession No. P18177). After these proteins are endocytosed into intestinal epithelium, the toxin glycosylates many small GTPases at a known threonine residue. Polypeptides models on one of these GTPases, Rac 1 were synthesized. Rac 1 has Genbank Accession No. P63000.

```
polypeptide 1   FITC-EYIPTVFDNK          (SEQ ID NO: 17)
                native sequence polypeptide 2   FITC-EYRPTVFDNK I-->R    (SEQ ID NO: 18)

polypeptide 3   FITC-EYIPTVDDNK F-->D    (SEQ ID NO: 19)
```

The glycosylated residues are bolded.

Each of these polypeptides is screened against thermolysin, Proteinase K, and prolylendopeptidase (PEP). Thermolysin preferentially cleaves sites with bulky and aromatic residues (Be, Leu, Val, Ala, Met, Phe) in position P1'. Cleavage is favored with aromatic sites in position P1 but hindered with acidic residues in position P 1. Pro blocks when located in position P2' but not when found in position P1. Therefore polypeptides 1 and 3 are thermolysin candidates.

Proline-endopeptidase preferentially cleaves at Pro in position P1. Proline-endopeptidase may also accept Ala in position P1. With Pro in position P1 the activity is blocked when another Pro is at position P1'. All polypeptides are candidates with cleavage with PEP, but polypeptide 2 satisfies multiple criteria.

Proteinase K typically cleaves after hydrophobic amino acids, but its substrate specificity is somewhat ambiguous. All polypeptides are candidates for Proteinase K. For expanded proteolysis rules, see: Keil, B. Specificity of proteolysis. Springer-Verlag Berlin-Heidelberg-New York, pp. 335. (1992).

Example 3

De-Glycosylation Assay

A glycosidase enzyme is contacted (under conditions suitable for activity of the glycosidase enzyme) with a molecule comprising a detectably labeled polypeptide substrate having (i) a glycosylated O-glycosylation site and (ii) a specific protease cleavage site positioned in the polypeptide such that the rate of cleavage of the polypeptide by the specific protease at the specific protease cleavage site is different when the polypeptide is O-glycosylated at the glycosylation site than when the polypeptide is not O-glycosylated at the glycosylation site. The detectable label is positioned in the polypeptide such that a change in the detectable label identifies cleavage of the polypeptide by the specific protease. The specific protease that cleaves and the specific protease site in the polypeptide is added to the contacted polypeptide. The mixture is incubated under conditions suitable for activity of the specific protease. Cleavage of the polypeptide by the specific protease is monitored and the rate of cleavage is characteristic of the level of de-glycosylation of the glycosylation site.

The assay is also run in a manner that includes contact of the glycosidase enzyme and the molecule that includes the detectably labeled polypeptide substrate with a candidate compound. A reduction in cleavage by the protease in a sample that includes a candidate compound indicates that the compound inhibits the de-glycosylation (e.g. inhibits activity of the glyscosidase).

Example 4

Polypeptide N-acetylgalactosaminyltranferases (ppGalNAcTs) assays

Figure 14:
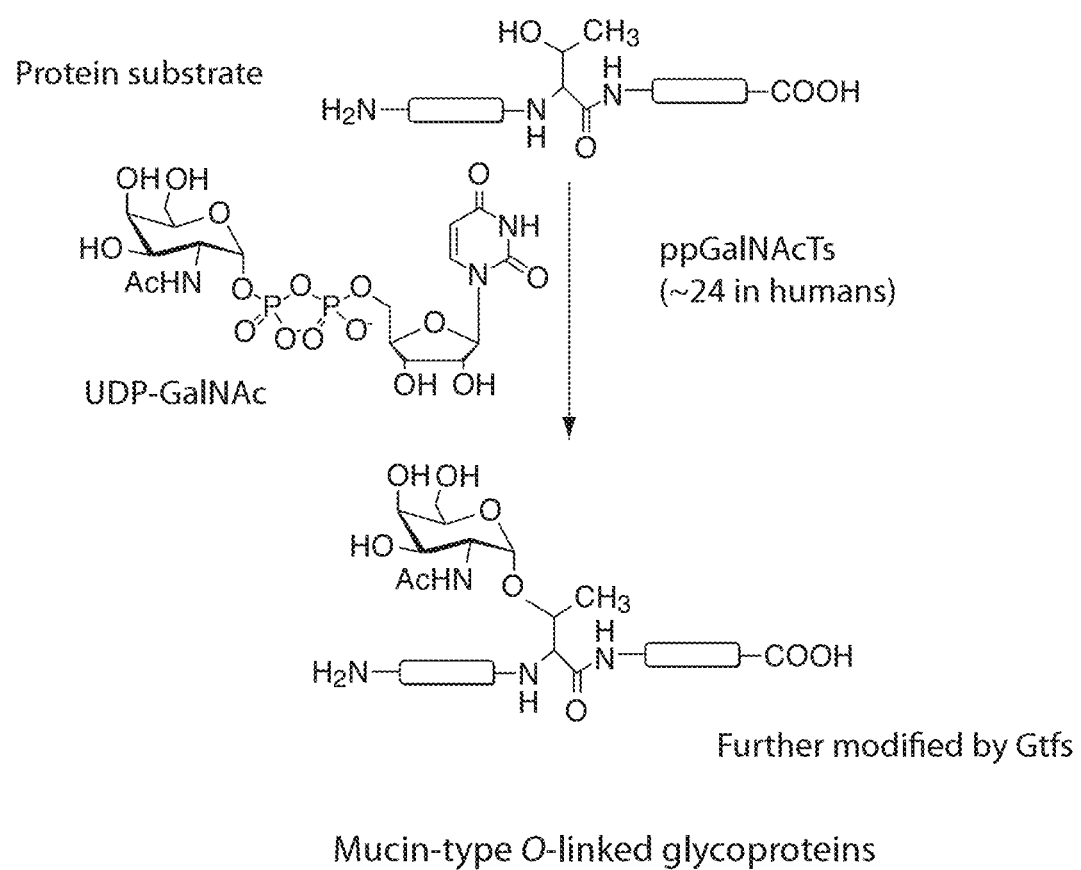
FIG. 14 shows the biochemical activity of ppGalNAcTs
Figure 15A:
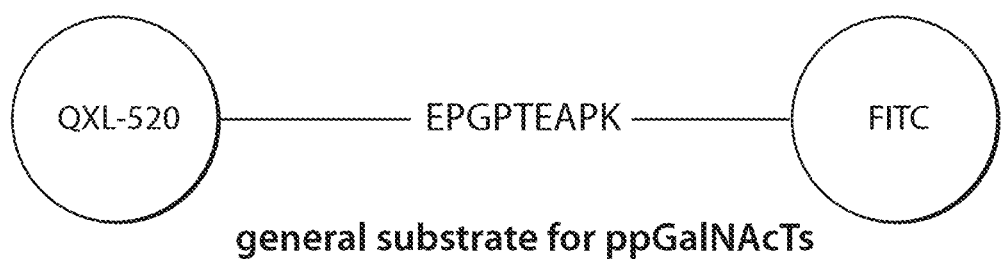
FIG. 15 shows the general substrate for ppGalNAcT (EPGPTEAPK SEQ ID NO: 25) in FIG. 15A and in FIG. 15B shows the selective substrate for ppGal NAcT1 (EDAVTPGPK SEQ ID NO:26).
Figure 15B:
Figure 16:
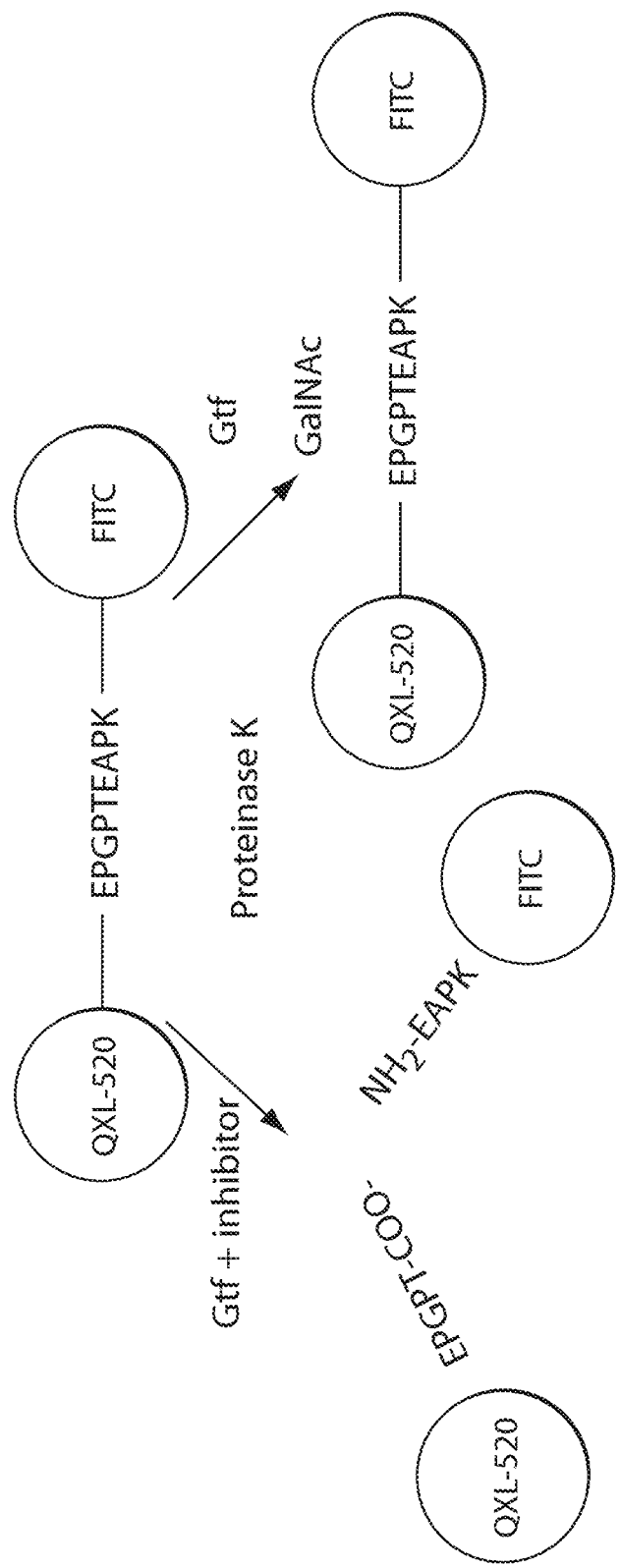
FIG. 16 shows the protease protection assay for ppGalNacT1: Substrate peptide EPGPTEAPK (SEQ ID NO: 25); Cleaved substrate peptides EPGPT (SEQ ID NO: 27) and EAPK (SEQ ID NO: 28).
Figure 17A:
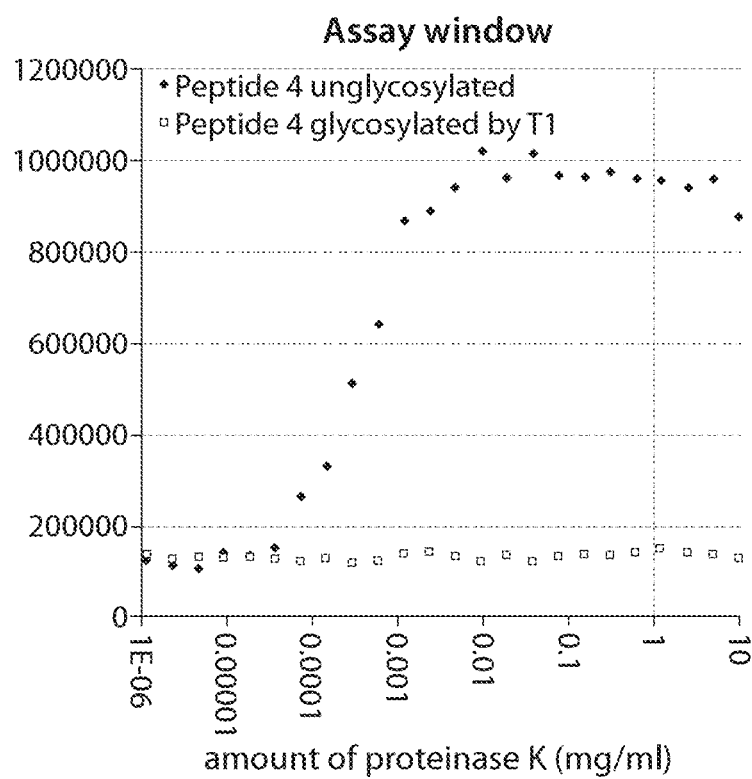
FIG. 17A shows the assay window and FIG. 17B shows the assay linearity graph.
Figure 17B:
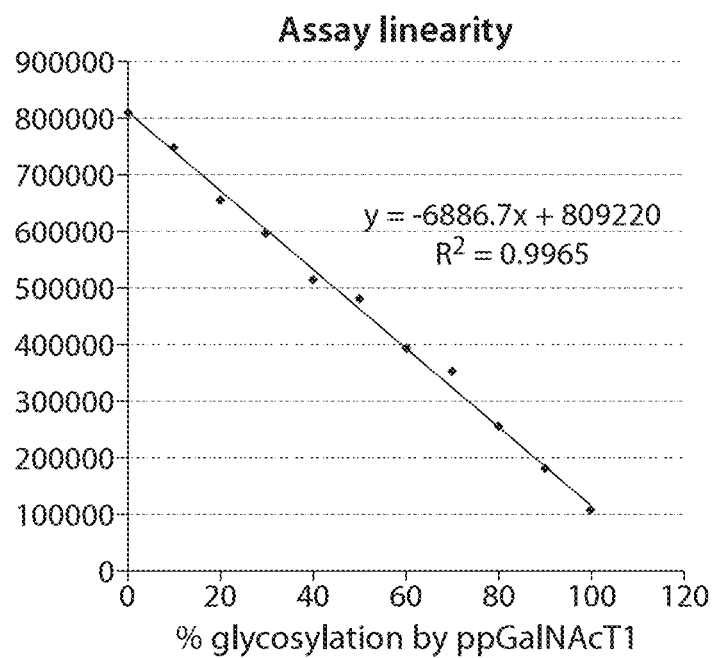

There are multiple isoforms of the enzyme polypeptide N-acetylgalactosaminyltranferases (ppGalNAcTs). Activity of ppGalNAcTs are illustrated in FIG. 14. Using assay methods as described above, peptide substrates for ppGalNAcTs were prepared and used to assay to identify modulators of ppGalNAcTs activity. Peptide substrates EPGPTEAPK (SEQ ID NO:25) and EDAVTPGPK (SEQ ID NO:26) were prepared (see FIG. 15) and utilized to assay for modulators of the enzymes. Each peptide substrate include a proteinase K cleavage site. The identified compound SEQ ID NO:25 is a general substrate for ppGalNAcTs and identified compound SEQ ID NO:26 is a selective substrate for the enzyme ppGalNAcT1. Assays were run and alterations in the rate and/or amount of cleavage by proteinase K was determined. The cleavage products illustrated in FIG. 16 show that GTF+ inhibitor resulted in cleavage by proteinase K. Little or no cleavage was observed without the presence of a ppGalNacT inhibitor. A graphic representation of the assay of cleavage of the peptide substrate under conditions with or without glycosylation of the substrate is presented in FIGS. 17A and B which show that cleavage of unglycosylated substrate greatly exceeds that of glycosylated substrate. The difference in cleavage permitted use of the assay to identify compounds that inhibit glycosylation of the substrate by ppGalNAcTs. Additional inhibitory compounds identified using the assay include Compound 24 and Compound 27 (see Table 1).

Using the assay, compounds that inhibit ppGalNAcTs were identified. Identified compounds included compounds 24-27 (see Table 1).

Figure 18A:
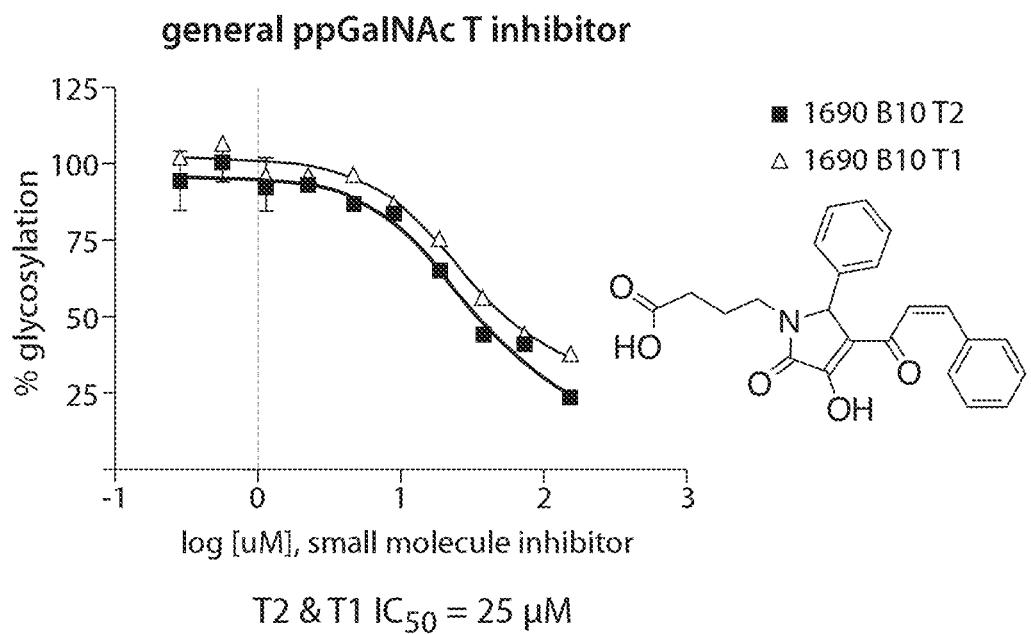
FIG. 18 shows in FIG. 18A the % of glycosylation in the presence of compound 24 showing that compound 24 is a general ppGalNAcT inhibitor and inhibits both the T2 and T1 ppGalNAcT.
FIG. 18B shows the % glycosylation in the presence of compound 25, which is more selectively inhibits ppGalNAcT2 than ppGalNAcT1.
Figure 18B:
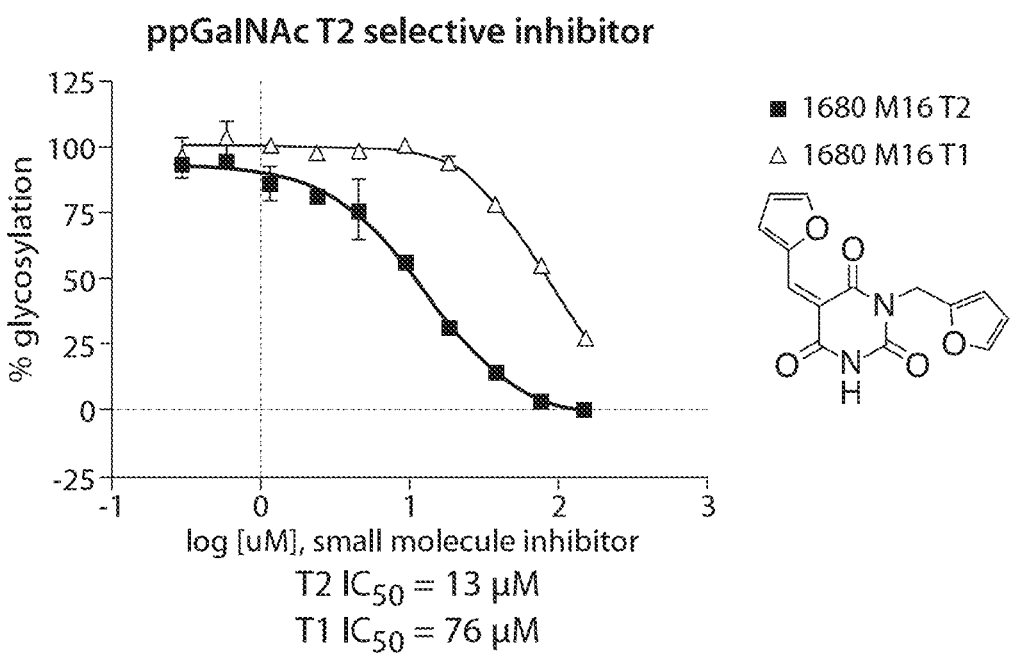
Figure 19:
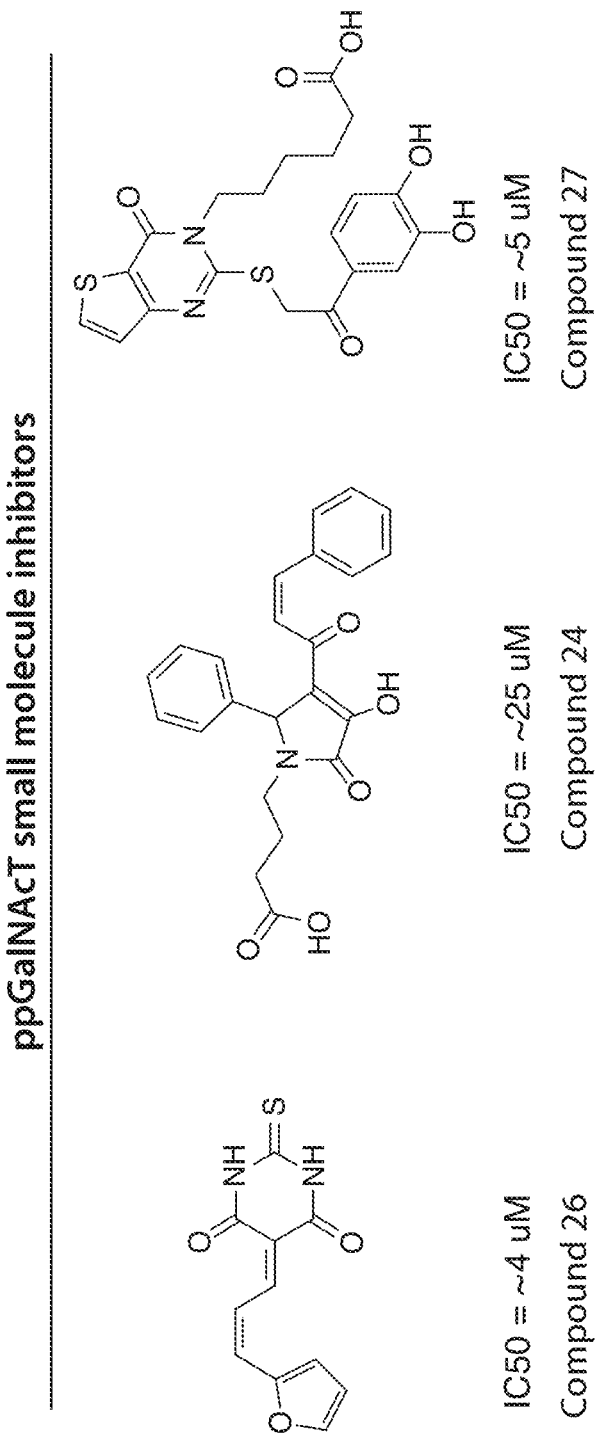
FIG. 19 shows selected ppGalNACT small molecule inhibitors (left to right: Compound 26, compound 24, and compound 27)
Figure 20A:
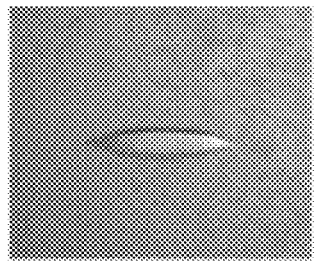
FIG. 20 shows the results of growing ppGALNAcT2 crystals in the absence of an inhibitor (FIG. 20A) and in the presence of an inhibitor FIG. 20B.
Figure 20B:
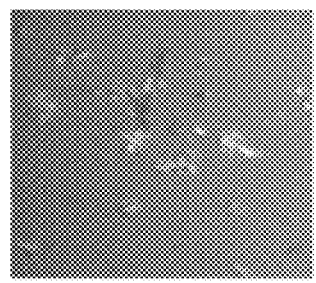

It was determined that the assay could also be used to identify isoform selective inhibitors. For example, FIG. 18A shows results from a general ppGalNAcT inhibitor (compound 24), which inhibited both ppGalNAcT1 and ppGalNAcT2. FIG. 18 B shows results from compound 25, which was a more selective inhibitor for ppGalNAcT2 than for ppGalNAcT1. Additional small molecule inhibitors of ppGalNAcT are shown in FIG. 19. FIG. 20 shows the effect of an identified small molecule inhibitor on crystal growth of ppGalNAcT2. The presence of the inhibitor disrupted crystal growth of the ppGalNAcT2.

The assays results demonstrate an additional kinetic assay that can be used to identify inhibitors of O-linked glycosylation. The results indicated that the O-linked glycosylation assays of the invention are useful for identifying modulators of O-linked glycosylation that is carried out by multiple different O-linked glycosylating enzymes and that the assays could be used to identify isoform-specific glycosyltranferase (Gts) inhibitors. Thus, the screens could be used to assay Gtfs from different Gts classes.

REFERENCES FOR EXAMPLES SECTION

1. Gross, B J., B. C. Kraybill, and S: Walker, *Discovery of O-GlcNAc transferase inhibitors.* J Am Chem Soc, 2005. 127(42): p. 14588-9.
2. Hu, Y., et al., *Identification of selective inhibitors for the glycosyltransferase MurG via high-throughput screening.* Chem Biol, 2004. 11(5): p. 703-11.
3. Ten Hagen, K. G., T. A. Fritz, and L. A. Tabak, *All in the family: the UDP-GalNAc:polypeptide N-acetylgalactosaminyltransferases.* Glycobiology, 2003. 13(1): p. 1R-16R.
4. Qiu, H., et al., *Expressions of polypeptide: N-acetylgalactosaminyltransferase in leukemia cell lines during 1,25-dihydroxyvitamin D3 induced differentiation.* Glycoconj J, 2006. 23(7-8): p. 575-84.
5. Topaz, O., et al., *Absence of intraepidermal glycosyltransferase ppGalNac-T3 expression in familial tumoral calcinosis.* Am J Dermatopathol, 2005. 27(3): p. 211-5.
6. Shi, S, and P. Stanley, *Protein O-fucosyltransferase 1 is an essential component of Notch signaling pathways.* Proc Natl Acad Sci USA, 2003. 100(9): p. 5234-9.
7. Comess, K. M. and M. E. Schurdak, *Affinity-based screening techniques for enhancing lead discovery.* Curr Opin Drug Discov Devel, 2004. 7(4): p. 411-6.
8. Donovan, R. S., et al., *A solid-phase glycosyltransferase assay for high-throughput screening in drug discovery research.* Glycoconj J, 1999. 16(10): p. 607-15.
9. Palcic, M. M. and K. Sujino, *Assays for glycosyltransferases.* TRENDS IN GLYCOSCIENCE AND GLYCOTECHNOLOGY, 2001. 13(72): p. 361-370.
10. Khraltsova, L. S., et al., *An enzyme-linked lectin assay for alpha1,3-galactosyltransferase.* Anal Biochem, 2000. 280 (2): p. 250-7.
11. Hang, H. C., et al., *Small molecule inhibitors of mucin-type O-linked glycosylation from a uridine-based library.* Chem Biol, 2004. 11(3): p. 337-45.
12. Ogawa, H. and U. Galili, *Profiling terminal N-acetyllactosamines of glycans on mammalian cells by an immunoenzymatic assay.* Glycoconj J, 2006. 23(9): p. 663-74.
13. Gosselin, S., et al., *A continuous spectrophotometric assay for glycosyltransferases.* Anal Biochem, 1994. 220 (1): p. 92-7.
14. Huang, Y. H., D. H. Picha, and A. W. Kilili, *A continuous method for enzymatic assay of sucrose synthase in the synthetic direction.* J Agric Food Chem, 1999. 47(7): p. 2746-50.
15. Lowery, R. G. and K. Kleman-Leyer, *Transcreener: screening enzymes involved in covalent regulation.* Expert Opin Ther Targets, 2006. 10(1): p. 179-90.
16. Wongkongkatep, J., et al., *Label-free, real-time glycosyltransferase assay based on a fluorescent artificial chemosensor.* Angew Chem Int Ed Engl, 2006. 45(4): p. 665-8.
17. Beasley, J. R., et al., *Miniaturized, ultra-high throughput screening of tyrosine kinases using homogeneous, competitive fluorescence immunoassays.* Assay Drug Dev Technol, 2004. 2(2): p. 141-51.
18. Wesche, H., S. H. Xiao, and S. W. Young, *High throughput screening for protein kinase inhibitors.* Comb Chem High Throughput Screen, 2005. 8(2): p. 181-95.
19. von Ahsen, O. and U. Bomer, *High-throughput screening for kinase inhibitors.* Chembiochem, 2005. 6(3): p. 481-90.
20. Koresawa, M. and T. Okabe, *High-throughput screening with quantitation of ATP consumption: a universal non-radioisotope, homogeneous assay for protein kinase.* Assay Drug Dev Technol, 2004. 2(2): p. 153-60.
21. Rodems, S. M., et al., *A FRET-based assay platform for ultra-high density drug screening of protein kinases and phosphatases.* Assay Drug Dev Technol, 2002. 1(1 Pt 1): p. 9-19.
22. Nishikata, M., et al., *A phosphotyrosine-containing quenched fluorogenic peptide as a novel substrate for protein tyrosine phosphatases.* Biochem J, 1999. 343 Pt 2: p. 385-91.
23. Nishikata, M., et al., *Continuous assay of protein tyrosine phosphatases based on fluorescence resonance energy transfer.* Biochimie, 2006. 88(7): p. 879-86.
24. Chen, Y. X., et al., *Alternative O-GlcNAcylation/O-phosphorylation of Ser16 induce different conformational disturbances to the N terminus of murine estrogen receptor beta.* Chem Biol, 2006. 13(9): p. 937-44.
25. Vosseller, K., et al., *O-linked N-acetylglucosamine proteomics of postsynaptic density preparations using lectin weak affinity chromatography and mass spectrometry.* Mol Cell Proteomics, 2006. 5(5): p. 923-34.
26. Kraybill, B, personal communication.
27. Fletcher, D, personal communication.
28. Screening libraries are available for download. Contact: david_wrobel@hms.harvard.edu,
29. Olah, M. M., C. G. Bologa, and T. I. Oprea, *Strategies for compound selection.* Curr Drug Discov Technol, 2004. 1(3): p. 211-20.

30. Feng, B. Y., et al., *High-throughput assays for promiscuous inhibitors*. Nat Chem Biol, 2005. 1(3): p. 146-8.
31. Seidler, J., et al., *Identification and prediction of promiscuous aggregating inhibitors among known drugs*. J Med Chem, 2003. 46(21): p. 4477-86.
32. Feng, B. Y. and B. K. Shoichet, *A Detergent-Based Assay for the Detection of Promiscuous Inhibitors*. Nat. Protoc, 2006. 1(2): p. 550-553.
33. Rogawski, M. A. and G. L. Wenk, *The neuropharmacological basis for the use of memantine in the treatment of Alzheimer's disease*. CNS Drug Rev, 2003. 9(3): p. 275-308.
34. Soltero-Higgin, M., et al., *Identification of inhibitors for UDP-galactopyranose mutase*. J Am Chem Soc, 2004. 126(34): p. 10532-3.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

What is claimed is:

1. An isolated molecule comprising a cleavable detectably labeled polypeptide substrate having
   a) an O-glycosylation site and
   b) a specific protease cleavage site positioned in the polypeptide such that the rate of cleavage by a specific protease at the specific protease cleavage site is different when the polypeptide is glycosylated at the O-glycosylation site than when the polypeptide is not glycosylated at the O-glycosylation site, wherein the detectable label is positioned in the polypeptide such that a change in the detectable label identifies cleavage of the polypeptide by the specific protease at the specific protease cleavage site.

2. The isolated molecule of claim 1, wherein the polypeptide O-glycosylation site is a serine or a threonine residue.

3. The isolated molecule of claim 2, wherein the serine or threonine is positioned within 1, 2, 3, or 4 amino acids of the specific protease cleavage site.

4. The isolated molecule of claim 1, wherein the specific protease cleavage site is a single site and there is only one specific protease cleavage site.

5. The isolated molecule of claim 1, wherein the specific protease cleavage site is positioned on the N-terminal side of the O-glycosylation site.

6. The isolated molecule of claim 1, wherein the specific protease cleavage site is positioned on the C-terminal side of the O-glycosylation site.

7. The isolated molecule of claim 1, wherein the detectable label comprises a fluorescent, enzyme, radioactive, metallic, biotin, chemiluminescent, or bioluminescent molecule.

8. The isolated molecule of claim 1, wherein the detectable label is a fluorescent moiety.

9. The isolated molecule of claim 8, wherein the change in the detectable label comprises a change in fluorescence of the fluorescent moiety.

10. The isolated molecule of claim 1, wherein the detectable label is a FRET donor and a FRET acceptor pair.

11. The isolated molecule of claim 10, wherein the FRET donor and acceptor pair is 7-diethylaminocoumarin-3-carboxylic acid (DEAC) and fluorescein isothiocyanate; [2-(1-sulfonyl-5-naphthyl)-aminoethylamide] EDANS and 4,4-dimethylazobenzene-4'carbonyl (DABCYL); fluorescein isothiocyanate and tetramethylrhodamine (TMR); or Tryptophan or tyrosine and dinitrophenyl moieties.

12. The isolated molecule of claim 8, wherein the fluorescent moiety is a Cy5.5 emitter or FITC, Texas red, tetramethylrhodamine (TMR), AlexaFluor dyes, HiLyte Fluorophores, or [2-(1-sulfonyl-5-naphthyl)-aminoethylamide] EDANS.

13. The isolated molecule of claim 1, wherein the polypeptide further comprises a quenching moiety.

14. The isolated molecule of claim 13, wherein the quenching moiety is QXL-520, BHQ3, Iowa black, 4,4-dimethylazobenzene-4'carbonyl (DABCYL), BHQ1, BHQ10, QXL-570, QXL-620, dinitrophenyl (DNP) containing groups, or QSY-7,9-21, or 35.

15. The isolated molecule of claim 1, wherein the polypeptide comprises an amino acid sequence selected from the group consisting of: STPVSSANMK (SEQ ID NO:1), STPVSFANMK (SEQ ID NO:2), STPVSRANMK (SEQ ID NO:3), EYIPTVFDNK (SEQ ID NO:4), EYRPTVFDNK (SEQ ID NO:5), EYIPTVDDNK (SEQ ID NO:6), EPGPTEAPK (SEQ ID NO:25), and EDAVTPGPK (SEQ ID NO:26).

16. The isolated molecule of claim 1, wherein the specific protease cleavage site is a proteinase K cleavage site, a trypsin cleavage site, a chymotrypsin cleavage site, a thermolysin cleavage site, Staphylococcal peptidase I cleavage site, Proline-endopeptidase cleavage site, Pepsin cleavage site, Glutamyl endopeptidase cleavage site, Factor Xa cleavage site, Granzyme B Lysyl endopeptidase cleavage site, Asp-N Endopeptidase cleavage site, or enterokinase cleavage site.

17. A kit for identifying an agent that modulates O-glycosylation, the kit comprising a package housing a first container containing a polypeptide of claim 1, and instructions for using the polypeptide to identify modulators of O-glycosylation.

18. The kit of claim 17, further comprising a second container containing the specific protease that cleaves at the specific protease site of the polypeptide.

19. The kit of claim 17, wherein the polypeptide comprises the amino acid sequence set forth as one of SEQ ID NOs:1-6, 25, or 26.

\* \* \* \* \*

UNITED STATES PATENT AND TRADEMARK OFFICE
CERTIFICATE OF CORRECTION

| | | |
|---|---|---|
| PATENT NO. | : 8,993,718 B2 | Page 1 of 1 |
| APPLICATION NO. | : 14/013860 | |
| DATED | : March 31, 2015 | |
| INVENTOR(S) | : Benjamin J. Gross et al. | |

It is certified that error appears in the above-identified patent and that said Letters Patent is hereby corrected as shown below:

In the Specification

In column 1, lines 16-21, please amend the "Government Support" section as shown below:

GOVERNMENT SUPPORT

This invention was made with government support under grant numbers MH076518 and AI44854 awarded by the National Institutes of Health. The government has certain rights in the invention.

Signed and Sealed this
Fifteenth Day of September, 2015

Michelle K. Lee
*Director of the United States Patent and Trademark Office*

```
                        SEQUENCE LISTING

<160> NUMBER OF SEQ ID NOS: 28

<210> SEQ ID NO 1
<211> LENGTH: 10
<212> TYPE: PRT
<213> ORGANISM: Artificial sequence
<220> FEATURE:
<223> OTHER INFORMATION: Synthetic peptide

<400> SEQUENCE: 1

Ser Thr Pro Val Ser Ser Ala Asn Met Lys
1               5                   10

<210> SEQ ID NO 2
<211> LENGTH: 10
<212> TYPE: PRT
<213> ORGANISM: Artificial sequence
<220> FEATURE:
<223> OTHER INFORMATION: Synthetic peptide

<400> SEQUENCE: 2

Ser Thr Pro Val Ser Phe Ala Asn Met Lys
1               5                   10

<210> SEQ ID NO 3
<211> LENGTH: 10
<212> TYPE: PRT
<213> ORGANISM: Artificial sequence
<220> FEATURE:
<223> OTHER INFORMATION: Synthetic peptide

<400> SEQUENCE: 3

Ser Thr Pro Val Ser Arg Ala Asn Met Lys
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic peptide

<400> SEQUENCE: 4

Glu Tyr Ile Pro Thr Val Phe Asp Asn Lys
1               5                   10

<210> SEQ ID NO 5
<211> LENGTH: 10
<212> TYPE: PRT
<213> ORGANISM: Artificial sequence
<220> FEATURE:
<223> OTHER INFORMATION: Synthetic peptide
```

```
<400> SEQUENCE: 5

Glu Tyr Arg Pro Thr Val Phe Asp Asn Lys
1               5                   10

<210> SEQ ID NO 6
<211> LENGTH: 10
<212> TYPE: PRT
<213> ORGANISM: Artificial sequence
<220> FEATURE:
<223> OTHER INFORMATION: Synthetic peptide

<400> SEQUENCE: 6

Glu Tyr Ile Pro Thr Val Asp Asp Asn Lys
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthetic peptide

<400> SEQUENCE: 7

Ser Thr Pro Val Ser Ser Ala Asn Met Lys
1               5                   10

<210> SEQ ID NO 8
<211> LENGTH: 10
<212> TYPE: PRT
<213> ORGANISM: Artificial sequence
<220> FEATURE:
<223> OTHER INFORMATION: Synthetic peptide

<400> SEQUENCE: 8

Ser Thr Pro Phe Ser Ser Ala Asn Met Lys
1               5                   10

<210> SEQ ID NO 9
<211> LENGTH: 10
<212> TYPE: PRT
<213> ORGANISM: Artificial sequence
<220> FEATURE:
<223> OTHER INFORMATION: Synthetic peptide

<400> SEQUENCE: 9

Ser Thr Pro Arg Ser Ser Ala Asn Met Lys
1               5                   10

<210> SEQ ID NO 10
<211> LENGTH: 10
<212> TYPE: PRT
<213> ORGANISM: Artificial sequence
<220> FEATURE:
<223> OTHER INFORMATION: Synthetic peptide

<400> SEQUENCE: 10

Ser Thr Pro Val Ser Phe Ala Asn Met Lys
1               5                   10

<210> SEQ ID NO 11
<211> LENGTH: 10
<212> TYPE: PRT
<213> ORGANISM: Artificial sequence
<220> FEATURE:
<223> OTHER INFORMATION: Synthetic peptide

<400> SEQUENCE: 11
```

```
Ser Thr Pro Val Ser Arg Ala Asn Met Lys
1               5                   10

<210> SEQ ID NO 12
<211> LENGTH: 10
<212> TYPE: PRT
<213> ORGANISM: Artificial sequence
<220> FEATURE:
<223> OTHER INFORMATION: Synthetic peptide

<400> SEQUENCE: 12

Ser Thr Pro Val Ser Ser Ala Asn Met Lys
1               5                   10

<210> SEQ ID NO 13
<211> LENGTH: 10
<212> TYPE: PRT
<213> ORGANISM: Artificial sequence
<220> FEATURE:
<223> OTHER INFORMATION: Synthetic peptide

<400> SEQUENCE: 13

Ser Thr Pro Val Ser Phe Ala Asn Met Lys
1               5                   10

<210> SEQ ID NO 14
<211> LENGTH: 10
<212> TYPE: PRT
<213> ORGANISM: Artificial sequence
<220> FEATURE:
<223> OTHER INFORMATION: Synthetic peptide

<400> SEQUENCE: 14

Ser Thr Pro Val Ser Arg Ala Asn Met Lys
1               5                   10

<210> SEQ ID NO 15
<211> LENGTH: 10
<212> TYPE: PRT
<213> ORGANISM: Artificial sequence
<220> FEATURE:
<223> OTHER INFORMATION: Synthetic peptide

<400> SEQUENCE: 15

Ser Thr Pro Val Ser Arg Ala Asn Met Lys
1               5                   10

<210> SEQ ID NO 16
<211> LENGTH: 12
<212> TYPE: PRT
<213> ORGANISM: Artificial sequence
<220> FEATURE:
<223> OTHER INFORMATION: Synthetic peptide

<400> SEQUENCE: 16

Ser Thr Pro Val Ser Arg Ala Asn Met Lys Arg Lys
1               5                   10

<210> SEQ ID NO 17
<211> LENGTH: 10
<212> TYPE: PRT
<213> ORGANISM: Artificial sequence
<220> FEATURE:
<223> OTHER INFORMATION: Synthetic peptide

<400> SEQUENCE: 17
```

```
Glu Tyr Ile Pro Thr Val Phe Asp Asn Lys
1               5                   10

<210> SEQ ID NO 18
<211> LENGTH: 10
<212> TYPE: PRT
<213> ORGANISM: Artificial sequence
<220> FEATURE:
<223> OTHER INFORMATION: Synthetic peptide

<400> SEQUENCE: 18

Glu Tyr Arg Pro Thr Val Phe Asp Asn Lys
1               5                   10

<210> SEQ ID NO 19
<211> LENGTH: 10
<212> TYPE: PRT
<213> ORGANISM: Artificial sequence
<220> FEATURE:
<223> OTHER INFORMATION: Synthetic peptide

<400> SEQUENCE: 19

Glu Tyr Ile Pro Thr Val Asp Asp Asn Lys
1               5                   10

<210> SEQ ID NO 20
<211> LENGTH: 13
<212> TYPE: PRT
<213> ORGANISM: Artificial sequence
<220> FEATURE:
<223> OTHER INFORMATION: Synthetic peptide

<400> SEQUENCE: 20

Pro Gly Gly Ser Thr Pro Val Ser Ser Asn Ala Met Met
1               5                   10

<210> SEQ ID NO 21
<211> LENGTH: 4
<212> TYPE: PRT
<213> ORGANISM: Artificial sequence
<220> FEATURE:
<223> OTHER INFORMATION: Synthetic peptide

<400> SEQUENCE: 21

Ser Thr Pro Val
1

<210> SEQ ID NO 22
<211> LENGTH: 6
<212> TYPE: PRT
<213> ORGANISM: Artificial sequence
<220> FEATURE:
<223> OTHER INFORMATION: Synthetic peptide

<400> SEQUENCE: 22

Ser Arg Ala Asn Met Lys
1               5

<210> SEQ ID NO 23
<211> LENGTH: 6
<212> TYPE: PRT
<213> ORGANISM: Artificial sequence
<220> FEATURE:
<223> OTHER INFORMATION: Synthetic peptide

<400> SEQUENCE: 23

Ser Thr Pro Val Ser Arg
1               5
```

```
<210> SEQ ID NO 24
<211> LENGTH: 4
<212> TYPE: PRT
<213> ORGANISM: Artificial sequence
<220> FEATURE:
<223> OTHER INFORMATION: Synthetic peptide

<400> SEQUENCE: 24

Ala Asn Met Lys
1

<210> SEQ ID NO 25
<211> LENGTH: 9
<212> TYPE: PRT
<213> ORGANISM: Artificial sequence
<220> FEATURE:
<223> OTHER INFORMATION: Synthetic peptide

<400> SEQUENCE: 25

Glu Pro Gly Pro Thr Glu Ala Pro Lys
1               5

<210> SEQ ID NO 26
<211> LENGTH: 9
<212> TYPE: PRT
<213> ORGANISM: Artificial sequence
<220> FEATURE:
<223> OTHER INFORMATION: Synthetic peptide

<400> SEQUENCE: 26

Glu Asp Ala Val Thr Pro Gly Pro Lys
1               5

<210> SEQ ID NO 27
<211> LENGTH: 5
<212> TYPE: PRT
<213> ORGANISM: Artificial sequence
<220> FEATURE:
<223> OTHER INFORMATION: Synthetic peptide

<400> SEQUENCE: 27

Glu Pro Gly Pro Thr
1               5

<210> SEQ ID NO 28
<211> LENGTH: 4
<212> TYPE: PRT
<213> ORGANISM: Artificial sequence
<220> FEATURE:
<223> OTHER INFORMATION: Synthetic peptide

<400> SEQUENCE: 28

Glu Ala Pro Lys
1
```